US012588874B2

(12) United States Patent
Shochat et al.

(10) Patent No.: US 12,588,874 B2
(45) Date of Patent: Mar. 31, 2026

(54) OPTIMIZING CHECKPOINT LOCATIONS ALONG AN INSERTION TRAJECTORY OF A MEDICAL INSTRUMENT USING DATA ANALYSIS

(71) Applicant: XACT ROBOTICS LTD., Caesarea (IL)

(72) Inventors: Moran Shochat, Zikron Ya'aqov (IL); Ido Roth, Pardes Hanna (IL); Oz Moskovich, Moshav Moledet (IL); Danna Perlman, Haifa (IL); Gal Atarot, Kfar Saba (IL)

(73) Assignee: XACT ROBOTICS LTD., Caesarea (IL)

( * ) Notice: Subject to any disclaimer, the term of this patent is extended or adjusted under 35 U.S.C. 154(b) by 544 days.

(21) Appl. No.: 17/968,471

(22) Filed: Oct. 18, 2022

(65) Prior Publication Data

US 2023/0044419 A1 Feb. 9, 2023

Related U.S. Application Data

(63) Continuation of application No. PCT/IL2021/050441, filed on Apr. 19, 2021.

(Continued)

(51) Int. Cl.
*A61B 5/00* (2006.01)
*A61B 5/02* (2006.01)
(Continued)

(52) U.S. Cl.
CPC ........ *A61B 5/7267* (2013.01); *A61B 5/02042* (2013.01); *A61B 5/08* (2013.01);
(Continued)

(58) Field of Classification Search
CPC ......... A61B 34/10; A61B 34/20; A61B 34/25; A61B 34/32; A61B 34/107; A61B 34/2065
See application file for complete search history.

(56) References Cited

U.S. PATENT DOCUMENTS 8,348,861 B2   1/2013   Glozman et al.
8,663,130 B2   3/2014   Neubach et al.
(Continued)

FOREIGN PATENT DOCUMENTS

WO   2018106950 A1   6/2018
WO   2018188466 A1   10/2018
(Continued)

OTHER PUBLICATIONS

Ng et al (2019) Optimization of the penetrative path during grommet insertion in a robotic ear surgery, Mechatronics, Jun. 1; 60:1-4. https://doi.org/10.1016/j.mechatronics.2019.04.006.
(Continued)

*Primary Examiner* — Benjamin O Dulaney
(74) *Attorney, Agent, or Firm* — The Roy Gross Law Firm, LLC; Roy D. Gross

(57) ABSTRACT

Provided are computer-implemented methods and systems for generating and/or utilizing model(s) for determining optimized checkpoint locations along a trajectory in an image-guided procedure for inserting a medical instrument to a target in a body of a patient based, inter alia, on data related to an automated medical device and/or to operation thereof.

20 Claims, 21 Drawing Sheets

Related U.S. Application Data

(60) Provisional application No. 63/012,196, filed on Apr. 19, 2020.

(51) Int. Cl.

| | |
|---|---|
| *A61B 5/08* | (2006.01) |
| *A61B 5/107* | (2006.01) |
| *A61B 34/10* | (2016.01) |
| *A61B 34/20* | (2016.01) |
| *A61B 34/30* | (2016.01) |
| *A61B 34/32* | (2016.01) |
| *G06N 20/00* | (2019.01) |
| *G06T 7/00* | (2017.01) |
| *G16H 20/40* | (2018.01) |
| *G16H 30/20* | (2018.01) |
| *G16H 50/50* | (2018.01) |

(52) U.S. Cl.
CPC ............ *A61B 5/1073* (2013.01); *A61B 5/489* (2013.01); *A61B 5/7275* (2013.01); *A61B 5/746* (2013.01); *A61B 34/10* (2016.02); *A61B 34/32* (2016.02); *G06N 20/00* (2019.01); *G06T 7/0012* (2013.01); *G16H 20/40* (2018.01); *G16H 30/20* (2018.01); *G16H 50/50* (2018.01); *A61B 2034/107* (2016.02); *A61B 2034/2065* (2016.02); *A61B 2034/301* (2016.02); *G06T 2207/10* (2013.01)

(56) References Cited

U.S. PATENT DOCUMENTS

| | | | |
|---|---|---|---|
| 9,420,995 | B2 | 8/2016 | Neubach et al. |
| 9,743,996 | B2 | 8/2017 | Neubach et al. |
| 10,245,110 | B2 | 4/2019 | Shochat |
| 10,507,067 | B2 | 12/2019 | Glozman et al. |
| 10,517,681 | B2* | 12/2019 | Roh ......................... G06N 3/09 |
| 10,639,107 | B2 | 5/2020 | Glozman et al. |
| 2006/0241368 | A1 | 10/2006 | Fichtinger |
| 2010/0056900 | A1 | 3/2010 | Whitcomb |
| 2013/0262357 | A1 | 10/2013 | Amarasingham |
| 2017/0071672 | A1* | 3/2017 | Shochat .................... G06T 7/11 |
| 2017/0258489 | A1 | 9/2017 | Galili et al. |
| 2017/0348061 | A1 | 12/2017 | Joshi et al. |
| 2018/0250078 | A1* | 9/2018 | Shochat ............. A61B 17/3403 |
| 2018/0279852 | A1 | 10/2018 | Rafii-Tari et al. |
| 2018/0296281 | A1* | 10/2018 | Yeung ................... A61B 34/32 |
| 2018/0368930 | A1 | 12/2018 | Esterberg et al. |
| 2019/0029757 | A1* | 1/2019 | Roh ....................... A61B 5/748 |
| 2019/0125397 | A1 | 5/2019 | Arnold et al. |
| 2019/0239973 | A9 | 8/2019 | Esterberg et al. |
| 2019/0262084 | A1 | 8/2019 | Roh et al. |
| 2019/0290372 | A1 | 9/2019 | Arnold et al. |
| 2019/0350659 | A1 | 11/2019 | Wang et al. |
| 2020/0051274 | A1* | 2/2020 | Siemionow ............ A61B 34/10 |
| 2020/0085509 | A1 | 3/2020 | Roh et al. |
| 2021/0177522 | A1 | 6/2021 | Boddington |
| 2021/0315649 | A1* | 10/2021 | Kaethner ............... A61B 34/30 |

FOREIGN PATENT DOCUMENTS

| | | |
|---|---|---|
| WO | 2019234748 A1 | 12/2019 |
| WO | 2020056086 A1 | 3/2020 |
| WO | 2021105992 A1 | 6/2021 |
| WO | 2021105993 A1 | 6/2021 |
| WO | 2021111445 A1 | 6/2021 |
| WO | 2021214750 A1 | 10/2021 |
| WO | 2021214751 A1 | 10/2021 |
| WO | 2021214754 A1 | 10/2021 |

OTHER PUBLICATIONS

Dominic, et al (2019) Combining Predictive Analytics and Artificial Intelligence with Human Intelligence in IoT-Based Image-Guided Surgery, Internet of Things in Biomedical Engineering, pp. 259-289. https://doi.org/10.1016/B978-0-12-817356-5.00014-0.

Regodic et al (2020) Automatic Fiducial marker detection and localization in CT images: a combined approach, SPIE Medical Imaging, Houston, Texas. DOI: 10.1117/12.2548852.

PCT International Search Report for International Application No. PCT/IL2021/050441, mailed Jun. 21, 2021, 6pp.

PCT Written Opinion for International Application No. PCT/IL2021/050441, mailed Jun. 21, 2021, 5pp.

PCT International Preliminary Report on Patentability for International Application No. PCT/IL2021/050441, issued Oct. 25, 2022, 6pp.

Taylor, Andrew G, Clinton Mielke, and John Mongan. "Automated Detection of Moderate and Large Pneumothorax on Frontal Chest X-Rays Using Deep Convolutional Neural Networks: A Retrospective Study." PLoS medicine 15.11 (2018): e1002697-e1002697. Web. (Year: 2018).

Huo YR, Chan MV, Habib AR, Lui I, Ridley L. Pneumothorax rates in CT-Guided lung biopsies: a comprehensive systematic review and meta-analysis of risk factors. Br J Radiol. Apr. 1, 2020;93(1108):20190866. doi: 10.1259/bjr.20190866. Epub Jan. 3, 2020. (Year: 2020).

* cited by examiner

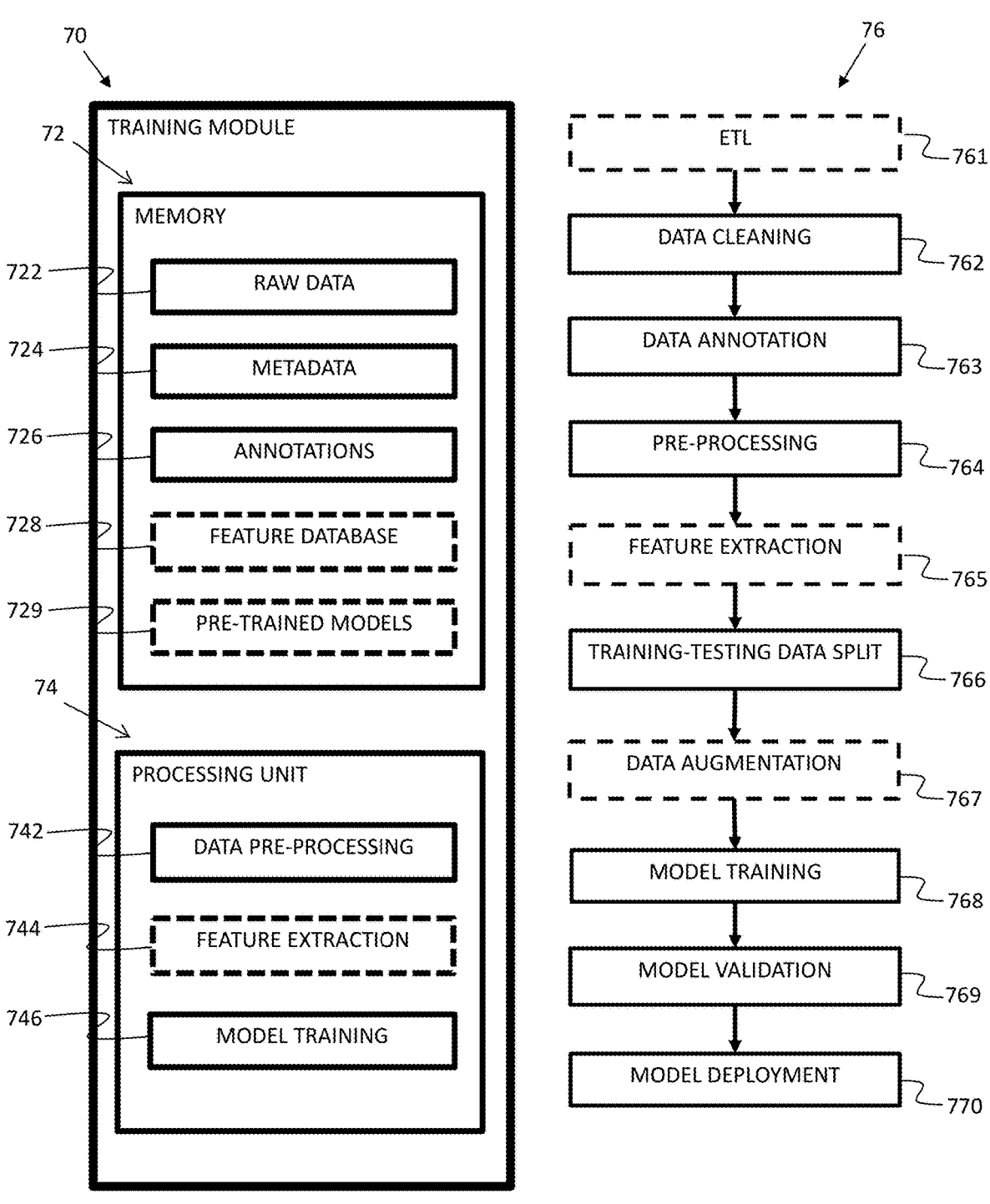
FIG. 7A          FIG. 7B

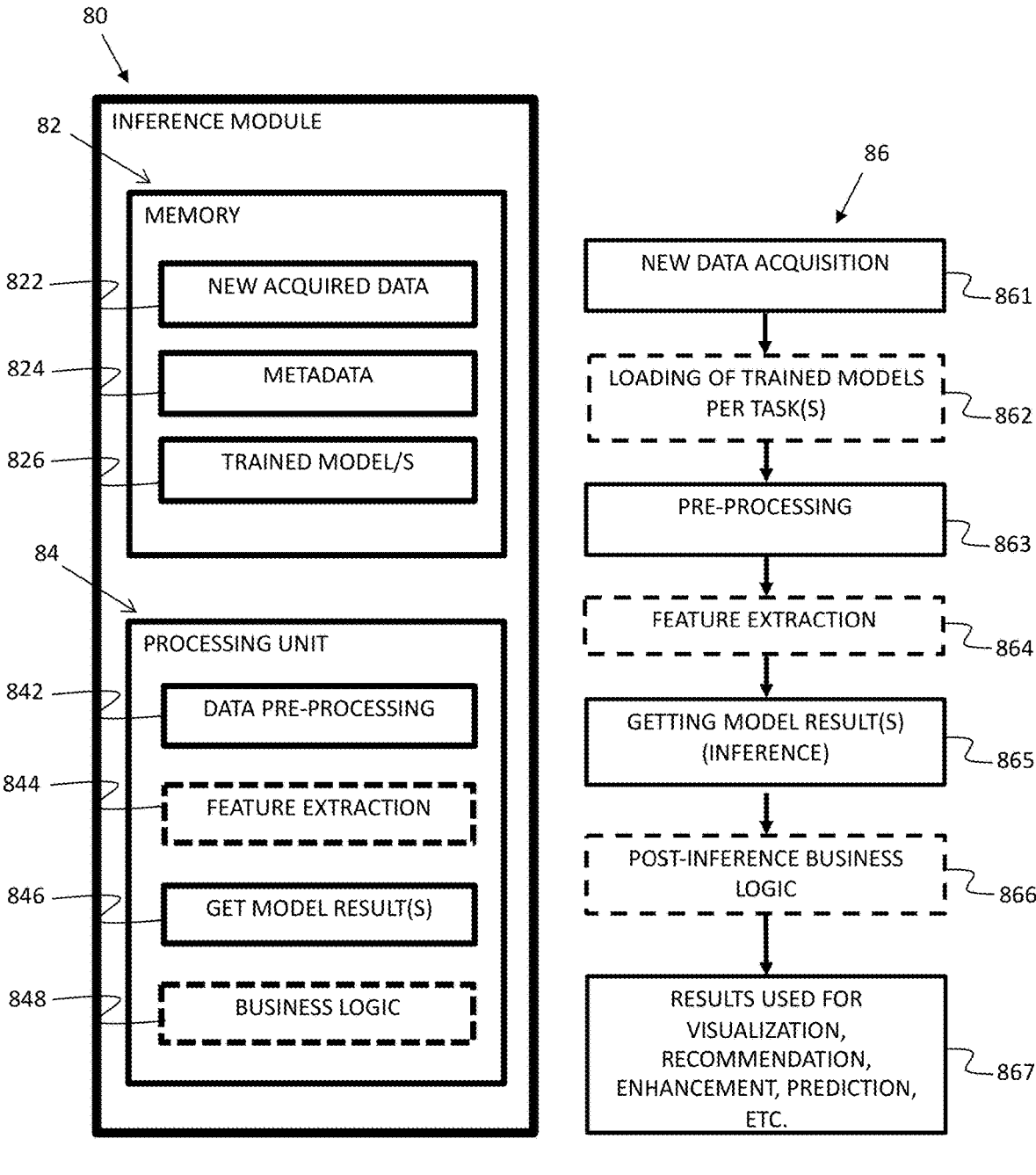
FIG. 8A                    FIG. 8B

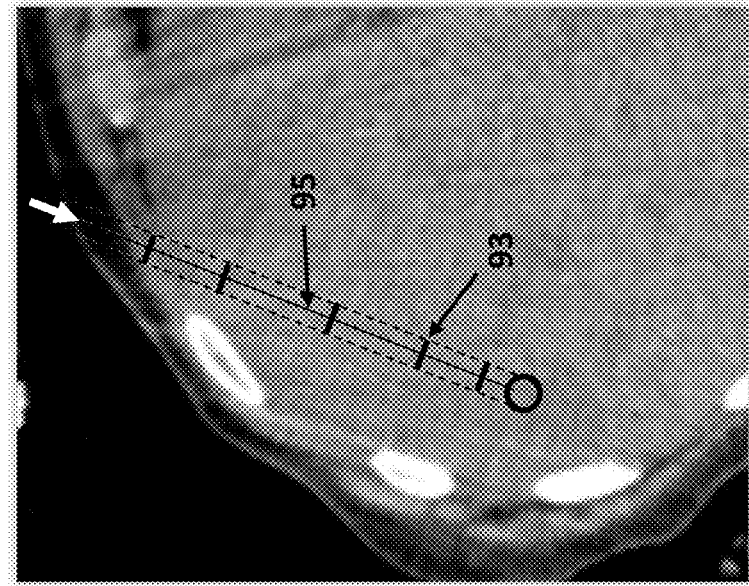
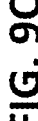
FIG. 9C
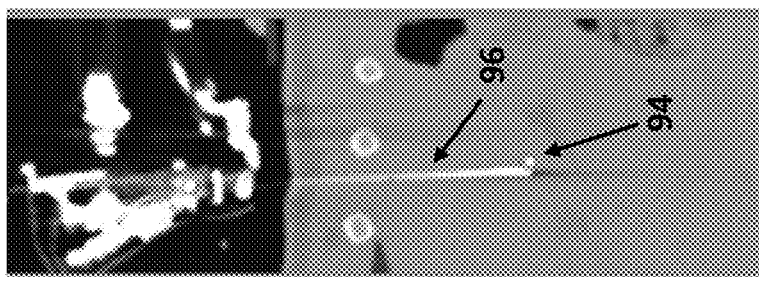
FIG. 9B
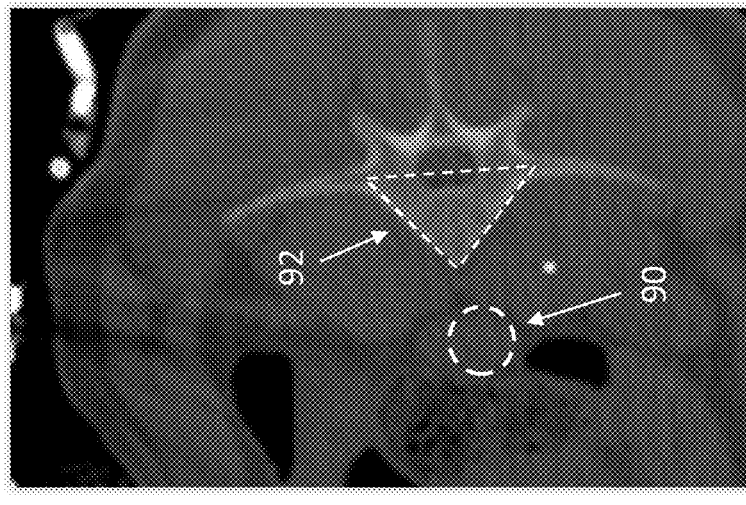
FIG. 9A

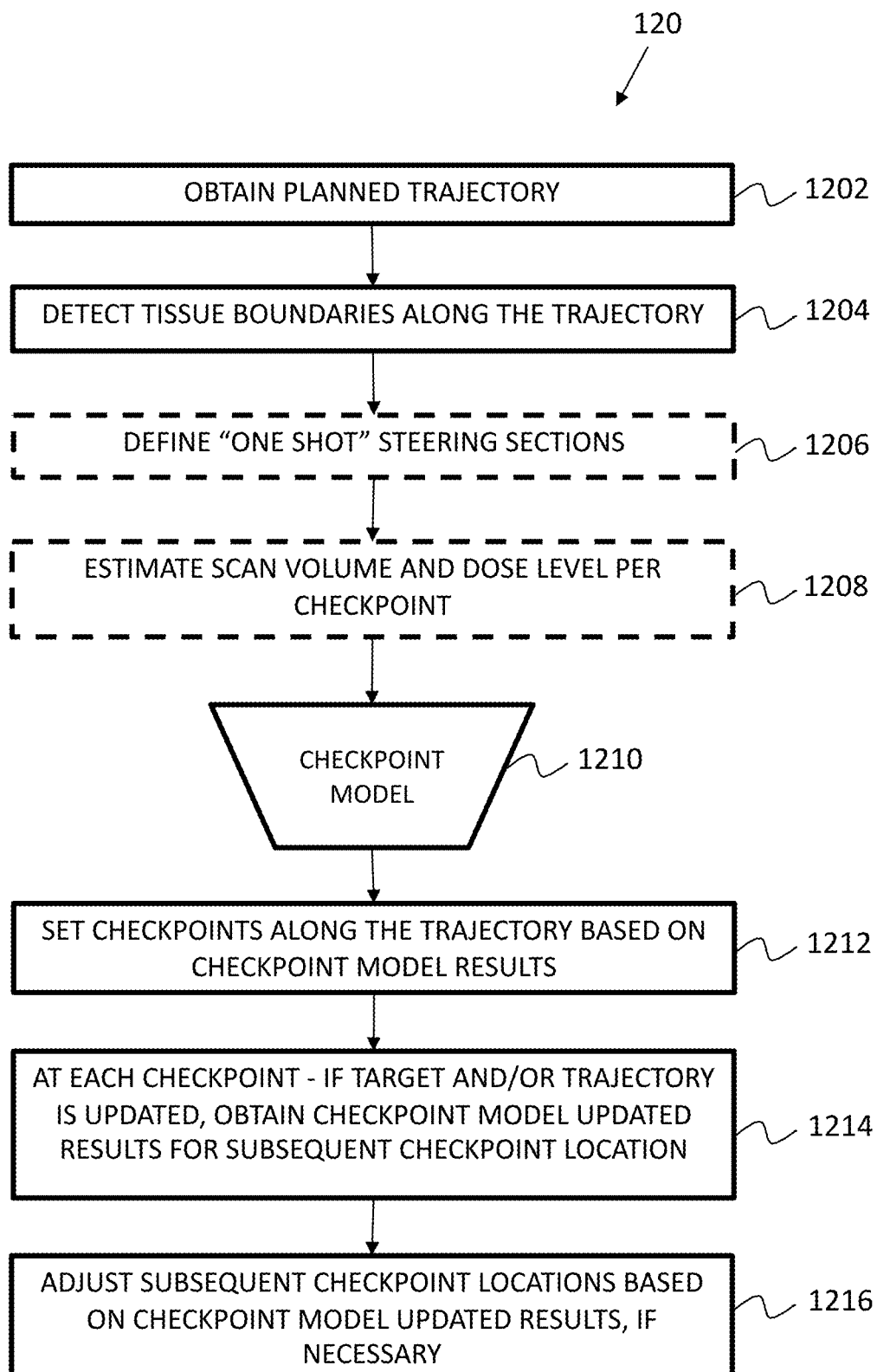

120

OBTAIN PLANNED TRAJECTORY — 1202

DETECT TISSUE BOUNDARIES ALONG THE TRAJECTORY — 1204

DEFINE "ONE SHOT" STEERING SECTIONS — 1206

ESTIMATE SCAN VOLUME AND DOSE LEVEL PER CHECKPOINT — 1208

CHECKPOINT MODEL — 1210

SET CHECKPOINTS ALONG THE TRAJECTORY BASED ON CHECKPOINT MODEL RESULTS — 1212

AT EACH CHECKPOINT - IF TARGET AND/OR TRAJECTORY IS UPDATED, OBTAIN CHECKPOINT MODEL UPDATED RESULTS FOR SUBSEQUENT CHECKPOINT LOCATION — 1214

ADJUST SUBSEQUENT CHECKPOINT LOCATIONS BASED ON CHECKPOINT MODEL UPDATED RESULTS, IF NECESSARY — 1216

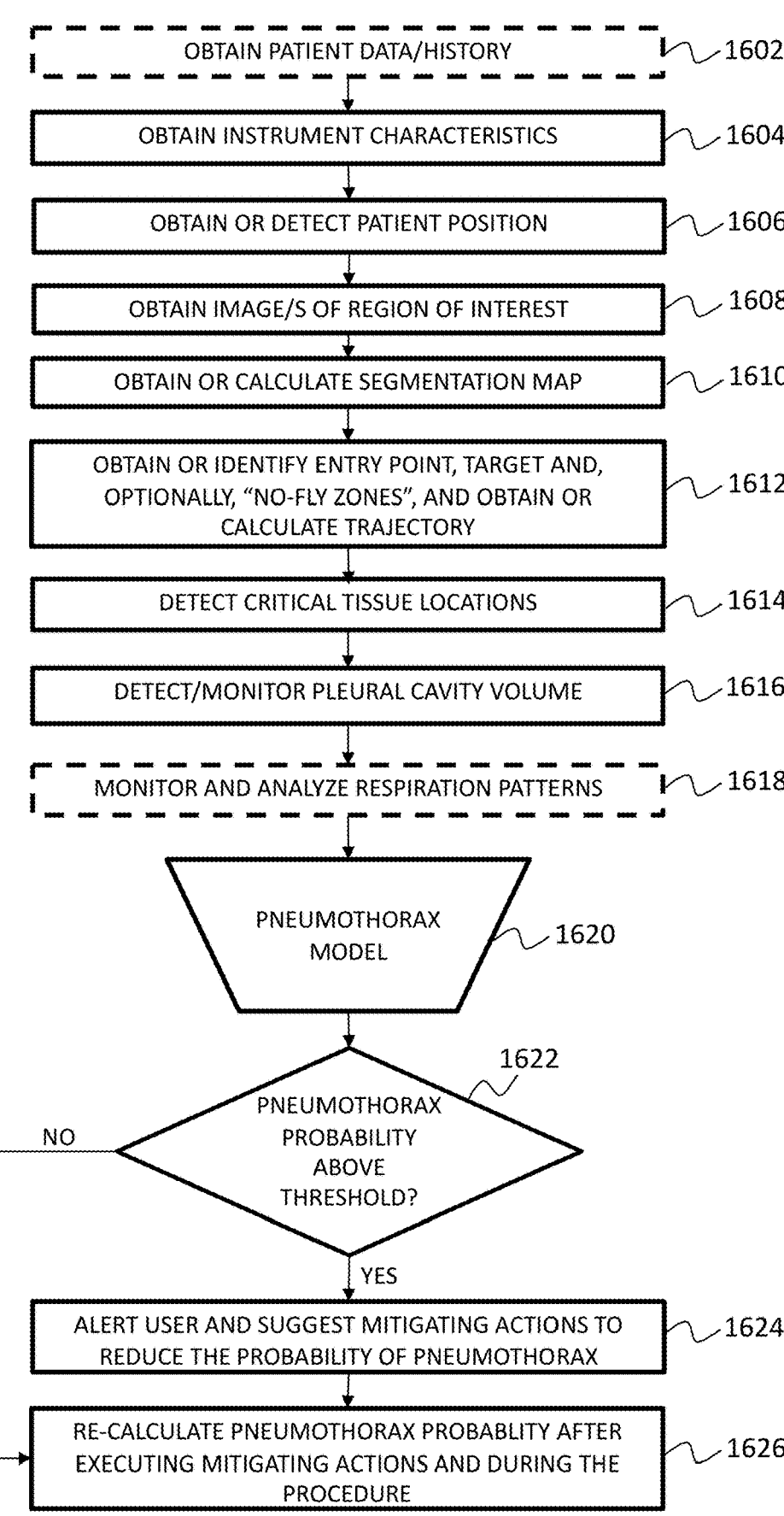

OBTAIN PATIENT DATA/HISTORY — 1602

OBTAIN INSTRUMENT CHARACTERISTICS — 1604

OBTAIN OR DETECT PATIENT POSITION — 1606

OBTAIN IMAGE/S OF REGION OF INTEREST — 1608

OBTAIN OR CALCULATE SEGMENTATION MAP — 1610

OBTAIN OR IDENTIFY ENTRY POINT, TARGET AND, OPTIONALLY, "NO-FLY ZONES", AND OBTAIN OR CALCULATE TRAJECTORY — 1612

DETECT CRITICAL TISSUE LOCATIONS — 1614

DETECT/MONITOR PLEURAL CAVITY VOLUME — 1616

MONITOR AND ANALYZE RESPIRATION PATTERNS — 1618

PNEUMOTHORAX MODEL — 1620

PNEUMOTHORAX PROBABILITY ABOVE THRESHOLD? — 1622

NO

YES

ALERT USER AND SUGGEST MITIGATING ACTIONS TO REDUCE THE PROBABILITY OF PNEUMOTHORAX — 1624

RE-CALCULATE PNEUMOTHORAX PROBABLITY AFTER EXECUTING MITIGATING ACTIONS AND DURING THE PROCEDURE — 1626

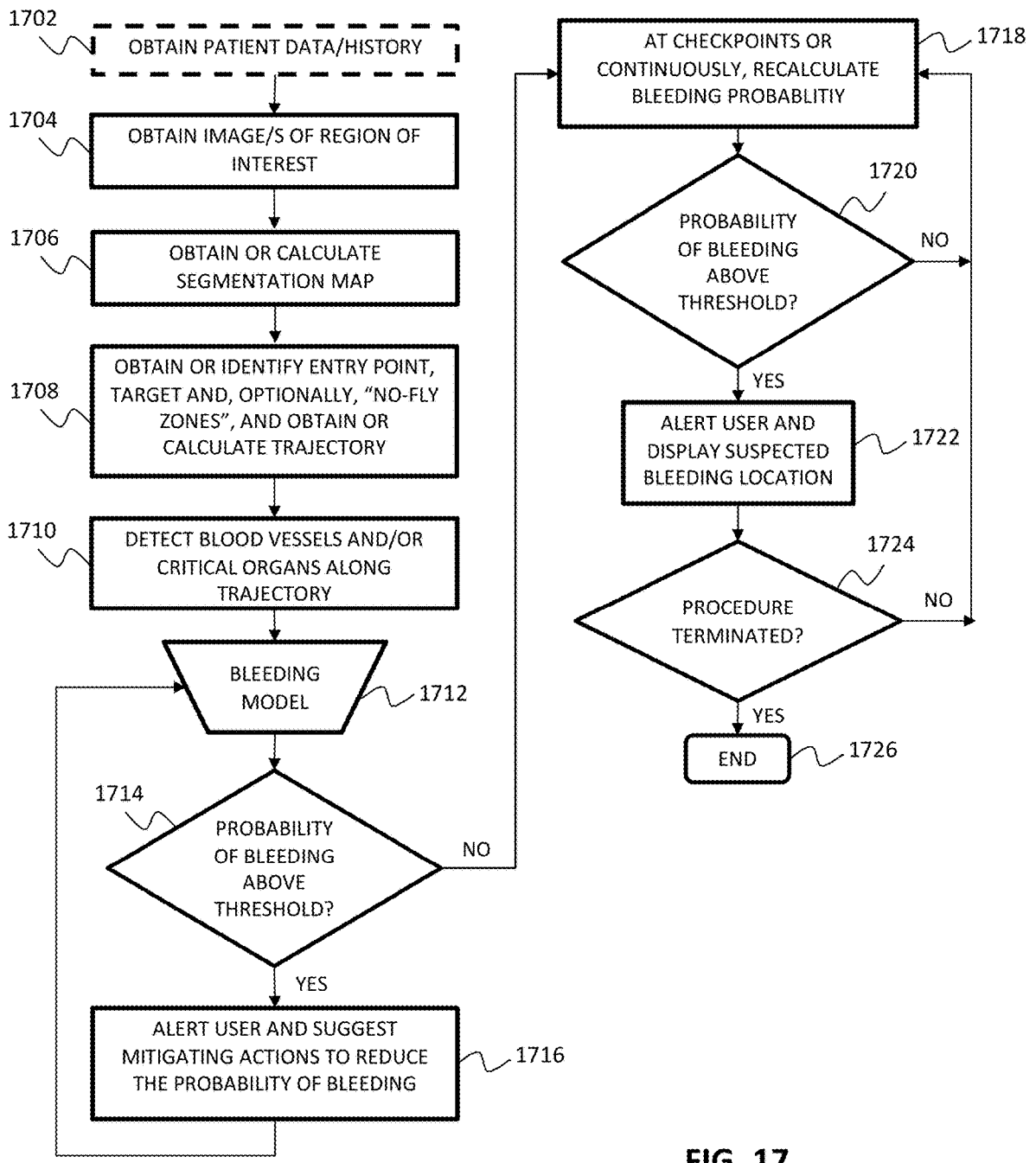

1702 OBTAIN PATIENT DATA/HISTORY

1704 OBTAIN IMAGE/S OF REGION OF INTEREST

1706 OBTAIN OR CALCULATE SEGMENTATION MAP

1708 OBTAIN OR IDENTIFY ENTRY POINT, TARGET AND, OPTIONALLY, "NO-FLY ZONES", AND OBTAIN OR CALCULATE TRAJECTORY

1710 DETECT BLOOD VESSELS AND/OR CRITICAL ORGANS ALONG TRAJECTORY

1712 BLEEDING MODEL

1714 PROBABILITY OF BLEEDING ABOVE THRESHOLD?

NO

YES

1716 ALERT USER AND SUGGEST MITIGATING ACTIONS TO REDUCE THE PROBABILITY OF BLEEDING

1718 AT CHECKPOINTS OR CONTINUOUSLY, RECALCULATE BLEEDING PROBABLITIY

1720 PROBABILITY OF BLEEDING ABOVE THRESHOLD?

NO

YES

1722 ALERT USER AND DISPLAY SUSPECTED BLEEDING LOCATION

1724 PROCEDURE TERMINATED?

NO

YES

1726 END

FIG. 17

OPTIMIZING CHECKPOINT LOCATIONS ALONG AN INSERTION TRAJECTORY OF A MEDICAL INSTRUMENT USING DATA ANALYSIS

CROSS REFERENCE TO RELATED APPLICATIONS

This application is a Bypass Continuation of PCT Patent Application No. PCT/IL2021/050441 having International filing date of Apr. 19, 2021, which claims the benefit of priority of U.S. Provisional Patent Application No. 63/012, 196, filed Apr. 19, 2020, the contents of which are all incorporated herein by reference in their entirety

FIELD OF THE INVENTION

The present invention relates to computer-implemented methods and systems for collecting data related to operation of automated medical devices, and utilization of the data to generate algorithms to determine and/or recommend optimized checkpoint locations along a trajectory for inserting a medical instrument toward an internal target.

BACKGROUND

Various diagnostic and therapeutic procedures used in clinical practice involve the insertion of medical instruments, such as needles and catheters, percutaneously to a subject's body, and in many cases further involve the steering of the medical instruments within the body, to reach a target region. The target region can be, for example, a lesion, a tumor, an organ and/or a vessel. Examples of procedures requiring insertion and steering of such medical instruments include vaccinations, blood/fluid sampling, regional anesthesia, tissue biopsy, catheter insertion, cryogenic ablation, electrolytic ablation, brachytherapy, neurosurgery, deep brain stimulation, various minimally invasive surgeries, and the like.

The guidance and steering of medical instruments in the body is a complicated task that requires good three-dimensional coordination, knowledge of the patient's anatomy and a high level of experience. Thus, image-guided automated (e.g., robotic) systems have been proposed for performing these functions.

Some automated systems are based on manipulating robotic arm(s) and some utilize a robotic device which can be attached to the patient's body or positioned in close proximity thereto. These automated systems typically assist the physician in aligning the medical instrument with a selected insertion point at a desired insertion point and the insertion itself is carried out manually by the physician. Some automated systems further include an insertion mechanism that can insert the instrument toward the target, typically in a linear manner. More advanced automated systems further include non-linear steering capabilities, as described, for example, in U.S. Pat. Nos. 8,348,861, 8,663, 130 and 10,507,067, and in co-owned U.S. Pat. No. 10,245, 110, co-owned U.S. Patent Application Publication No. 2019/290,372, and co-owned International Patent Application No. PCT/IL2020/051219, all of which are incorporated herein by reference in their entireties.

During the operation of such automated medical devices in various procedures and in various settings, a large amount of related data is accumulated. The utilization of such data to improve and enhance the operation and clinical value of these automated devices, as well as to predict and/or detect clinical conditions, and specifically, clinical complications, may ultimately improve the health and safety of the patients.

Thus, there is a need in the art for methods and systems for collecting and processing the data related to and/or generated by automated medical devices, and for generating and implementing data-analysis algorithms (e.g., artificial intelligence (AI) models) that can utilize the accumulated data to provide operating recommendations, operating instructions, functionality enhancements, clinical evaluations and predictions, etc.

SUMMARY

According to some embodiments, the present disclosure is directed to systems and computer-implemented methods for the collection of various types of datasets related to and/or obtained from operation of automated medical devices and the consequent manipulation and/or utilization of the data, to generate algorithms (or—models) to one or more of: affect, control and/or manipulate the operation of automated devices, generate recommendation to users of automated devices, and/or predict clinical conditions and/or complications, based on at least some of the collected data and/or parameters derived therefrom. In some embodiments, the computerized methods may utilize specific algorithms which may be generated using machine learning tools, deep learning tools, data wrangling tools, and, more generally, AI and data analysis tools. In some embodiments, the specific algorithms may be implemented using artificial neural network(s) (ANN), such as convolutional neural network (CNN), recurrent neural network (RNN), long-short term memory (LSTM), auto-encoder (AE), generative adversarial network (GAN), Reinforcement-Learning (RL) and the like, as further detailed below. In other embodiments, the specific algorithms may be implemented using machine learning methods, such as support vector machine (SVM), decision tree (DT), random forest (RF), and the like. Both "supervised" and "unsupervised" methods may be implemented.

In some embodiments, data is collected during or resulting from procedures performed by the automated medical devices. In some embodiments, the collected data may be used, to generate an algorithm/model, which may consequently provide, for example, instructions, enhancements or recommendations regarding various operating parameters and/or other parameters related to automated medical devices. Thus, based at least on some of the collected primary data (also referred to as "raw data") and/or metadata and/or data and/or features derived therefrom ("manipulated data") and/or annotations generated manually or automatically, a data-analysis algorithm may be generated, to provide output that can enhance the operation of the automated medical devices and/or the decisions of the users (e.g., physicians) of such devices.

In some exemplary embodiments, the automated medical devices are devices for insertion and steering of medical instruments (for example, needles, introducers or probes) in a subject's body for various diagnostic and/or therapeutic purposes. In some embodiments, the automated insertion device may utilize real-time instrument position prediction and real-time trajectory updating, as disclosed, for example, in abovementioned co-owned International Patent Application No. PCT/IL2020/051219. For example, when utilizing real-time trajectory updating and steering, the most effective spatio-temporal and safe route of the medical instrument to the target within the body may be achieved. Further, safety may be increased as it reduces the risk of harming non-target regions and tissues within the subject's body, as the trajectory update may take into account obstacles or any other regions along the route, and moreover, may take into account changes in the real-time location of such obstacles. Additionally, such automatic steering may improve the accuracy of the procedures, thus enabling reaching small and hard to reach targets. This can be of particular importance in early detection of malignant neoplasms, for example. In addition, it provides increased safety for the patient, as there is a significant lower risk of human error. Further, such a procedure may be safer for the medical personnel, as it may minimize their exposure to radiation and/or pathogens during the procedure. In some embodiments, the automated medical devices are configured to insert and steer/navigate a medical instrument (in particular, the tip of the medical instrument) in the body of the subject, to reach a target region within the subject's body, to perform various medical procedures. In some embodiments, the operation of the medical devices may be controlled by at least one processor configured to provide instructions, in real-time, to steer the medical instrument and the tip thereof, toward the target, according to a planned and/or the updated trajectory. In some embodiments, the steering may be controlled by the processor, via a suitable controller. In some embodiments the steering may be controlled in a closed-loop manner, whereby the processor generates motion commands to the steering device via a suitable controller and receives feedback regarding the real-time location of the medical instrument and/or the target. In some embodiments, the processor(s) may be able to predict the location and/or movement pattern of the target. AI-based algorithm(s) may be used to predict the location and/or movement pattern of the target. In some embodiments, the automated medical device may be configured to operate in conjunction with an imaging system. In some embodiments, the imaging system may include any type of imaging system, including, but not limited to: X-ray fluoroscopy, CT, cone beam CT, CT fluoroscopy, MRI, ultrasound, or any other suitable imaging modality. In some embodiments, the processor is configured to calculate a trajectory for the medical instrument based on a target, entry point and, optionally, obstacles en route (such as bones or blood vessels), which may be manually marked by the user, or automatically identified by the processor, on one or more obtained images.

In some embodiments, the primary datasets collected and utilized by the systems and methods disclosed herein may include several types of sets of primary data, including, for example, clinical related dataset, patient related dataset, device related dataset and/or administrative dataset. The collected datasets may then be manipulated/processed, utilizing data analysis algorithms, machine learning algorithms and/or deep learning algorithms, to generate an algorithm or a model, which may output, inter alia, recommendations and/or operating instructions for the automated medical device, to thereby enhance their operation.

According to some embodiments, the collected datasets and/or the data derived therefrom may be used for the generation of a training set, which may be part of the generated algorithm/model, or utilized for the generation of the model/algorithm and/or the validation or update thereof. In some embodiments, the training step may be performed in an "offline" manner, i.e., the model may be trained/generated based on a static dataset. In some embodiments, the training step may be performed utilizing an "online" or incremental/continuous manner, in which the model is continuously updated with every new incoming data.

According to some embodiments, there is thus provided a computer-implemented method of generating a checkpoint locations model for optimizing locations of checkpoints along a trajectory in an image-guided procedure for inserting a medical instrument toward a target in a body of a patient, the method including:

collecting one or more datasets, at least one of the one or more datasets being related to an automated medical device configured to steer a medical instrument toward a target in the body of a patient and/or to operation thereof;

creating a training set which may include at least a portion of the one or more datasets and one or more target parameters relating to checkpoint locations along a trajectory in one or more previous image-guided procedures for inserting a medical instrument toward a target in a body of a patient;

training the checkpoint locations model to predict checkpoint locations using the training set;

calculating a checkpoint locations prediction error; and optimizing the checkpoint locations model using the calculated checkpoint locations prediction error.

According to some embodiments, the one or more datasets may further include one or more of: clinical procedure related dataset, patient related dataset and administrative related dataset.

According to some embodiments, the automated medical device related dataset may include parameters selected from: entry point, insertion angles, target position, target position updates, target contour and/or bounding box and/or location, "no-fly" zones masks and/or bounding boxes and/or locations, organs segmentation masks and/or bounding boxes and/or locations, tissues segmentation mask and/or bounding boxes and/or locations, blood vessels mask and/or bounding boxes and/or locations, planned trajectory, trajectory updates, real-time positions of the medical instrument, number of checkpoints along the planned and/or updated trajectory, checkpoint locations, checkpoint locations updates, checkpoint errors, position of the automated medical device, steering steps timing, procedure duration, steering phase duration, procedure accuracy, target error, medical images, medical imaging parameters per scan, radiation dose per scan, total radiation dose in steering phase, total radiation dose procedure, sensor(s) measurements, errors indicated during the steering procedure, software logs, motion control traces, automated medical device registration logs, medical instrument detection logs, homing and BIT results, or any combination thereof.

According to some embodiments, at least one of the parameters of the automated medical device related dataset may be used as a training parameter (data annotation).

According to some embodiments, the clinical procedure related dataset may include parameters selected from: medical procedure type, target organ, target size, target type, type of medical instrument, dimensions of the medical instrument, clinical complications before, during and/or after the procedure, complications detection time, adverse events before, during and/or after the procedure, respiration signals of the patient, or any combination thereof.

According to some embodiments, the medical procedure type may be selected from: fluid sampling, regional anesthesia, tissue biopsy, catheter insertion, cryogenic ablation, electrolytic ablation, brachytherapy, neurosurgery, deep brain stimulation, minimally invasive surgery, or any combination thereof.

According to some embodiments, the patient related dataset may include parameters selected from: age, gender, race, medical condition, medical history, vital signs before, after and/or during the procedure, body dimensions, pregnancy, smoking habits, demographic data, or any combination thereof.

According to some embodiments, the administrative related dataset may include parameters selected from: institution, physician, staff, system serial number, disposable components used in the procedure, software version, operating system version, configuration parameters, or any combination thereof.

According to some embodiments, one or more of the parameters of the one or more datasets may be configured to be collected automatically.

According to some embodiments, the checkpoint locations model may be generated utilizing artificial intelligence tools. In some embodiments, the artificial intelligence tools may include one or more of: machine learning tools, data wrangling tools, deep learning tools, artificial neural network (ANN), deep neural network (DNN), convolutional neural network (CNN), recurrent neural network (RNN), long short term memory network (LSTM), decision trees or graphs, association rule learning, support vector machines, inductive logic programming, Bayesian networks, instance-based learning, manifold learning, sub-space learning, dictionary learning, reinforcement learning (RL), generative adversarial network (GAN), clustering algorithms, or any combination thereof.

According to some embodiments, training the checkpoint locations model may include using one or more of: loss function, Ensemble Learning methods, Multi-Task Learning, Multi-Output regression and Multi-Output classification.

According to some embodiments, the method of generating a checkpoint locations model for optimizing locations of checkpoints may further include:

executing one or more individual models using at least a portion of the one or more datasets and a checkpoint locations prediction generated by the checkpoint locations model; and obtaining one or more predictions from the one or more individual models.

According to some embodiments, the method of generating a checkpoint locations model may further include:

calculating a loss function using a checkpoint locations prediction error and the one or more predictions generated by the one or more individual models; and optimizing the checkpoint locations model using the loss function.

According to some embodiments, the method of generating a checkpoint locations model may further include training the one or more individual models.

According to some embodiments, the one or more individual models may include a model for predicting an accuracy of an image-guided insertion procedure.

According to some embodiments, the one or more individual models may include a model for predicting a radiation dose emitted during an image-guided insertion procedure, or part thereof.

According to some embodiments, the one or more individual models may include a model for predicting a duration of an image-guided insertion procedure, or part thereof.

According to some embodiments, the one or more individual models may include a model for predicting a risk of an image-guided insertion procedure.

According to some embodiments, calculating the loss function may include minimizing the checkpoint locations prediction error.

According to some embodiments, calculating the loss function may include minimizing the predicted radiation dose.

According to some embodiments, calculating the loss function may include minimizing the predicted duration.

According to some embodiments, calculating the loss function may include minimizing the predicted risk.

According to some embodiments, calculating the loss function may include maximizing the predicted accuracy of the image-guided insertion procedure.

According to some embodiments, the method of generating a checkpoint locations model may further include adjusting one or more coefficients of one or more terms used in the calculation of the loss function, the one or more terms being associated with at least one of the checkpoint locations prediction error and the one or more predictions generated by the one or more individual models.

According to some embodiments, the adjusting of the one or more coefficients may be executed during training of the checkpoint locations model.

According to some embodiments, the adjusting of the one or more coefficients may be executed during execution of the checkpoint locations model.

According to some embodiments, generating the checkpoint locations model may be executed by a training module which may include a memory and one or more processors.

According to some embodiments, the automated medical device may be configured to steer the medical instrument toward the target such that the medical instrument traverses a non-linear trajectory within the body of the patient.

According to some embodiments, the automated medical device may be configured to allow real-time updating of a trajectory of the medical instrument.

According to some embodiments, there is provided a system for generating a checkpoint locations model for optimizing locations of checkpoints along a trajectory in an image-guided procedure for inserting a medical instrument to an internal target, the system includes:

a training module including:

a memory configured to store the one or more datasets; and one or more processors configured to execute the method of any one of the method of generating a checkpoint locations model disclosed herein.

According to some embodiments, the training module may be located on a remote server, an "on premise" server or a computer associated with the automated medical device.

According to some embodiments, the remote server may be a cloud server.

According to some embodiments, there is provided a computer-implemented method of utilizing a checkpoint locations model for optimizing locations of checkpoints along a trajectory in an image-guided procedure for inserting a medical instrument to a target in a body of a patient, the method includes:

collecting one or more new datasets, at least one of the one or more new datasets being related to an automated medical device configured to steer a medical instrument toward a target in a body of a patient and/or to operation thereof and including one or more images of a region of interest and a planned trajectory for the medical instrument from an entry point to the target;

detecting one or more tissue boundaries in the one or more images;

executing the checkpoint locations model using at least a portion of the one or more new datasets;

obtaining an output of the checkpoint locations model; and setting one or more checkpoints along the planned trajectory based on the output of the checkpoint locations model.

According to some embodiments, the method of utilizing a checkpoint locations model may further include obtaining from a user at least one of a confirmation to the set one or more checkpoints and an adjustment thereto.

According to some embodiments, the method of utilizing a checkpoint locations model may further include defining one or more sections along the planned trajectory in which no checkpoints are to be positioned, so as to allow the medical instrument to be continuously advanced along the one or more sections.

According to some embodiments, the method of utilizing a checkpoint locations model may further include estimating a scan volume and a radiation dose per checkpoint.

According to some embodiments, the automated medical device may be configured to allow real-time updating of a trajectory of the medical instrument.

According to some embodiments, if at least one of a position of the target and the planned trajectory are updated upon reaching a checkpoint, the method of utilizing a checkpoint locations model may further include re-executing the checkpoint locations model and obtaining an updated output of the checkpoint locations model.

According to some embodiments, the method of utilizing a checkpoint locations model may further include adjusting the locations of one or more subsequent checkpoints based on the updated output of the checkpoint locations model.

According to some embodiments, the method of utilizing a checkpoint locations model may further include obtaining from a user at least one of a confirmation to the adjusted locations of the one or more subsequent checkpoints and an adjustment thereto.

According to some embodiments, the automated medical device may be configured to steer the medical instrument toward the target in a non-linear trajectory.

According to some embodiments, there is provided a system for utilizing a checkpoint locations model for optimizing locations of checkpoints along a trajectory in an image-guided procedure for inserting a medical instrument to a target in a body of a patient, the system includes:

an inference module which may include:
a memory configured to store the one or more new datasets; and
one or more processors configured to execute the method of utilizing a checkpoint locations model as disclosed herein.

According to some embodiments, the inference module may be located on a remote server, an "on premise" server or a computer associated with the automated medical device.

According to some embodiments, the remote server may be a cloud server.

According to some embodiments, there is provided a computer-readable storage medium having stored therein machine learning software, executable by one or more processors, for generating a checkpoint locations model for optimizing locations of checkpoints along a trajectory in an image-guided procedure for inserting a medical instrument to a target in a body of a patient, by executing the methods disclosed herein.

According to some embodiments, there is provided a non-transitory computer readable medium storing computer program instructions for generating a checkpoint locations model for optimizing locations of checkpoints along a trajectory in an image-guided procedure for inserting a medical instrument to a target in a body of a patient, the computer program instructions when executed by a processor cause the processor to perform operations which may include: collecting one or more datasets, at least one of the one or more datasets being related to an automated medical device configured to steer a medical instrument toward a target in the body of a patient and/or to operation thereof; creating a training set which may include at least a portion of the one or more datasets and one or more target parameters relating to checkpoint locations along a trajectory in one or more previous image-guided procedures for inserting a medical instrument toward a target in a body of a patient; training the checkpoint locations model to predict checkpoint locations using the training set; calculating a checkpoint locations prediction error; and optimizing the checkpoint locations model using the calculated checkpoint locations prediction error.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

BRIEF DESCRIPTION OF THE DRAWINGS

Some exemplary implementations of the methods and systems of the present disclosure are described with reference to the accompanying drawings. In the drawings, like reference numbers indicate identical or substantially similar elements.

FIGS. 7A-7B show an exemplary training module (FIG. 7A) and an exemplary training process (FIG. 7B) for training a data-analysis algorithm, according to some embodiments;

FIGS. 8A-8B show an exemplary inference module (FIG. 8A) and an exemplary inference process (FIG. 8B) for utilizing a data-analysis algorithm, according to some embodiments;

FIG. 9A shows a CT image of a subject illustrating marked recommended "no-fly" zones (i.e., regions that should be avoided during instrument insertion), according to some embodiments;

FIG. 9B shows a CT image of a subject demonstrating real-time target movement during a needle insertion procedure, according to some embodiments;

FIG. 9C shows a CT image of a subject showing checkpoints (CPs) located along a planned trajectory, according to some embodiments;

FIG. 12 shows a flowchart illustrating the steps of a method of utilizing an AI model for optimizing checkpoint locations along a trajectory, according to some embodiments;

FIG. 16 shows a flowchart illustrating the steps of a method of utilizing a pneumothorax model for prediction and/or detection of pneumothorax, according to some embodiments;

FIG. 17 shows a flowchart illustrating the steps of a method of utilizing a pneumothorax model for prediction and/or detection of internal bleeding, according to some embodiments.

DETAILED DESCRIPTION

Figure 1:
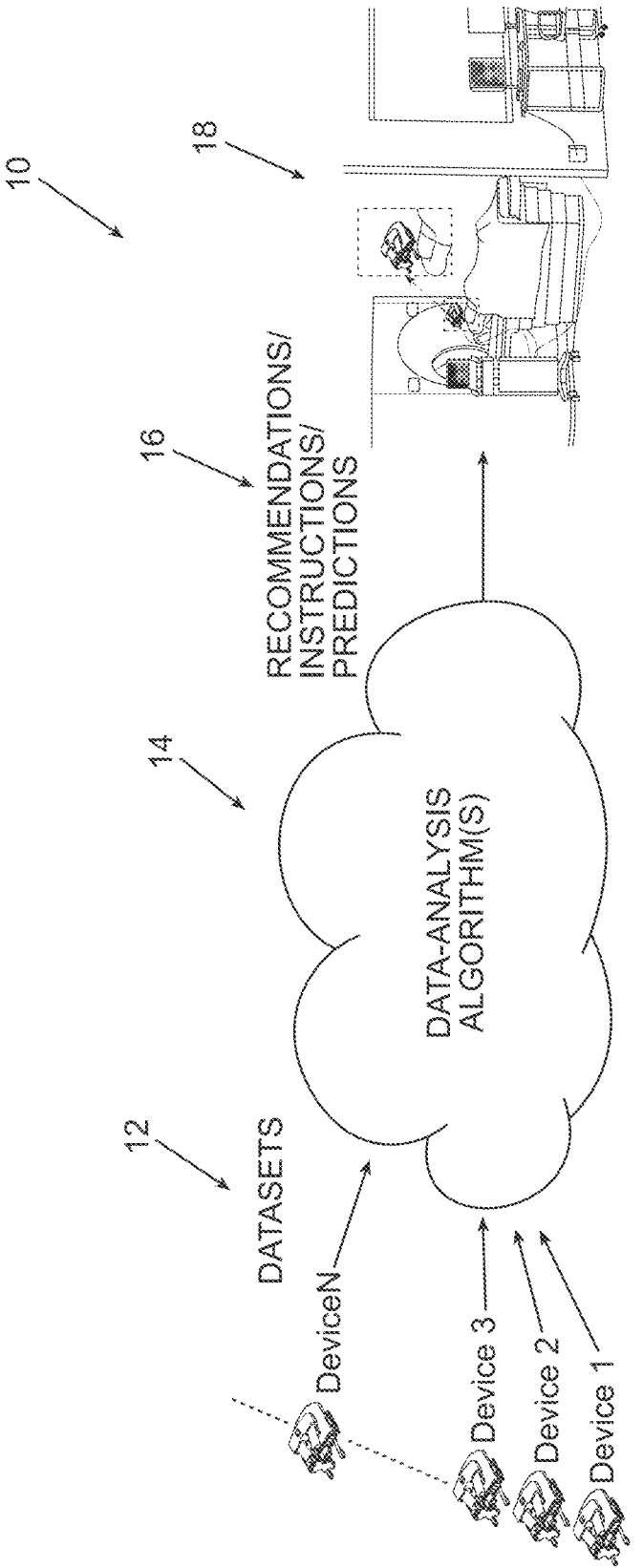
FIG. 1 shows a schematic illustration of a system for generating and using data-analysis model(s)/algorithm(s), according to some embodiments.

The principles, uses and implementations of the teachings herein may be better understood with reference to the accompanying description and figures. Upon perusal of the description and figures present herein, one skilled in the art will be able to implement the teachings herein without undue effort or experimentation. In the figures, same reference numerals refer to same parts throughout.

In the following description, various aspects of the invention will be described. For the purpose of explanation, specific details are set forth in order to provide a thorough understanding of the invention. However, it will also be apparent to one skilled in the art that the invention may be practiced without specific details being presented herein. Furthermore, well-known features may be omitted or simplified in order not to obscure the invention.

In some embodiments, there are provided computerized systems and methods for generating and using data analysis algorithms and/or AI-based algorithms for optimizing various operating parameters of automated medical devices and/or providing recommendations to the users of automated medical devices and/or predicting clinical conditions (e.g., complications), based on datasets and parameters derived from or related to the operation of the automated medical devices.

In some embodiments, one or more of the generated algorithms may be used prior to the medical procedure to be performed using the automated medical device, e.g., during the planning stage of the procedure. In some embodiments, one or more of the generated algorithms may be used during the medical procedure, e.g., for analyzing in real-time the operation of the medical device, predicting tissue movement, etc. In some embodiments, one or more of the generated algorithms may be used following the medical procedure, e.g., for analyzing the performance of the medical device, analyzing the outcome(s) of the procedure, etc.

In some embodiments, one or more of the generated algorithms may be used to enhance various operating parameters of other medical devices, different from the automated medical device, which may be utilized in the same medical procedure. For example, some algorithms may provide operating recommendations and/or instructions relating to parameters of an imaging system (such as CT, ultrasound, etc.) used in the medical procedure. Providing recommendations and/or controlling the operating parameters of the imaging system may, in some embodiments, allow further enhancement of the performance of the automated medical device.

In some embodiments, one or more of the generated algorithms may be used to enhance various operating parameters of other medical devices, different from the automated medical device, which may be utilized in other medical procedures. Further, one or more of the generated algorithms may be used in procedures carried out manually by a user (e.g., physician). For example, an algorithm which can predict the probability of a medical complication (e.g., pneumothorax) may be used in manually performed medical procedures (e.g., lung biopsy).

Reference is now made to FIG. 1, which schematically illustrates a system 10 for generating and using data-analysis model(s)/algorithm(s), according to some embodiments. As shown in FIG. 1, various datasets 12 are collected from and/or based on the operation of a plurality (N) of automated medical devices (shown as Devices 1, 2, 3, . . . n), as well as on other related datasets (such as, patient related datasets, administrative related datasets, etc.). The datasets 12 may be used for generating a variety of specialized data-analysis algorithms/models 14, which may utilize artificial intelligence tools, as detailed below. The generated models/algorithms may then be used for providing recommendations, operating instructions, enhancements, predictions and/or alerts 16, for example, to enhance and improve subsequent medical procedures 18. In some embodiments, the generation of the models/algorithms is facilitated using various datasets and/or various parameters related to or derived from the datasets, to create one or more training sets, based upon which, the models/algorithms are created, as described in more detail hereinbelow.

In some embodiments, the automated medical device is used for insertion and steering of a medical instrument in a subject's body. In some embodiments, the steering of the medical instrument within the body of a subject may be based on planning and real-time updating the trajectory (2D and/or 3D) of the medical instrument (e.g., of the tip thereof) within the body of the subject, to facilitate the safe and accurate reaching of the tip to an internal target region within the subject's body, by the most efficient and safe route.

Figure 2A:
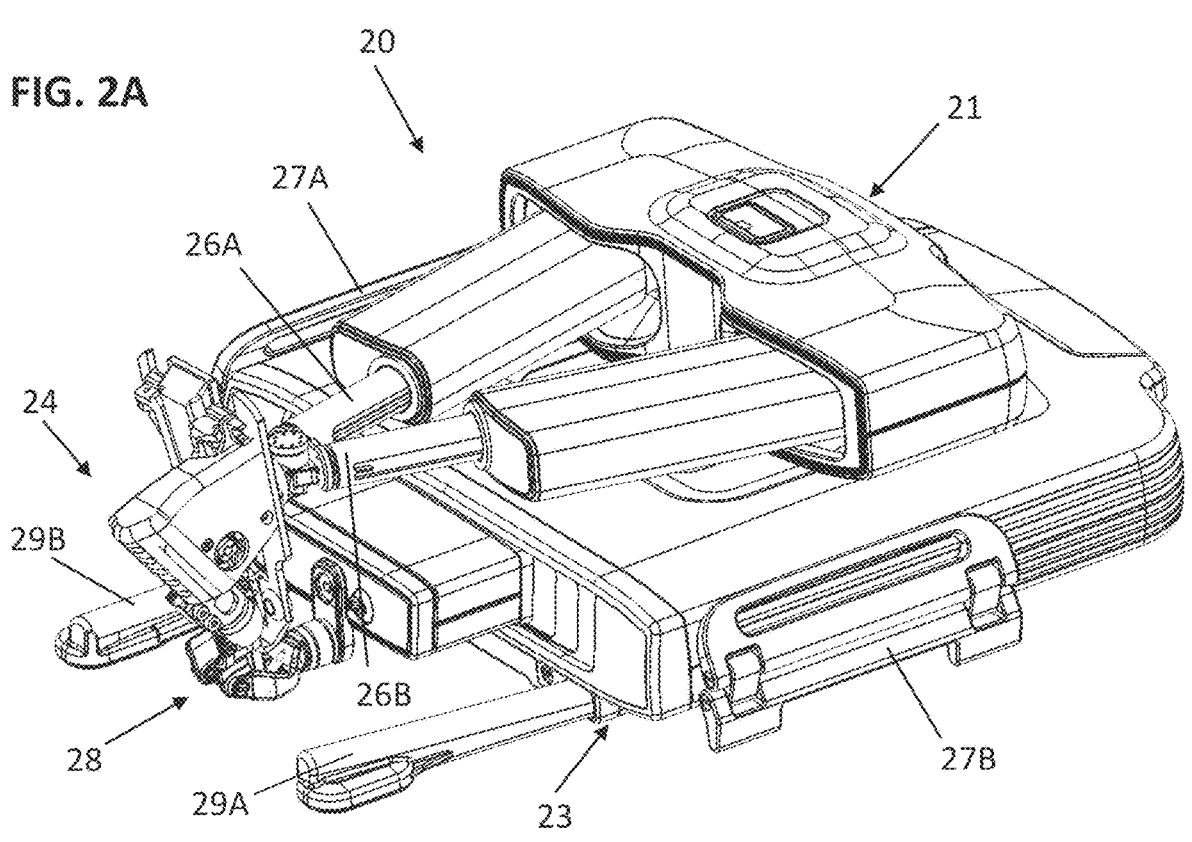
FIGS. 2A-2B show perspective views of an exemplary device (FIG. 2A) and an exemplary console (FIG. 2B) of a system for inserting a medical instrument toward an internal target, according to some embodiments.

Reference is now made to FIG. 2A, which shows an exemplary automated medical device for inserting a medical instrument in a body of a subject, according to some embodiments. As shown in FIG. 2A, the device 20 may include a housing (also referred to as "cover") 21 accommodating therein at least a portion of the steering mechanism. The steering mechanism may include at least one moveable platform (not shown) and at least two moveable arms 26A and 26B, configured to allow or control movement of an end effector (also referred to as "control head") 24, at any one of desired movement angles or axis, as disclosed, for example, in abovementioned U.S. Patent Application Publication No. 2019/290,372. The moveable arms 26A and 26B may be configured as piston mechanisms. To the end 28 of control head 24, a suitable medical instrument (not shown) may be connected, either directly or by means of a suitable insertion module, such as the insertion module disclosed in co-owned U.S. Patent Application Publication No. 2017/258,489, which is incorporated herein by reference in its entirety. The medical instrument may be any suitable instrument capable of being inserted and steered within the body of the subject, to reach a designated target, wherein the control of the operation and movement of the medical instrument is effected by the control head 24. The control head 24 may include a driving mechanism (also referred to as "insertion mechanism") configured to advance the medical instrument toward the target in the patient's body. The control head 24 may be controlled by a suitable control system, as detailed herein.

According to some embodiments, the medical instrument may be selected from, but not limited to: a needle, probe (e.g., an ablation probe), port, introducer, catheter (such as a drainage needle catheter), cannula, surgical tool, fluid delivery tool, or any other suitable insertable tool configured to be inserted into a subject's body for diagnostic and/or therapeutic purposes. In some embodiments, the medical tool includes a tip at the distal end thereof (i.e., the end which is inserted into the subject's body).

In some embodiments, the device 20 may have a plurality of degrees of freedom (DOF) in operating and controlling the movement the of the medical instrument along one or more axis. For example, the device may have up to six degrees of freedom. For example, the device may have at least five degrees of freedom. For example, the device may have five degrees of freedom, including two linear translation DOF (in a first axis), a longitudinal linear translation DOF (in a second axis substantially perpendicular to the first axis) and two rotational DOF. For example, the device may have forward-backward and left-right linear translations facilitated by two moveable platforms, front-back and left-right rotations facilitated by two moveable arms (e.g., piston mechanism), and longitudinal translation toward the subject's body facilitated by the insertion mechanism. In some embodiments, the control system (i.e., processor and/or controller) may be capable of controlling the steering mechanism (including the moveable platforms and the moveable arms) and the insertion mechanism simultaneously, thus enabling non-linear steering of the medical instrument, i.e., enabling the medical instrument to reach the target by following a non-linear trajectory. In some embodiments, the device may have six degrees of freedom, including the five degrees of freedom described above and, in addition, rotation of the medical instrument about its longitudinal axis. In some embodiments, rotation of the medical instrument about its longitudinal axis may be facilitated by a designated rotation mechanism. In some embodiments, the control system (i.e., processor and/or controller) may be capable of controlling the steering mechanism, the insertion mechanism and the rotation mechanism simultaneously.

In some embodiments, the device may further include a base 23, which allows positioning of the device on or in close proximity to the subject's body. In some embodiments, the device may be configured for attachment to the subject's body either directly or via a suitable mounting surface, such as the mounting base disclosed in co-owned U.S. Patent Application Publication No. 2019/125,397, or the attachment apparatus disclosed in co-owned International Patent Application Publication No. WO 2019/234,748, both of which are incorporated herein by reference in their entireties. Attachment of the device 20 to the mounting surface may be carried out using dedicated latches, such as latches 27A and 27B. In some embodiments, the device may be couplable to a dedicated arm or base which is secured to the patient's bed, to a cart positioned adjacent the patient's bed or to an imaging device (if used), and held on the subject's body or in close proximity thereto, as described, for example, in abovementioned U.S. Pat. No. 10,507,067 and in U.S. Pat. No. 10,639,107, which is incorporated herein by reference in its entirety.

In some embodiments, the device may include electronic components and motors (not shown) allowing the controlled operation of the device 20 in inserting and steering the medical instrument. In some exemplary embodiments, the device may include one or more Printed Circuit Board (PCB) (not shown) and electrical cables/wires (not shown) to provide electrical connection between a controller (not shown) and the motors of the device and other electronic components thereof. In some embodiments, the controller may be embedded, at least in part, within device 20. In some embodiments, the controller may be a separate component. In some embodiments, the device 20 may include a power supply (e.g., one or more batteries) (not shown). In some embodiments, the device 20 may be configured to communicate wirelessly with the controller and/or processor. In some embodiments, device 20 may include one or more sensors, such as, but not limited to: a force sensor, an acceleration sensor and/or a radiation sensor (not shown). Use of sensor/s for sensing parameters associated with the interaction between a medical instrument and a bodily tissue, e.g., a force sensor, and utilizing the sensor data for monitoring and/or guiding the insertion of the instrument and/or for initiating imaging, is described, for example, in co-owned U.S. Patent Application Publication No. 2018/250,078, which is incorporated herein by reference in its entirety.

In some embodiments, the housing 21 is configured to cover and protect, at least partially, the mechanical and/or electronic components of device 20 from being damaged or otherwise compromised. In some embodiments, the housing 21 may include at least one adjustable cover, and it may be configured to protect the device from being soiled by dirt, as well as by blood and/or other bodily fluids, thus preventing/minimizing the risk of cross-contamination between patients, as disclosed, for example, in co-owned International Patent Application No. PCT/IL2020/051220, which is incorporated herein by reference in its entirety.

In some embodiments, the device may further include registration elements disposed at specific locations on the device 20, such as registration elements 29A and 29B, for registration of the device to the image space, in image-guided procedures. In some embodiments, registration elements may be disposed on the mounting surface to which device 20 may be coupled, either instead or in addition to registration elements disposed on device 20. In some embodiments, the device may include a CCD/CMOS camera mounted on the device and/or on the device's frame and/or as a separate apparatus, allowing the collection of visual images and/or videos of the patient's body during a medical procedure.

In some embodiments, the medical instrument is configured to be removably coupleable to the device 20, such that the device can be used repeatedly with new medical instruments. In some embodiments, the medical instruments are disposable. In some embodiments, the medical instruments are reusable.

In some embodiments, device 20 is part of a system for inserting and steering a medical instrument in a subject's body based on a preplanned and, optionally, real-time updated trajectory, as disclosed, for example, in abovementioned co-owned International Application No. PCT/IL2020/051219. In some embodiments, the system may include the steering and insertion device 20, as disclosed herein, and a control unit (or—"workstation" or "console") configured to allow control of the operating parameters of device 20. In some embodiments, the user may operate the device 20 using a pedal or an activation button. In some embodiments, the system may include a remote control unit, which may enable the user to activate the device 20 from a remote location, such as the control room adjacent the procedure room (e.g., CT suite), a different location at the medical facility or even a location outside the medical facility. In some embodiments, the user may operate the device using voice commands.

Figure 2B:
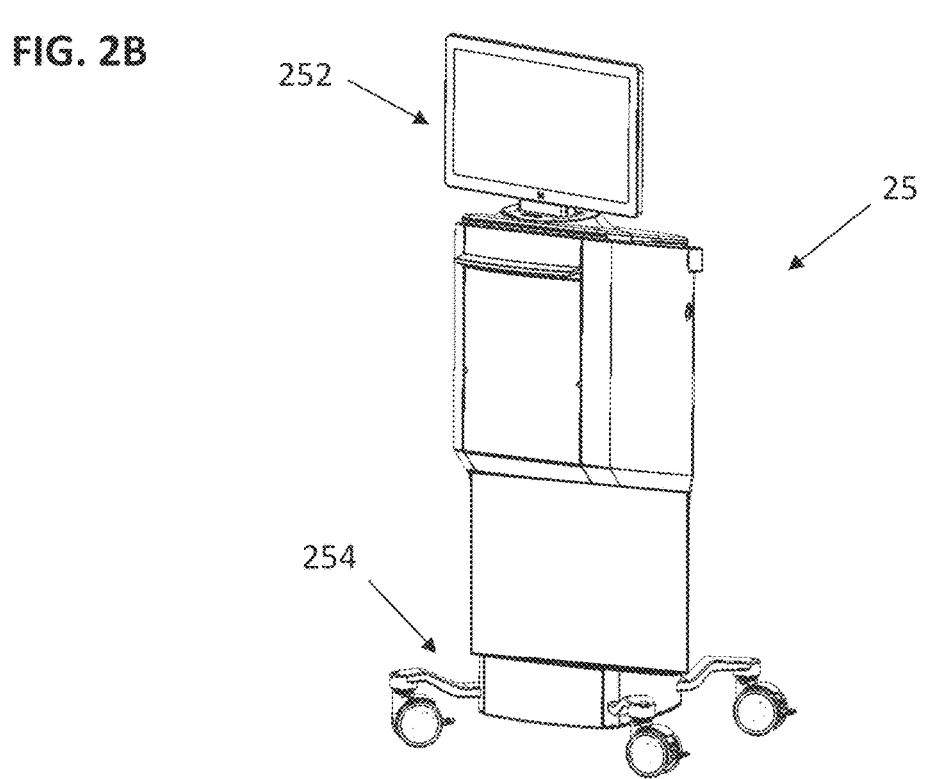

Reference is now made to FIG. 2B, which shows an exemplary workstation (also referred to as "console") 25 of an insertion system, according to some embodiments. The workstation 25 may include a display 252 and a user interface (not shown). In some embodiments, the user interface may be in the form of buttons, switches, keys, keyboard, computer mouse, joystick, touch-sensitive screen, and the like. The monitor and user interface may be two separate components, or they may form together a single component (e.g., in the form of a touch-screen). The workstation 25 may include one or more suitable processors (for example, in the form of a PC) and one or more suitable controllers, configured to physically and/or functionally interact with device 20, to determine and control the operation thereof. The one or more processors may be implemented in the form of a computer (such as a workstation, a server, a PC, a laptop, a tablet, a smartphone or any other processor-based device). In some embodiments, the workstation 25 may be portable (e.g., by having or being placed on a movable platform 254).

In some embodiments, the one or more processors may be configured to perform one or more of: determine (plan) a trajectory for the medical instrument to reach the target; update the trajectory in real-time, for example due to movement of the target from its initial identified position as a result of the advancement of the medical instrument within the patient's body; present the planned and/or updated trajectory on the monitor 252; control the movement (insertion/steering) of the medical instrument based on the planned and/or updated trajectory by providing executable instructions (directly or via the one or more controllers) to the device; determine the actual location of the tip of medical instrument by performing required compensation calculations; receive, process and visualize on the monitor images or image-views created from a set of images (between which the user may be able to scroll), operating parameters and the like; or any combination thereof.

In some embodiments, the use of AI-based models (e.g., machine-learning and/or deep-learning based models) requires a "training" stage in which collected data is used to create (train) models. The generated (trained) models may later be used for "inference" to obtain specific insights, predictions and/or recommendations when applied to new data during the clinical procedure or at any later time.

In some embodiments, the insertion system and the system creating (training) the algorithms/models may be separate systems (i.e., each of the systems includes a different set of processors, memory modules, etc.). In some embodiments, the insertion system and the system creating the algorithms/models may be the same system. In some embodiments, the insertion system and the system creating the algorithms/models may share one or more resources (such as, processors, memory modules, GUI, and the like). In some embodiments, the insertion system and the system creating the algorithms/models may be physically and/or functionally associated. Each possibility is a separate embodiment.

In some embodiments, the insertion system and the system utilizing the algorithms/models for inference may be separate systems (i.e., each of the systems includes a different set of processors, memory modules, etc.). In some embodiments, the insertion system and the system utilizing the algorithms/models for inference may be the same system. In some embodiments, the insertion system and the system utilizing the algorithms/models for inference may share one or more resources (such as, processors, memory modules, GUI, and the like). In some embodiments, the insertion system and the system utilizing the algorithms/models for inference may be physically and/or functionally associated. Each possibility is a separate embodiment.

In some embodiments, the device may be configured to operate in conjunction with an imaging system, including, but not limited to: X-Ray, CT, cone beam CT, CT fluoroscopy, MRI, ultrasound, or any other suitable imaging modality. In some embodiments, the steering of the medical instrument based on a planned and, optionally, real-time updated 2D or 3D trajectory of the tip of the medical instrument, may be image-guided.

According to some embodiments, during the operation of the automated medical device, various types of data may be generated, accumulated and/or collected, for further use and/or manipulation, as detailed below. In some embodiments, the data may be divided into various types/sets of data, including, for example, data related to operating parameters of the device, data related to clinical procedures, data related to the treated patient, data related to administrative information, and the like, or any combination thereof.

In some embodiments, such collected datasets may be collected from one or more (i.e., a plurality) of automated medical devices, operating under various circumstances (for example, different procedures, different medical instruments, different patients, different locations and operating staff, etc.), to thereby generate a large data base ("big data"), that can be used, utilizing suitable data analysis tools and/or AI-based tools to ultimately generate models or algorithms that allow performance enhancements, automatic control or affecting control (i.e., by providing recommendations), of the medical devices. Thus, by generating such advantageous and specialized models or algorithms, enhanced control and/or operation of the medical device may be achieved.

Figure 3:
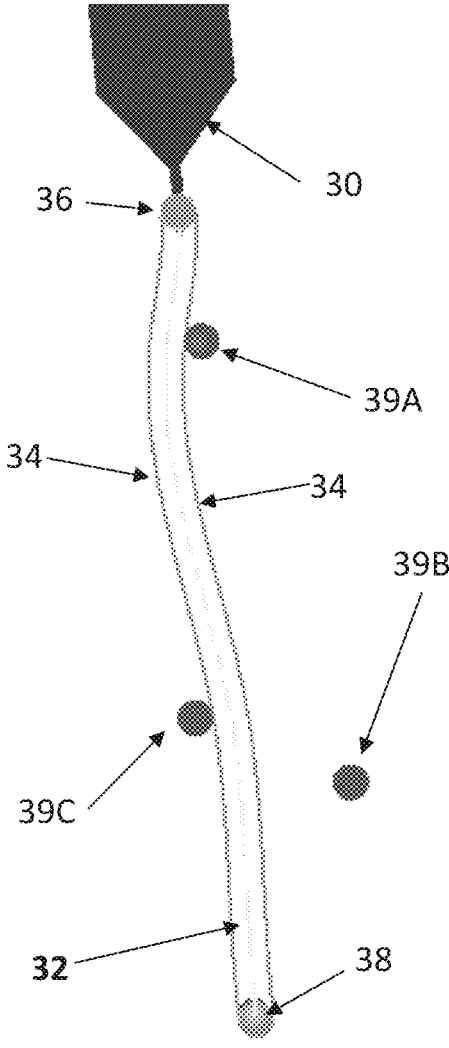
FIG. 3 shows an exemplary trajectory for a medical instrument to reach an internal target within the body of the subject, according to some embodiments.

Reference is now made to FIG. 3, which schematically shows a trajectory planned using a processor, such as the processor(s) of the insertion system described in FIG. 2B, for delivering a medical instrument to an internal target within the body of the subject, using an automated medical device, such as the automated device of FIG. 2A. In some embodiments, the planned trajectory may be linear or substantially linear. In some embodiments, and as shown in FIG. 3, the trajectory may be non-linear trajectory having any suitable/acceptable degree of curvature.

In some embodiments, the one or more processors may calculate a planned trajectory for the medical instrument to reach the target. The planning of the trajectory and the controlled steering of the instrument according to the planned trajectory may be based on a model of the medical instrument as a flexible beam having a plurality of virtual springs connected laterally thereto to simulate lateral forces exerted by the tissue on the instrument, thereby calculating the trajectory through the tissue on the basis of the influence of the plurality of virtual springs on the instrument, and utilizing an inverse kinematics solution applied to the virtual springs model to calculate the required motion to be imparted to the instrument to follow the planned trajectory. The processor may then provide motion commands to the automated device, for example via a controller. In some embodiments, steering of the medical instrument may be controlled in a closed-loop manner, whereby the processor generates motion commands to the automated device and receives feedback regarding the real-time location of the medical instrument (e.g., the tip thereof), which is then used for real-time trajectory corrections, as disclosed, for example, in abovementioned U.S. Pat. No. 8,348,861. For example, if the instrument has deviated from the planned trajectory, the processor may calculate the motion to be applied to the robot to reduce the deviation. The real-time location of the medical instrument and/or the corrections may be calculated and/or applied using data-analysis models/algorithms. In some embodiments, certain deviations of the medical instrument from the planned trajectory, for example deviations which exceed a predetermined threshold, may require recalculation of the trajectory for the remainder of the procedure, as described in further detail hereinbelow.

As shown in FIG. 3, a trajectory 32 is planned between an entry point 36 and an internal target 38. The planning of the trajectory 32 may take into account various variables, including, but not limited to: the type of the medical instrument to be used and its characteristics, the dimensions of the medical instrument (e.g., length, gauge), the type of imaging modality (such as, CT, CBCT, MRI, X-Ray, CT fluoroscopy, ultrasound and the like), the tissues through which the medical instrument is to be inserted, the location of the target, the size of the target, the insertion point, the angle of insertion (relative to one or more axis), milestone points ("secondary targets" through which the medical instrument should pass) and the like, or any combination thereof. In some embodiments, at least one of the milestone points may be a pivot point, i.e., a predefined point along the trajectory in which the deflection of the medical instrument is prevented or minimized, to maintain minimal pressure on the tissue (even if this results in a larger deflection of the instrument in other parts of the trajectory). In some embodiments, the planned trajectory is an optimal trajectory based on one or more of these parameters. Further taken into account in determining the trajectory may be various obstacles 39A-39C, which may be identified along the path and which should be avoided, to prevent damage to the neighboring tissues and/or to the medical instrument. According to some embodiments, safety margins 34 may be marked along the planned trajectory 32, to ensure a minimal distance between the trajectory 32 and potential obstacles en route. The width of the safety margins may be symmetrical in relation to the trajectory 32. The width of the safety margins may be asymmetrical in relation to the trajectory 32. According to some embodiments, the width of the safety margins 34 may be preprogrammed. According to some embodiments, the width of the safety margins may be automatically set, or recommended to the user, by the processor, based on data obtained from previous procedures using a data analysis algorithm. According to some embodiments, the width of the safety margins 34 may be determined and/or adjusted by the user. Further shown in FIG. 3 is an end of a control head 30 of the exemplary automated insertion device, to which the medical instrument (not shown in FIG. 3) is coupled, as virtually displayed on the monitor, to indicate its position and orientation.

The trajectory 32 shown in FIG. 3 is a planar trajectory (i.e., two dimensional). In some embodiments, steering of the instrument is carried out according to a planner trajectory, for example trajectory 32. In some embodiments, the calculated planner trajectory may be superpositioned with one or more additional planner trajectories, to form a three-dimensional (3D) trajectory. Such additional planner trajectories may be planned on one or more different planes, which may be perpendicular to the plane of the first planner trajectory (e.g., trajectory 32) or otherwise angled relative thereto. According to some embodiments, the 3D trajectory may include any type of trajectory, including a linear trajectory or a non-linear trajectory.

According to some embodiments, the steering of the medical instrument is carried out in a 3D space, wherein the steering instructions are determined on each of the planes of the superpositioned planner trajectories, and are then superpositioned to form the steering in the three-dimensional space. The data/parameters/values thus obtained during the steering of the medical instrument using the automated device can be used as data/parameters/values for the generation/training and/or utilization/inference of the data-analysis model(s)/algorithm(s).

Reference is now made to FIGS. 4A-4D, which show planning of an exemplary trajectory for inserting and steering a medical instrument toward a target, according to some embodiments. The exemplary trajectory may be planned using a processor, such as the processor(s) of the insertion system described in FIG. 2B, and the insertion and steering of the medical instrument toward the target according to the planned trajectory may be executed using an automated insertion device, such as the automated device of FIG. 2A.

Figure 4A:
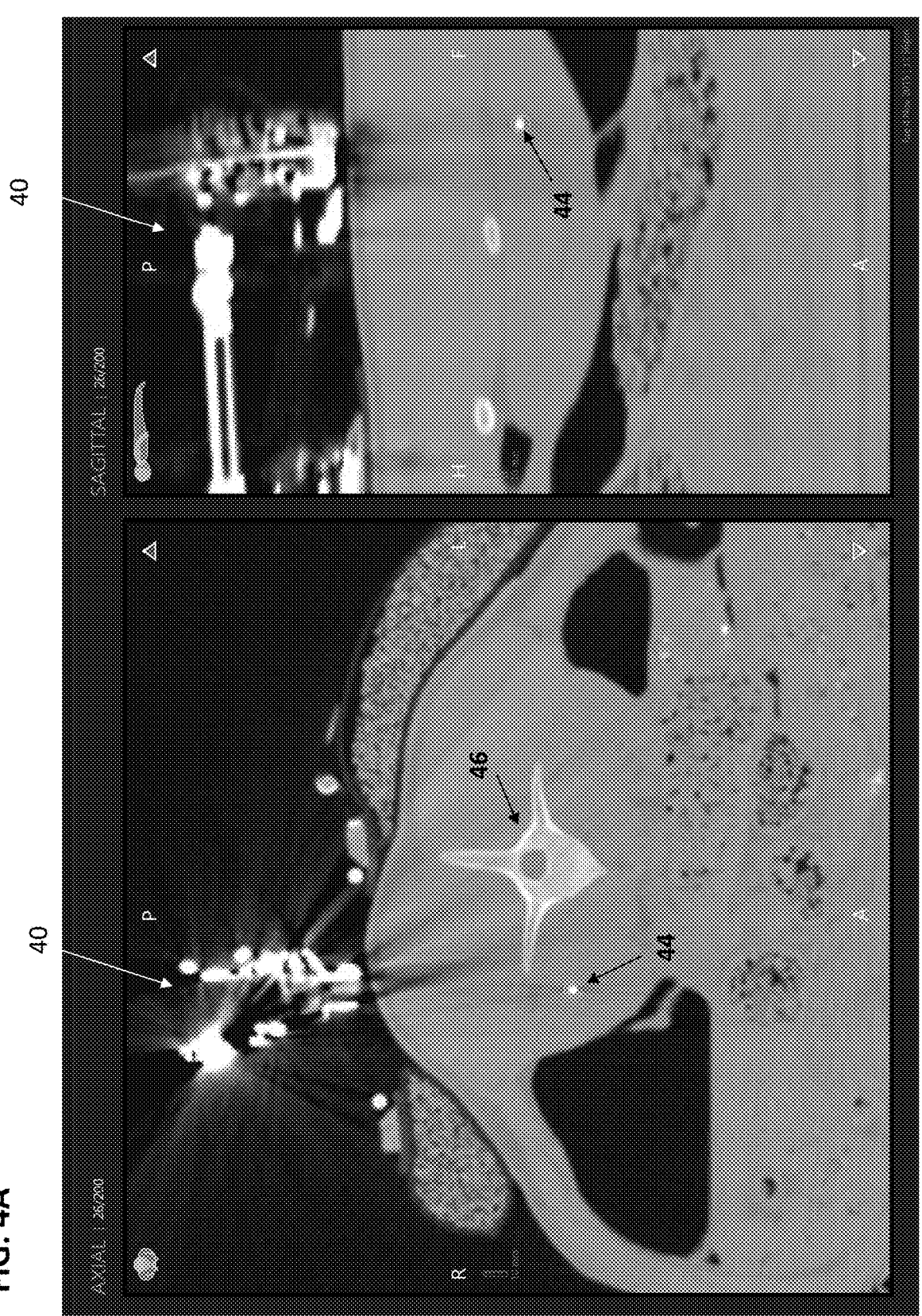
FIGS. 4A-4D show planning of an exemplary trajectory for inserting and steering a medical instrument toward a target, on CT images, according to some embodiments.
Figure 4B:
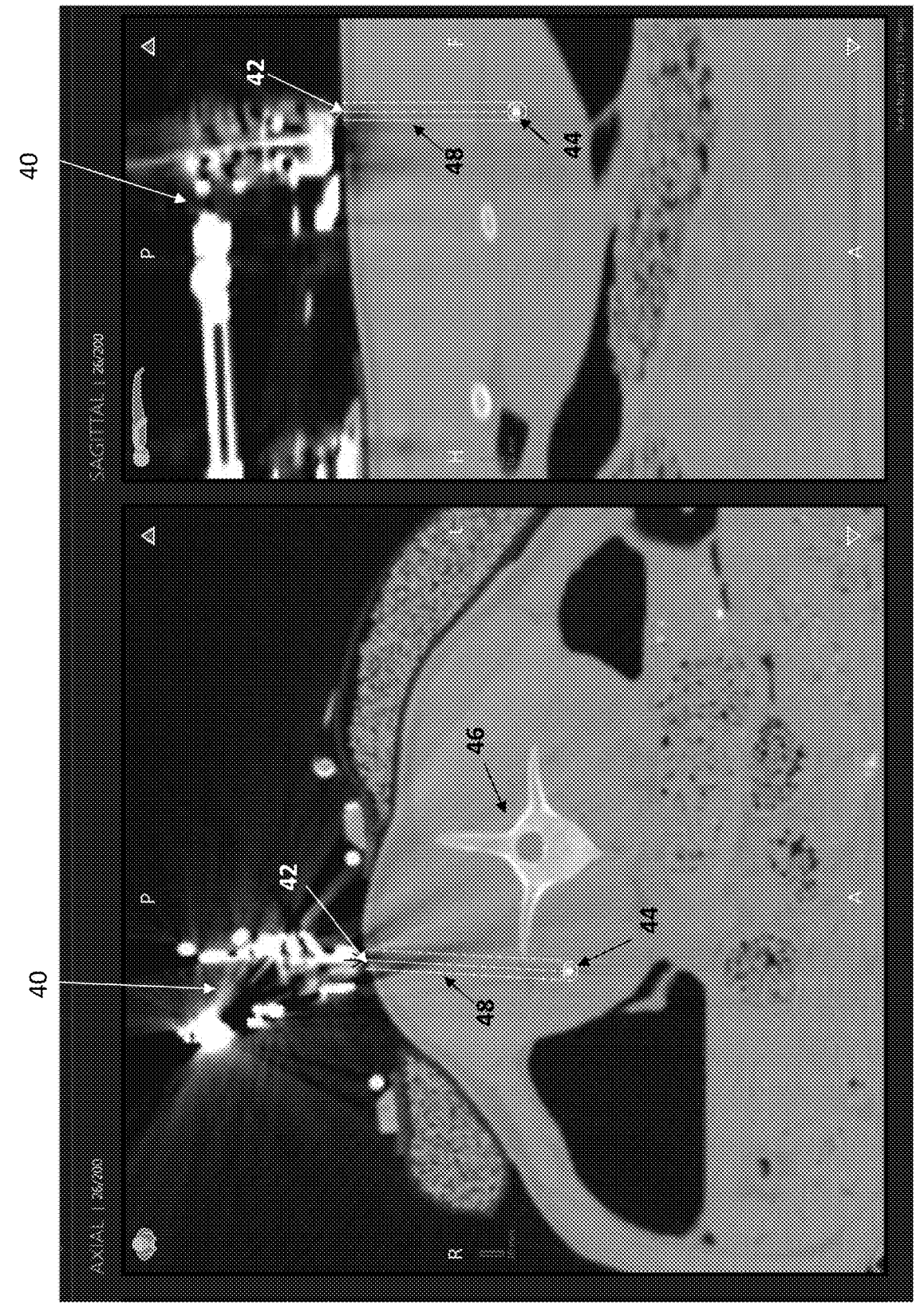
Figure 4C:
Figure 4D:
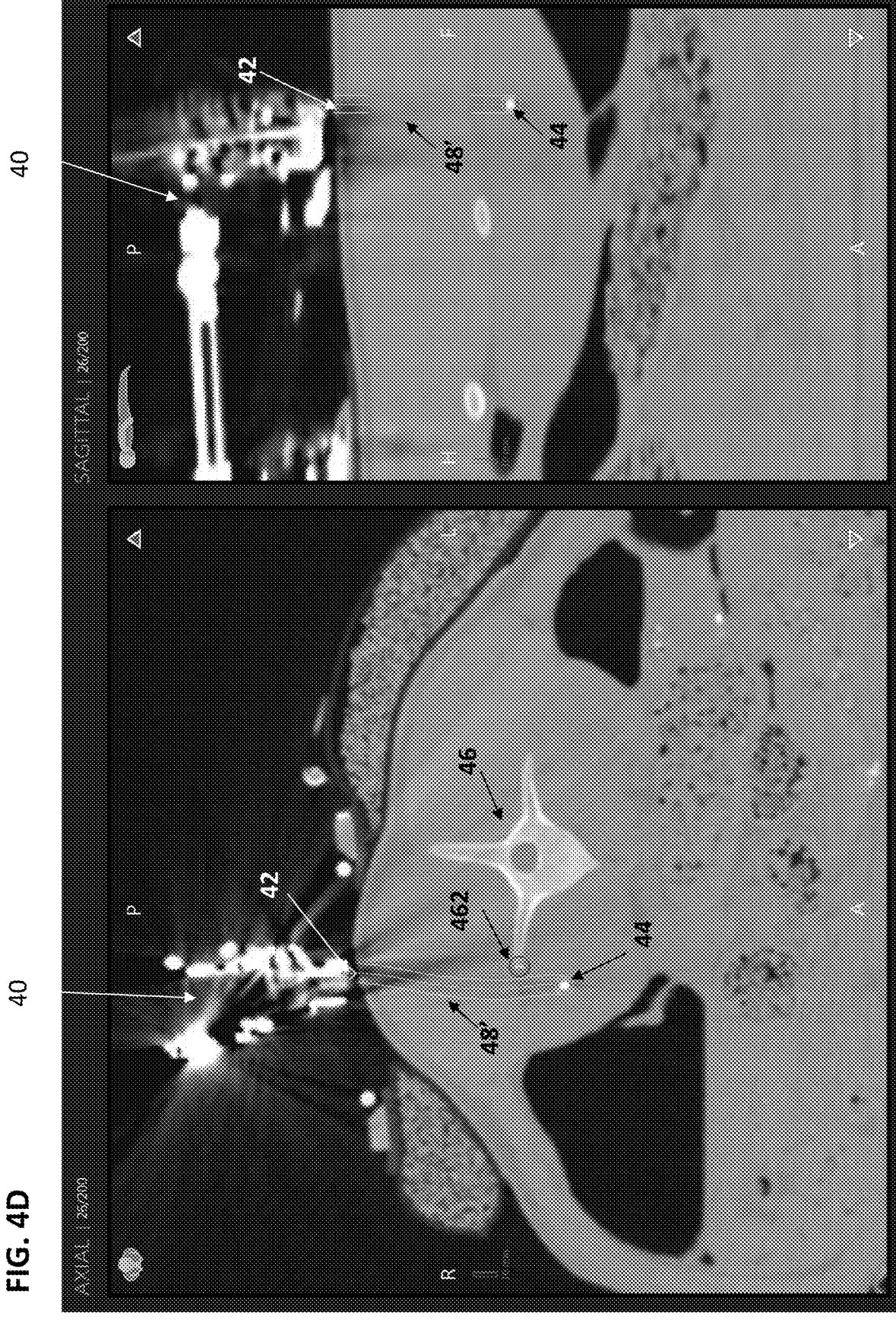

The planning in FIGS. 4A-4D is shown on CT image-views, however it can be appreciated that the planning can be carried out similarly on images obtained from other imaging systems, such as ultrasound, MRI and the like. Shown in FIG. 4A are CT image-views of a subject, depicting at the left-hand panel an axial plane view and on the right-hand panel a sagittal plane view. Also indicated in the figure is an internal target 44 and an automated insertion device 40. Further indicated is a vertebra 46. In FIG. 4B, which shows the CT image-views of FIG. 4A, the insertion point 42 is indicated. Consequently, according to some embodiments, a linear trajectory 48 between the insertion point 42 and the internal target 44 may be calculated and displayed on each of the two views (for example, axial plane view and sagittal plane view). Typically, a linear trajectory is preferred, thus, if the displayed linear trajectory does not pass in close proximity to any potential obstacles, then the linear trajectory is determined as the planned trajectory for the insertion procedure. In FIG. 4C, a transverse process 462 of vertebra 46 is detected in close proximity to the calculated linear trajectory, and is identified and marked, in this example on the axial plane view, to allow considering the obstacle when planning the trajectory for the procedure. In FIG. 4D, the trajectory is re-calculated, so as to allow the instrument to avoid contacting the obstacle 462, resulting in a non-linear trajectory 48'. According to some embodiments, the planned trajectory may not be calculated until potential obstacles are marked on the image-view/s, either manually or automatically, until the user confirms that there are no potential obstacles and/or until the user manually initiates trajectory calculation. In such embodiments, if there are obstacles which necessitate a non-linear trajectory, an interim linear trajectory, similar to linear trajectory 48 of FIG. 4B, may not be calculated and/or displayed. According to some embodiments, a maximal allowable curvature level may be pre-set for the calculation of the non-linear trajectory. The maximal curvature threshold may depend, for example, on the trajectory parameters (e.g., distance between the entry point and the target) and on the type of instrument intended to be used in the procedure and its characteristics (for example, type, diameter (gauge), and the like). As further detailed below, the planned trajectory may be updated in real-time based on the real-time position of the medical instrument (for example, the tip thereof) and/or the real-time position of the target and/or the real-time positions of obstacle/s.

According to some embodiments, the target 44, insertion point 42 and, optionally, obstacle/s, such as transverse process 462, are marked manually by the user. According to other embodiments, the processor of the insertion system (or of a separate system) may be configured to identify and mark at least one of the target, the insertion point and the obstacle/s, and the user may, optionally, be prompted to confirm or adjust the processor's proposed markings. In such embodiments, the target and/or obstacle/s may be identified using known image processing techniques and/or data-analysis models/algorithms, based on data obtained from previous procedures. The insertion point may be suggested based solely on the obtained images, or, alternatively or additionally, on data obtained from previous procedures using data-analysis models/algorithms.

According to some embodiments, the trajectory may be calculated based solely on the obtained images and the marked locations of the entry point, target (and, optionally, obstacle/s). According to other embodiments, the calculation of the trajectory may be based also on data obtained from previous procedures, using data-analysis models/algorithms. According to some embodiments, once the planned trajectory has been determined, checkpoints along the trajectory may be set. The checkpoints may be manually set by the user, or they may be automatically set or recommended by the processor, as described in further detail hereinbelow.

It can be appreciated that although axial and sagittal views are shown in FIGS. 4A-4D, views pertaining to different planes or orientations (e.g., coronal, pseudo axial, pseudo sagittal, pseudo coronal, etc.) or additionally generated views (e.g., trajectory view, tool view, 3D view, etc.), may be used in order to perform and/or display the trajectory planning.

Reference is now made to FIGS. 5A-5D, which show schematic illustrations of real-time updating of a trajectory for inserting and steering a medical instrument toward a target, according to some embodiments. The trajectory may be updated using a processor, such as the processor(s) of the insertion system described in FIG. 2B, and the insertion and steering of the medical instrument toward the target according to the planned and updated trajectories may be executed using an automated insertion device, such as an automated device 50. In some embodiments, the automated device 50 may be body-mountable, for example, as shown in FIGS. 5A-5D, the device 50 may be configured for attachment to a subject's body using an attachment apparatus 52, such as the attachment apparatus described in abovementioned co-owned International Patent Application Publication No. WO 2019/234,748.

According to some embodiments, once the planned trajectory has been determined, checkpoints along the trajectory may be set. Checkpoints may be used to pause the insertion of the medical instrument and initiate imaging of the region of interest, to verify the position of the instrument (specifically, in order to verify that the instrument (e.g., the tip thereof) follows the planned trajectory), to monitor the location of the marked obstacles and/or identify previously unmarked obstacles along the trajectory, and to verify the target's position, such that recalculation of the trajectory may be initiated, if the user chooses to do so, before advancing the instrument to the next checkpoint/the target. The checkpoints may be manually set by the user, or they may be automatically set or recommended by the processor, as described in further detail hereinbelow. According to some embodiments, the checkpoints may be positioned at a spatial-pattern, a temporal-pattern, or both. According to some embodiments, the checkpoints may be reached at predetermined time intervals, for example, every 2-5 seconds. According to some embodiments, the checkpoints may be spaced apart, including the first checkpoint from the entry point and the last checkpoint from the target organ and/or target point, at an essentially similar distance along the trajectory, for example every 20-50 mm. According to some embodiments, upper and/or lower interval thresholds between checkpoints may be predetermined. For example, the checkpoints may be automatically set by the processor at default 20 mm intervals, and the user can then adjust the distance between each two checkpoints (or between the entry point and the first checkpoint and/or between the last checkpoint and the target) such that the maximal distance between them is 30 mm and/or the minimal distance between them is 3 mm, for example.

The trade-off of utilizing many checkpoints is prolonged procedure time, as well as repeated exposure to radiation. On the other hand, too little checkpoints may affect the accuracy and safety of the medical procedure. In the example shown in FIGS. 5A-5D, three checkpoints have been set along the trajectory.

Figure 5A:
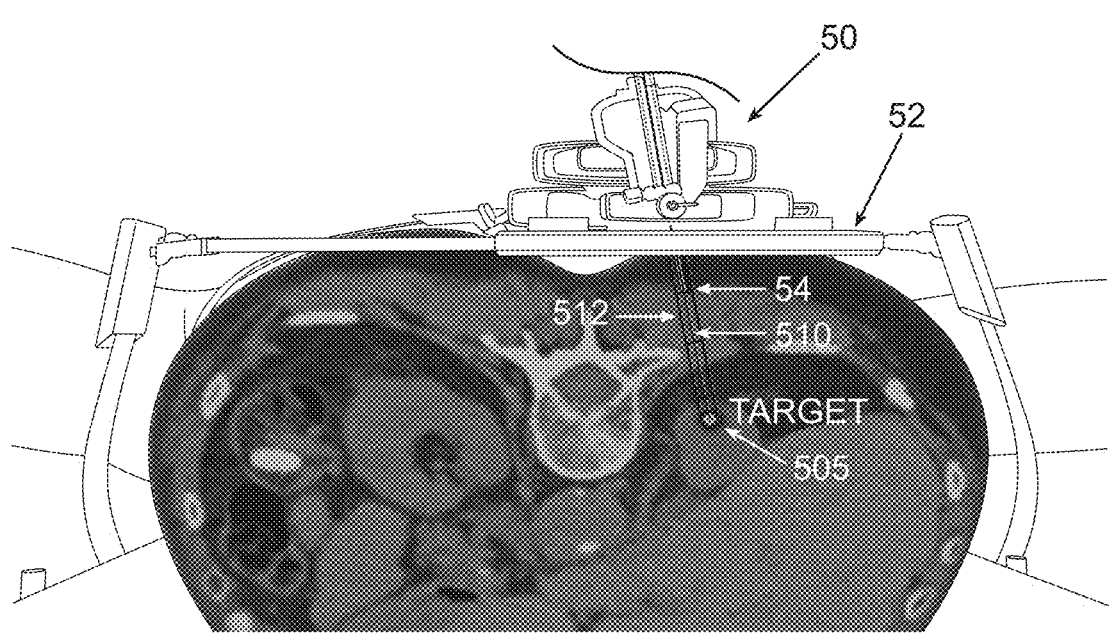
FIGS. 5A-5D show schematic illustrations of real-time updating of a trajectory for inserting and steering a medical instrument toward a target, according to some embodiments.
Figure 5B:
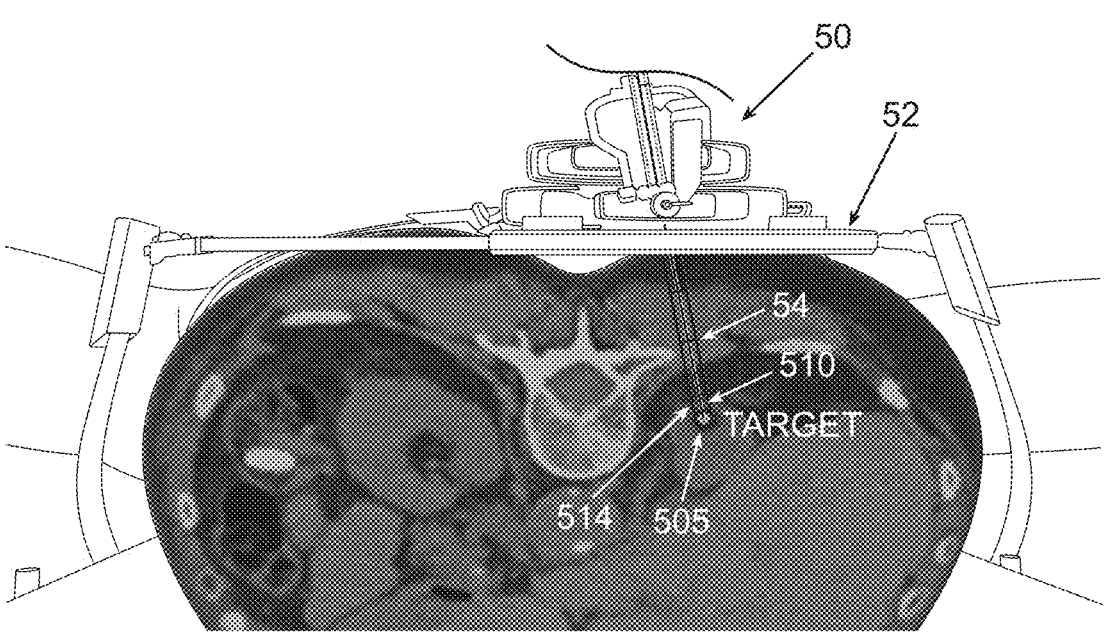

FIG. 5A shows a medical instrument 54 being inserted toward a target 505 in the subject's body and reaching the first checkpoint 512, according to a preplanned trajectory 510. In some embodiments, the preplanned trajectory 510 is a linear or substantially linear trajectory. FIG. 5B shows the medical instrument 54 being further inserted into the subject's body, reaching the third checkpoint 514 along the planned trajectory 510. As shown in FIG. 5B, the target 505 has moved from its initial position during and as a result of the advancement of the medical instrument within the tissue. In some embodiments, the determination of the real-time location of the target may be performed manually by the user, i.e., the user visually identifies the target in images (continuous or manually or automatically initiated, for example when the instrument reaches a checkpoint), and marks the new target position on the GUI. In some embodiments, the determination of the real-time target location may be performed automatically by a processor using image processing techniques and/or data-analysis algorithm(s). In some embodiments, once it has been determined that the real-time location of the target deviates from its initial location, i.e., that the target has moved, the deviation may be compared to a predetermined threshold to determine if the deviation exceeds the threshold. The threshold may be, for example, a set value or a percentage reflecting a change in a value. The threshold may be determined by the user or it may be determined by the processor, for example using a data-analysis algorithm based on data collected in previous procedures. In some embodiments, if the deviation does not exceed the predetermined threshold, it may be decided, either by the user or automatically by the processor, that the insertion procedure may continue based on the preplanned trajectory. If the deviation exceeds the predetermined threshold, then it may be decided, either by the user or automatically by the processor, that recalculation of the trajectory is required.

According to some embodiments, recalculation of the trajectory may also be required if the instrument deviated from the planned trajectory above a predetermined deviation threshold. In some embodiments, determining the actual real-time location of the instrument may require applying a correction to the determined location of the tip of the medical instrument, to compensate for deviations due to imaging artifacts. The actual location of the tip may be determined based on an instrument position compensation "look-up" table, which corresponds to the imaging modality and the medical instrument used, as disclosed, for example, in abovementioned co-owned International Patent Application No. PCT/IL2020/051219. In some embodiments, if the real-time location of the medical instrument indicates that the instrument has deviated from the planned trajectory, but the deviation does not exceed the predetermined deviation threshold, one or more checkpoints may be added and/or repositioned along the planned trajectory, either manually by the user or automatically by the processor, to direct the instrument back to the planned trajectory. In some embodiments, the processor may prompt the user to add and/or reposition checkpoint/s. In some embodiments, the processor may recommend to the user specific position/s for the new and/or repositioned checkpoints. Such a recommendation may be generated using data-analysis algorithm(s).

According to some embodiments, recalculation of the trajectory may also be required if, for example, an obstacle is identified along the trajectory. Such an obstacle may be an obstacle which was marked (manually or automatically) prior to the calculation of the planned trajectory but tissue movement, e.g., tissue movement resulting from the advancement of the instrument within the tissue, caused the obstacle to move such that it entered the planned path. In some embodiments, the obstacle may be a new obstacle, i.e., an obstacle which was not visible in the image (or set of images) based upon which the planned trajectory was calculated, and became visible during the insertion procedure.

In some embodiments, if the instrument deviated from the planned trajectory (e.g., above a predetermined deviation threshold), a new or repositioned obstacle is identified along the planned trajectory and/or the target has moved (e.g., above a predetermined threshold), the user may be prompted to initiate an update (recalculation) of the trajectory. In some embodiments, recalculation of the trajectory, if required, is executed automatically by the processor and the insertion of the instrument is automatically resumed based on the updated trajectory. In some embodiments, recalculation of the trajectory, if required, is executed automatically by the processor, however the user is prompted to confirm the recalculated trajectory before advancement of the instrument (e.g., to the next checkpoint) according to the updated trajectory can be resumed.

Figure 5C:
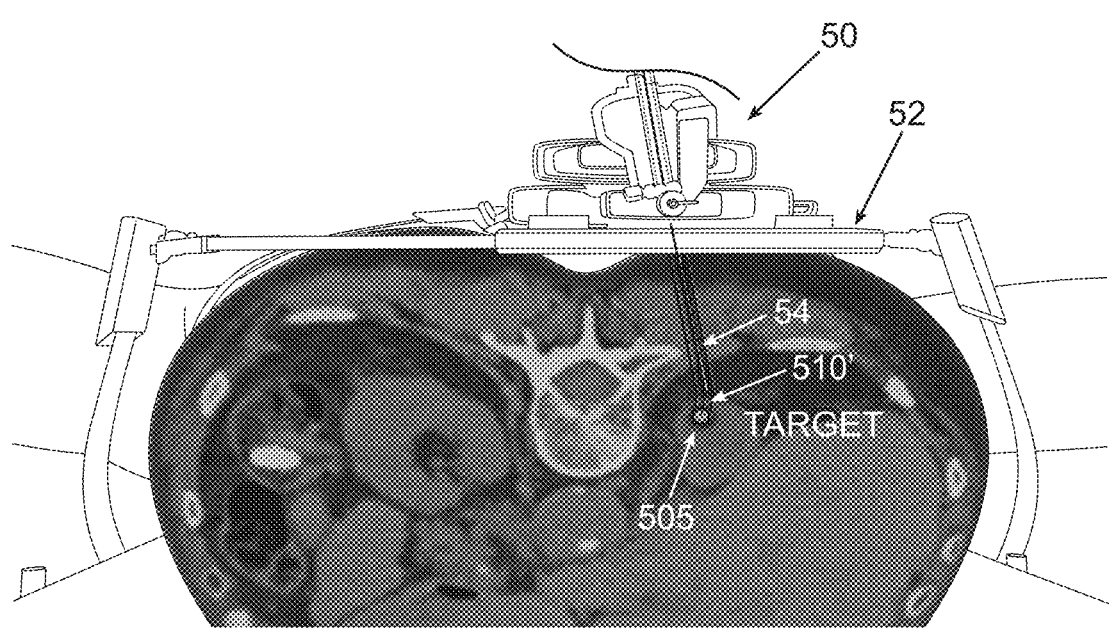
Figure 5D:
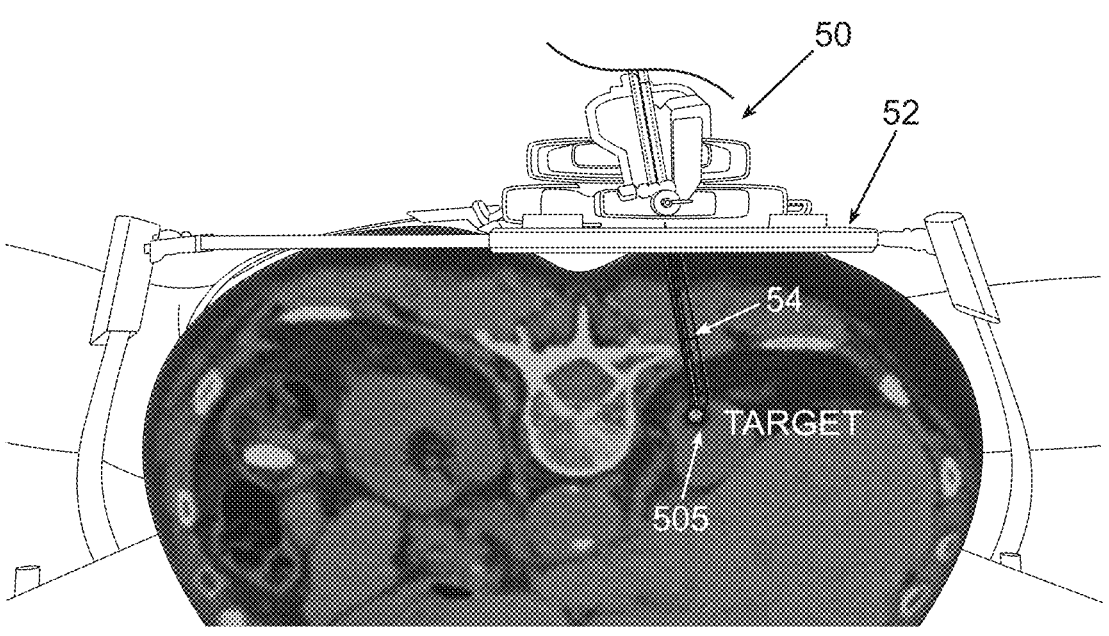

As shown in FIG. 5C, the trajectory has been recalculated based on the new determined location of the target 505, resulting in an updated trajectory 510'. In some embodiments, the updated trajectory 510' is a planner (2D) trajectory. In some embodiments, the updated trajectory 510' is a three-dimensional trajectory, which is calculated by first calculating two or more planner trajectories and then superpositioning the two or more planner trajectories to form the updated 3D trajectory. FIG. 5D shows the medical instrument 54 reaching the target at its new location, after following the updated trajectory 510'. As shown, although the preplanned trajectory 510 was linear, the recalculation of the trajectory due to movement of the target 505, resulted in the medical instrument 54, specifically the tip of the instrument, following a non-linear trajectory to accurately reach the target.

Figure 6:
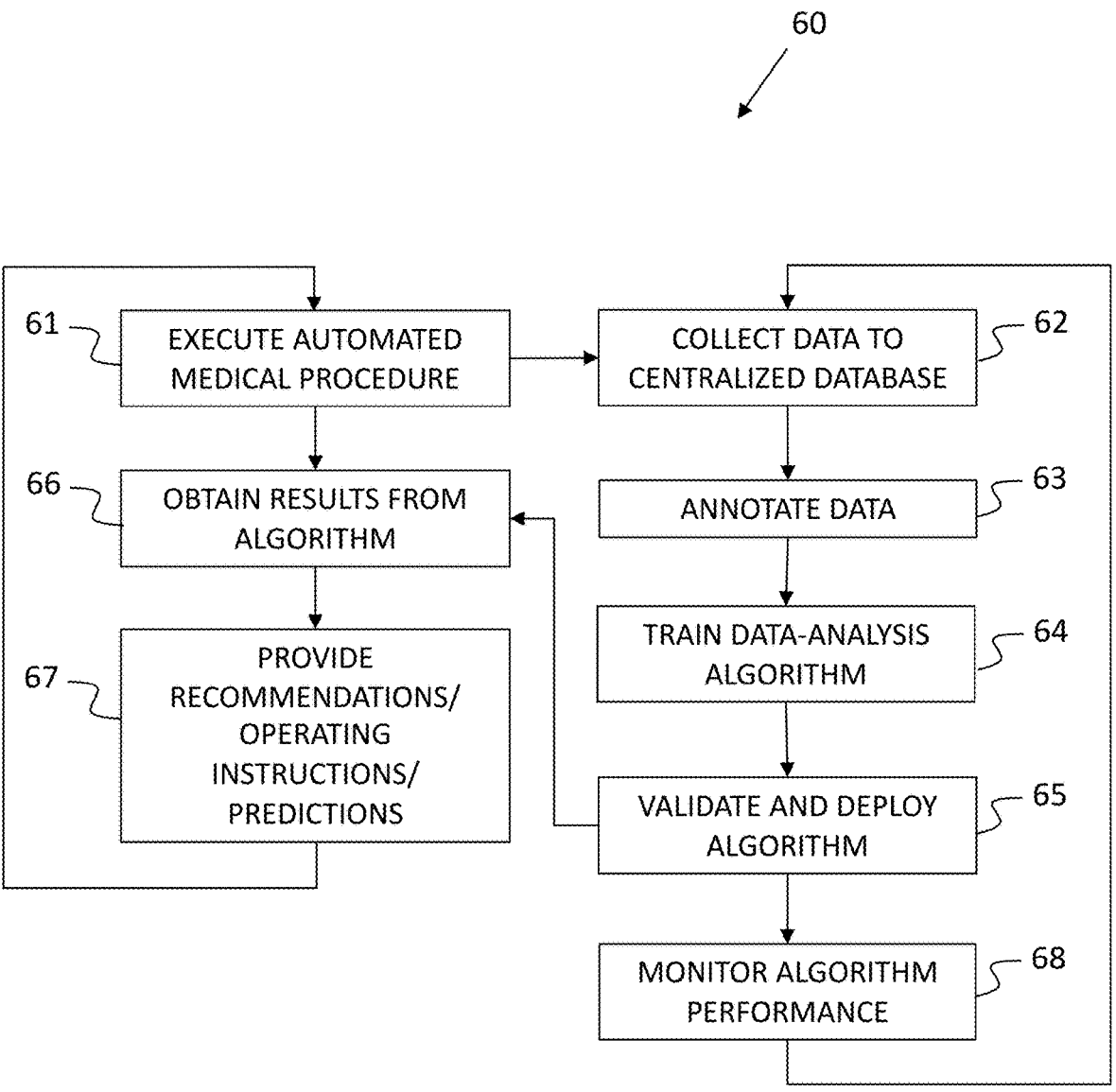
FIG. 6 shows a diagram of a method of generating, deploying and using a data-analysis algorithm, according to some embodiments.

Reference is now made to FIG. 6, which is a diagram 60 of a method of generating, deploying and using a data-analysis algorithm, according to some embodiments. As shown in FIG. 6, at step 61, automated medical procedure(s) are executed using automated medical device(s). Automated medical procedure(s) involve a plurality of datasets related thereto (as further detailed below). For example, some of the datasets directly relate to the operation of the medical device (such as operating parameters), some of the datasets relate to the clinical procedure, some of the datasets relate to the treated patient and some of the datasets relate to administrative related information. In some embodiments, in addition to the datasets related or generated during the medical procedure/s, datasets may be generated during training sessions performed by users on a dedicated simulator system. Such a simulator system may be configured to at least partially simulate a medical procedure, including enabling users to plan the procedure on existing images and then simulating the execution of the procedure according to the procedure plan via a virtual automated medical device and a virtual medical instrument. Next, at step 62, at least some of the generated datasets, values thereof and/or parameters related thereto are collected from the medical procedures and/or simulation sessions and stored in a centralized database. The collected datasets may be split/divided for use as training sets, validation sets and/or testing sets. Then, at step 63, the collected data is annotated, to thereby generate and train the data-analysis algorithm, at stage 64. At step 65, the data-analysis algorithm is validated and deployed. Once deployed, the results from the algorithm are obtained, at step 66, and the results are then used to provide, at stage 67, recommendations/operating instructions/predictions/alerts. Sub sequent medical procedures executed by automated medical devices may implement at least some of the recommendations/operating instructions/predictions/alerts, thereby returning to step 61 and repeating the method. In some instances, the performance of the validated algorithm is monitored, at stage 68, and is further enhanced/improved, based on data stored in the centralized database and/or on newly acquired data.

According to some embodiments, the various obtained datasets may be used for the training, construction and/or validation of the algorithm. In some embodiments, the datasets may be selected from, but not limited to: medical device related dataset, clinical procedures related dataset, patient related dataset, administrative-related dataset, and the like, or any combination thereof.

According to some exemplary embodiments, the medical device related dataset may include such data parameters or values as, but not limited to: procedure steps timing, overall procedure time, overall steering time (of the medical instrument), entry point of the medical instrument, target point/regions, target updates (for example, updating real-time depth and/or lateral position of the target), planned trajectory of the medical instrument, real-time trajectory of the medical instrument, (real-time) trajectory updates, number of checkpoints (CPs) along the planned or real-time-updated trajectory of the medical instrument, CP positions/locations, CP updates during the procedure, CP errors (in 2D and/or in 3D), position of the medical device, insertion angles of the medical instrument (for example, insertion angle in the axial plane and off-axial angle), indication whether the planned (indicated) target has been reached during the procedure, target error (for example, lateral and depth, in 2D and/or in 3D), scans/images, parameters per scan, radiation dose per scan, total radiation dose in the steering phase of the medical instrument, total radiation dose the entire procedure, errors/warnings indicated during the procedure, software logs, motion control traces, medical device registration logs, medical instrument (such as, needle) detection logs, homing and BIT results, and the like, or any combination thereof. Each possibility is a separate embodiment. In some embodiments, one or more of the values may be configured to be collected automatically by the system. For example, values such as procedure steps timing, overall steering time, entry, target, target updates (depth and lateral), trajectory, trajectory updates, number of CPs, CP positions, CP updates, CP errors (2 planes and/or 3D), robot position, scans/images, parameters per scan, errors/warnings, software logs, motion control traces, medical device registration logs, medical instrument detection logs, homing and BIT results may be collected automatically.

According to some exemplary embodiments, the clinical procedures related dataset may include such data parameters or values as, but not limited to: procedure type (e.g., blood/fluid sampling, regional anesthesia, tissue biopsy, catheter insertion, cryogenic ablation, electrolytic ablation, brachytherapy, neurosurgery, deep brain stimulation, various minimally invasive surgeries, and the like), target organ, target size, target type (tumor, abscess, and the like), type of medical instrument, size of medical instrument, complications before/during/after the procedure, adverse events before/during/after the procedure, respiration signals of the patient, and the like, or any combination thereof. Each possibility is a separate embodiment. In some embodiments, one or more of the values may be configured to be collected automatically. For example, the type of medical instrument (for example, type of a needle), size of the medical instrument (for example, size (gauge) of the needle), respiration signal(s) of the patient, movement traces of the automated medical device and system logs may be collected automatically. In some embodiments, one or more of the values may be configured to be collected manually by requesting the user to insert the data, information and/or visual marking using a graphic-user-interface (GUI), for example.

According to some exemplary embodiments, the patient related dataset may include such data parameters or values as, but not limited to: age, gender, race, relevant medical history, vital signs before/after/during the procedure, body dimensions (height, weight, BMI, circumference, etc.), current medical condition, pregnancy, smoking habits, demographic data, and the like, or any combination thereof. Each possibility is a separate embodiment.

According to some exemplary embodiments, the administrative related dataset may include such data parameters or values as, but not limited to: institution (healthcare facility) in which the procedure is performed, physician, staff, system serial numbers, disposables used, software/operating systems versions, configuration parameters, and the like, or any combination thereof. Each possibility is a separate embodiment.

According to some embodiments, by using one or more values of one or more datasets, and generating a data-analysis algorithm, various predictions, recommendations and/or implementations may be generated that can enhance further medical procedures. In some embodiments, based on the data used, the generated algorithm/s may be customized to a specific procedure, specific patient (or cohort of patients), or any other set of specific parameters.

According to some embodiments, the algorithm/s may be used for enhancing medical procedures, predicting clinical outcome and/or clinical complications and overall increasing safety and accuracy.

According to some exemplary embodiments, the data-analysis algorithms generated by the systems and methods disclosed herein may be used for, but not limited to: Predicting, prevention and/or detecting various clinical conditions and/or complications (e.g., pneumothorax, internal bleeding, breathing abnormalities, etc.); Determining or recommending entry point location; Determining or recommending an optimal trajectory for the insertion procedure; Optimizing checkpoint positioning along a trajectory (planned and/or updated trajectory), e.g., by recommending the best tradeoff between accuracy and radiation exposure/procedure time; Determining or recommending "no-fly" zones, i.e., areas (obstacles and/or vital anatomical structures) to avoid during instrument insertion; Predicting and/or detecting entrance into defined "no-fly" zones; Predicting real-time tissue (including target) movement; Automatic (real-time) target tracking; Automatic steering of the instrument based on real-time target tracking; Optimizing automatic breathing synchronization; Optimizing the positioning of the medical device relative to a subject's body and/or recommending to the user how to position the medical device relative to the subject's body, as disclosed, for example, in co-owned International Application No. PCT/IL2020/051247, which is incorporated herein by reference in its entirety; Optimizing steering algorithm corrections; Optimizing medical device registration and instrument detection algorithms thereby improving system accuracy and allowing radiation reduction; Optimizing compensation calculations for determining the actual real-time location of the tip of the medical instrument, as disclosed, for example, in abovementioned co-owned International Application No. PCT/IL2020/051219; Recommending the medical instrument to be used in the procedure (instrument type, instrument gauge, etc.); Evaluating procedure success (estimated success and/or estimated risk level) based on the current planning and similar past procedures; Correlating procedure success and/or morbidity/mortality with different parameters, such as target type, target size, trajectory, etc.; Minimizing radiation level; Improving image quality (e.g., in case of low-quality imaging system or low-dose scanning); 3D reconstruction and segmentation of organs and tissues; Integrating obtained images with the subject's medical records to fine tune the procedure planning and/or better evaluate risks; Utilizing force sensor measurements for evaluation of tissue compliance, early detection of clinical complications and/or optimizing instrument steering; Utilization of additional sensor measurements (e.g., accelerometer, radiation sensor, etc.); Generating voice commands to operate the automated device; Use of augmented reality (AR) and/or virtual reality (VR) for device positioning, target tracking and/or instrument tracking, etc.; Evaluating clinical procedure efficiency, e.g., evaluating the impact of ablation on the target and the surrounding tissue (and recommending the ablation treatment area accordingly), evaluating drug delivery (including anesthesia) efficiency based on instrument location and/or volume analysis; Analyzing the outcome of the procedure, both short term and long term, to identify long term implications and correlations; Providing data and analysis to, for example, healthcare providers, healthcare facilities, imaging systems' manufacturers, medical instruments' manufacturers, to be used as needed; Predicting and/or detecting system failures and 'service required' alerts; Medical personnel training programs based on experts' procedures; Medical personnel performance analysis; and the like, or any combination thereof. Each possibility is a separate embodiment.

According to some embodiments, data-analysis algorithms generated by the systems and methods disclosed herein may be used for providing prediction, prevention and/or early detection of various clinical conditions/complications, such as pneumothorax, local bleeding, etc. According to some embodiments, generated algorithms may be used for providing recommendations regarding various device functions and operations, including providing optimized routes or modes of operation. According to some embodiments, generated algorithms may be used for providing improved/optimized procedures, while taking into account various variables that may change during the procedure, such as, for example, predicting target movement, correlating body movement (breathing-related) and device operation, etc. In some embodiments, generated algorithms may be used to predict service calls and potential system malfunctions. In some embodiments, generated algorithms may be used to allow performance analysis and user feedback, to improve the use of the medical device.

According to some embodiments, a training module (also referred to as "learning module") may be used to train an AI model (e.g., ML or DL-based model) to be used in an inference module, based on the datasets and/or the features extracted therefrom and/or additional metadata, in the form of annotations (e.g., labels, bounding-boxes, segmentation maps, visual locations markings, etc.). In some embodiments, the training module may constitute part of the inference module or it may be a separate module. In some embodiments, a training process (step) may precede the inference process (step). In some embodiments, the training process may be on-going and may be used to update/validate/enhance the inference step (see "active-learning" approach described herein). In some embodiments, the inference module and/or the training module may be located on a local server ("on premise"), a remote server (such as, a server farm or a cloud-based server) or on a computer associated with the automated medical device. According to some embodiments, the training module and the inference module may be implemented using separate computational resources. In some embodiments, the training module may be located on a server (local or remote) and the inference module may be located on a local computational resource (computer), or vice versa. According to some embodiments, both the training module and the inference module may be implemented using common computational resources, i.e., processors and memory components shared therebetween. In some embodiments, the inference module and/or the training module may be located or associated with a controller (or steering system) of an automated medical device. In such embodiments, a plurality of inference modules and/or learning modules (each associated with a medical device or a group of medical devices), may interact to share information therebetween, for example, utilizing a communication network. In some embodiments, the model(s) may be updated periodically (for example, every 1-36 weeks, every 1-12 months, etc.). In some embodiments, the model(s) may be updated based on other business logic. In some embodiments, the processor(s) of the automated medical device (e.g., the processor of the insertion system) may run/execute the model(s) locally, including updating and/or enhancing the model(s).

According to some embodiments, during training of the model (as detailed below), the learning module (either implemented as a separate module or as a portion of the inference module), may be used to construct a suitable algorithm (such as, a classification algorithm), by establishing relations/connections/patterns/correspondences/correlations between one or more variables of the primary datasets and/or between parameters derived therefrom. In some embodiments, the learning may be supervised learning (e.g., classification, object detection, segmentation and the like). In some embodiments, the learning may be unsupervised learning (e.g., clustering, anomaly detection, dimensionality reduction and the like). In some embodiments the learning may be reinforcement learning. In some embodiments, the learning may use a self-learning approach. In some embodiments, the learning process is automatic. In some embodiments, the learning process is semi-automatic. In some embodiments, the learning is manually supervised. In some embodiments, at least some variables of the learning process may be manually supervised/confirmed, for example, by a user (such as a physician). In some embodiments, the training stage may be an offline process, during which a database of annotated training data is assembled and used for the creation of data-analysis model(s)/algorithm(s), which may then be used in the inference stage. In some embodiments, the training stage may be performed "online", as detailed herein.

According to some embodiments, the generated algorithm may essentially constitute at least any suitable specialized software (including, for example, but not limited to: image recognition and analysis software, statistical analysis software, regression algorithms (linear, non-linear, or logistic etc.), and the like). According to some embodiments, the generated algorithm may be implemented using an artificial neural network (ANN), such as a deep neural network (DNN), a convolutional neural network (CNN), a recurrent neural network (RNN) and the like, decision trees or graphs, association rule learning, support vector machines, inductive logic programming, Bayesian networks, instance-based learning, manifold learning, sub-space learning, and the like, or any combination thereof. The algorithm or model may be generated using machine learning tools, data wrangling tools, deep learning tools, and, more generally, data science and artificial intelligence (AI) learning tools, as elaborated hereinbelow.

Reference is now made to FIGS. 7A-7B, which show an exemplary training module (FIG. 7A) and an exemplary training process (FIG. 7B), according to some embodiments.

As shown in FIG. 7A, a training module 70 may include two main hardware components/units: at least one memory 72 and at least one processing unit 74, which are functionally and/or physically associated. Training module 70 may be configured to train a model based on data. Memory 72 may include any type of accessible memory (volatile and/or non-volatile), configured to receive, store and/or provide various types of data, to be processed by processing unit 74, which may include any type of at least one suitable processor, as detailed below. In some embodiments, the memory and the processing units may be functionally or physically integrated, for example, in the form of a Static Random Access Memory (SRAM) array. In some embodiments, the memory is a non-volatile memory having stored therein executable instructions (for example, in the form of a code, service, executable program and/or a model file). As shown in FIG. 7A, the memory unit 72 may be configured to receive, store and/or provide various types of data values or parameters related to the data. Memory 72 may store or accept raw (primary) data 722 that has been collected, as detailed herein. Additionally, metadata 724, related to the raw data 722 may also be collected/stored in memory 72. Such metadata may include a variety of parameters/values related to the raw data, such as, but not limited to: the specific device which was used to provide the data, the time the data was obtained, the place the data was obtained (such as a specific procedure/operating room, specific institution, etc.), and the like. Memory 72 may further be configured to store/collect data annotations (e.g., labels) 726. In some embodiments, the collected data may require additional steps for the generation of data-annotations that will be used for the generation of the machine-learning, deep-learning models or other statistical or predictive algorithms as disclosed herein. In some embodiments, such data annotations may include labels describing the clinical procedure's characteristics, the automated device's operation and computer-vision related annotations, such as segmentation masks, target marking, organs and tissues marking, and the like. The different annotations may be generated in an "online" manner, which is performed while the data is being collected, or in an "offline" manner, which is performed at a later time after sufficient data has been collected. The memory 72 may further include features database 728. The features database 728 may include a database ("store") of previously known or generated features that may be used in the training/generation of the models. The memory 72 of training module 70 may further, optionally, include pre-trained models 729. The pre-trained models 729 include existing pre-trained algorithms which may be used to automatically annotate a portion of the data and/or to ease training of new models using "transfer-learning" methods and/or to shorten training time by using the pre-trained models as starting points for the training process on new data and/or to evaluate and compare performance metrics of existing versus newly developed models before deployment of new model to production, as detailed hereinbelow. In some embodiments, processing unit 72 of training module 70 may include at least one processor, configured to process the data and allow/provide model training by various processing steps (detailed in FIG. 7B). Thus, as shown in FIG. 7A, processing unit 74 may be configured at least to perform pre-processing of the data 742. Pre-processing of the data may include actions for preparing the data stored in memory 72 for downstream processing, such as, but not limited to, checking for and handling null values, imputation, standardization, handling categorical variables, one-hot encoding, resampling, scaling, filtering, outlier removal etc. Processing unit 74 may further, optionally, be configured to perform feature extraction 744, in order to reduce the raw data dimension and/or add informative domain-knowledge into the training process and allow the use of additional machine-learning algorithms not suitable for training on raw data and/or optimization of existing or new models by training them on both the raw data and the extracted features. Feature extraction may be executed using dimensionality reduction methods, for example, Principal Components Analysis (PCA), Independent Component Analysis (ICA), Linear Discriminant Analysis (LDA), Locally Linear Embedding (LLE), t-distributed Stochastic Neighbor Embedding (t-SNE), Unified Manifold Approximation and Projection (UMAP) and/or Autoencoders, etc. Feature extraction may be executed using feature engineering methods in which mathematical tools are used to extract domain-knowledge features from the raw data, for example—statistical features, such as mean, variance, ratio, frequency etc. and/or visual features, such as dimension or shape of certain objects in an image. Another optional technique which may be executed by the processing unit 74 to reduce the number of features in the dataset is feature selection, in which the importance of the existing features in the dataset is ranked and the less important features are discarded (i.e., no new features are created). Processing unit 74 may further be configured to execute model training 746.

Reference is now made to FIG. 7B, which shows steps in an exemplary training process 76, executed by a suitable training module (such as training module 70 of FIG. 7A). As shown in FIG. 7B, at optional step 761, the collected datasets may first require an Extract-Transform-Load (ETL) or ELT process that may be used to (1) Extract the data from a single or multiple data sources (including, but not limited to, the automated medical device itself, Picture Archiving and Communication System (PACS), Radiology Information System (RIS), imaging device, healthcare facility's Electronic Health Record (EHR) system, etc.), (2) Transform the data by applying one or more of the following steps: handling missing values, checking for duplicates, converting data types as needed, encoding values, joining data from multiple sources, aggregating data, translating coded values etc. and (3) Load the data to a variety of data storage devices (on-premise or at a remote location (such as a cloud server)) and/or to a variety of data stores, such as file systems, SQL databases, no-SQL databases, distributed databases, object storage, etc. In some embodiments, the ETL process may be automatic and triggered with every new data collected. In other embodiments, the ETL process may be triggered at a predefined schedule, such as once a day or once a week, for example. In some embodiments, another business logic may be used to decide when to trigger the ETL process.

At step 762, the data may be cleaned to ensure high quality data by, for example removal of duplicates, removal or modification of incorrect and/or incomplete and/or irrelevant data samples, etc. At step 763, the data is annotated. The data annotations may include, for example, labels describing the clinical procedure's characteristics, the automated device's operation and computer-vision related annotations, such as segmentation masks, target marking, organs and tissues marking, existence of medical conditions/complications, existence of certain pathologies, etc. The different annotations may be generated in an "online" manner, which is performed while the data is being collected, or in an "offline" manner, which is performed at a later time after sufficient data has been collected. In some embodiments, data annotations may be generated automatically using an "active learning" approach, in which existing pre-trained algorithms are used to automatically annotate a portion of the data. In some embodiments, the data annotations may be generated using a partially automated approach with "human in the loop", i.e., human approval or human annotations will be required in cases where the annotation confidence is low, or per other business logic decision or metric. In some embodiments, the data annotations may be generated in a manual approach, i.e., using human annotators to generate the required annotations using convenient annotation tools. Next, at step 764, the annotated data is pre-processed, for example, by one or more of checking for and handling null values, imputation, standardization, handling categorical variables, one-hot encoding, resampling, scaling, filtering, outlier removal and other data manipulations, to prepare the data for further processing. At optional step 765, extraction (or selection) of various features of the data may be performed, as explained hereinabove. At step 766, the data and/or features extracted therefrom is divided to training data ("training set"), which will be used to train the model, and testing data ("testing set"), which will not be introduced into the model during model training so it can be used as "hold-out" data to test the final trained model before deployment. The training data may be further divided into a "train set" and a "validation set", where the train set is used to train the model and the validation set is used to validate the model's performance on unseen data, to allow optimization/ fine-tuning of the training process' configuration/hyperparameters during the training process. Examples for such hyperparameters may be the learning-rate, weights regularization, model architecture, optimizer selection, etc. In some embodiments, the training process may include the use of a Cross-Validation (CV) methods in which the training data is divided into a "train set" and a "validation set", however, upon training completion, the training process may repeat multiple times with different selections of "train set" and "validation set" out of the original training data. The use of CV may allow a better validation of the model during the training process as the model is being validated against different selections of validation data. At optional step 767, data augmentation is performed. Data augmentation may include, for example, generation of additional data from/ based on the collected or annotated data. Possible augmentations that may be used for image data are: rotation, flip, noise addition, color distribution change, crop, stretch, etc. Augmentations may also be generated using other types of data, for example by adding noise or applying a variety of mathematical operations. In some embodiments, augmentation may be used to generate synthetic data samples using synthetic data generation approaches, such as distribution based, Monte-Carlo, Variational Autoencoder (VAE), Generative-Adversarial-Network (GAN), etc. Next, at step 768, the model is trained, wherein the training may be performed "from scratch" (i.e., an initial/primary model with initialized weights is trained based on all relevant data) and/or utilizing existing pre-trained models as starting points and training them only on new data. At step 769, the generated model is validated. Model validation may include evaluation of different model performance metrics, such as accuracy, precision, recall, F1 score, AUC-ROC, etc., and comparison of the trained model against other existing models, to allow deployment of the model which best fits the desired solution. The evaluation of the model at this step is performed using the testing data ("test set") which was not used for model training nor for hyperparameters optimization and best represents the real-world (unseen) data. At step 770, the trained model is deployed and integrated or utilized with the inference module to generate output based on newly collected data, as detailed herein.

According to some embodiments, as more data is collected, the training database may grow in size and may be updated. The updated database may then be used to re-train the model, thereby updating/enhancing/improving the model's output. In some embodiments, the new instances in the training database may be obtained from new clinical cases or procedures or from previous (existing) procedures that have not been previously used for training. In some embodiments, an identified shift in the collected data's distribution may serve as a trigger for the re-training of the model. In other embodiments, an identified shift in the deployed model's performance may serve as a trigger for the re-training of the model. In some embodiments, the training database may be a centralized database (for example, a cloud-based database), or it may be a local database (for example, for a specific healthcare facility). In some embodiments, learning and updating may be performed continuously or periodically on a remote location (for example, a cloud server), which may be shared among various users (for example, between various institutions, such as hospitals). In some embodiments, learning and updating may be performed continuously or periodically on a single or on a cohort of medical devices, which may constitute an internal network (for example, of an institution, such as a hospital). For example, in some instances, a validated model may be executed locally on processors of one or more medical systems operating in a defined environment (for example, a designated institution, such as a hospital), or on local online servers of the designated institution. In such case, the model may be continuously updated based on data obtained from the specific institution ("local data"), or periodically updated based on the local data and/or on additional external data, obtained from other resources. In some embodiments, federated learning may be used to update a local model with a model that has been trained on data from multiple facilities/ tenants without requiring the local data to leave the facility or the institution.

Reference is now made to FIGS. 8A-8B, which show an exemplary inference module (FIG. 8A) and an exemplary inference process (FIG. 8B), according to some embodiments.

As shown in FIG. 8A, inference module 80 may include two main hardware components/units: at least one memory unit 82 and at least one processing unit 84, which are functionally and/or physically associated. Inference module 80 is essentially configured to run collated data into the trained model to calculate/process an output/prediction. Memory 82 may include any type of accessible memory (volatile and/or non-volatile), configured to receive, store and/or provide various types of data and executable instructions, to be processed by processing unit 84, which may include any type of at least one suitable processor. In some embodiments, the memory 82 and the processing unit 84 may be functionally or physically integrated, for example, in the form of a Static Random Access Memory (SRAM) array. In some embodiments, the memory is a non-volatile memory having stored therein executable instructions (for example, in the form of a code, service, executable program and/or a model file containing the model architecture and/or weights) that can be used to perform a variety of tasks, such as data cleaning, required pre-processing steps and inference operation (as detailed below) on new data to obtain the model's prediction or result. As shown in FIG. 8A, memory 82 may be configured to accept/receive, store and/or provide various types of data values or parameters related to the data as well as executable algorithms (in the case of machine learning based algorithms, these may be referred to as "trained models"). Memory unit 82 may store or accept new acquired data 822, which may be raw (primary) data that has been collected, as detailed herein. Memory module 82 may further store metadata 824 related to the raw data. Such metadata may include a variety of parameters/values related to the raw data, such as, but not limited to: the specific device which was used to provide the data, the time the data was obtained, the place the data was obtained (such as specific operation room, specific institution, etc.), and the like. Memory 82 may further store the trained model(s) 826. The trained models may be the models generated and deployed by a training module, such as training module 70 of FIG. 7A. The trained model(s) may be stored, for example in the form of executable instructions and/or model file containing the model's weights, capable of being executed by processing unit 84. Processing unit 84 of inference module 80 may include at least one processor, configured to process the new obtained data and execute a trained model to provide corresponding results (detailed in FIG. 8B). Thus, as shown in FIG. 8A, processing unit 84 is configured at least to perform pre-processing of the data 842, which may include actions for preparing the data stored in memory 82 for downstream processing, such as, but not limited to, checking for and handling null values, imputation, standardization, handling categorical variables, one-hot encoding, resampling, scaling, filtering, outlier removal etc. In some embodiments, processing unit 84 may further be configured to extract features 844 from the acquired data, using techniques such as, but not limited to, Principal Components Analysis (PCA), Independent Component Analysis (ICA), Linear Discriminant Analysis (LDA), Locally Linear Embedding (LLE), t-distributed Stochastic Neighbor Embedding (t-SNE), Unified Manifold Approximation and Projection (UMAP) and/or Autoencoders, etc. Feature extraction may be executed using feature engineering methods in which mathematical tools are used to extract domain-knowledge features from the raw data, for example: statistical features such as mean, variance, ratio, frequency etc. and/or visual features such as dimension or shape of certain objects in an image. Alternatively, or additionally, the processing unit 84 may be configured to perform feature selection. Processing unit 84 may further be configured to execute the model on the collected data and/or features extracted therefrom, to obtain model results 846. In some embodiments, the processing unit 84 may further be configured to execute a business logic 848, which can provide further fine-tuning of the model results and/or utilization of the model's results to a variety of automated decisions, guidelines or recommendations supplied to the user.

Reference is now made to FIG. 8B, which shows steps in an exemplary inference process 86, executed by a suitable inference module (such as inference module 80 of FIG. 8A). As shown in FIG. 8B, at step 861, new data is acquired/collected from or related to newly executed medical procedures. The new data may include any type of raw (primary) data, as detailed herein. At optional step 862, suitable trained model(s) (generated, for example by a suitable training model in a corresponding training process) may be loaded, per task(s). This step may be required in instances in which computational resources are limited and only a subset of the required models or algorithms can be loaded into RAM memory to be used for inference. In such cases, the inference process may require an additional management step responsible to load the required models from storage memory for a specific subset of inference tasks/jobs, and once inference is completed, the loaded models are replaced with other models that will be loaded to allow an additional subset of inference tasks/jobs. Next, at step 863, the raw data collected in step 861 is pre-processed. In some embodiments, the pre-processing steps may be similar or identical to the pre-processing step preformed in the training process (by the training module), to thereby allow the data to be processed similarly by the two modules (i.e., training module and inference module). In some embodiments, this step may include actions such as, but not limited to, checking for and handling null values, imputation, standardization, handling categorical variables, one-hot encoding, etc., to prepare the input data for analysis by the model(s). Next, at optional step 864, extraction of features from the data may be performed using, for example, Principal Components Analysis (PCA), Independent Component Analysis (ICA), Linear Discriminant Analysis (LDA), Locally Linear Embedding (LLE), t-distributed Stochastic Neighbor Embedding (t-SNE), Unified Manifold Approximation and Projection (UMAP) and/or Autoencoders, etc. Alternatively, or additionally, feature selection may be executed. At inference step 865, the results of the model are obtained, i.e., the model is executed on the processed data to provide corresponding results. At optional step 866, fine-tuning of the model results may be performed, whereby post-inference business logic is executed. Execution of post-inference business logic refers to the utilization of the model's results to a variety of automated decisions, guidelines or recommendations supplied to the user. Post-inference business logic may be configured to accommodate specific business and/or clinical needs or metrics, and can vary between different scenarios or institutions based on users' or institutions' requests or needs.

At step 867, the model results may be utilized in various means, including, for example, providing prediction, prevention and/or early detection of various clinical conditions (e.g., pneumothorax, breathing anomalies, bleeding, etc.), enhancing the operation of the automated medical device (e.g., enabling automatic target tracking and closed-loop steering based on the tracked real-time position of the target, etc.), providing recommendations regarding various device operations (including recommending one or more optimal entry points, recommending optimized trajectories or modes of operation, etc.), and the like, as further detailed hereinabove.

In some embodiments, inference operation may be performed on a single data instance. In other embodiments, inference operation may be performed using a batch of multiple data instances to receive multiple predictions or results for all data instances in the batch. In some embodiments, an ensemble of models or algorithms can be used for inference, where the same input data is processed by a group of different models and results are being aggregated using averaging, majority voting or the like. In some embodiments, the model can be designed in a hierarchical manner where input data is processed by a primary model and based on the prediction or result of the primary model's inference, the data is processed by a secondary model. In some embodiments, multiple secondary models may be used, and hierarchy may have more than two levels.

According to some embodiments, the methods and systems disclosed herein utilize data-driven methods to create algorithms based on various datasets, including, functional, anatomical, clinical, diagnostic, demographic and/or administrative datasets. In some embodiments, artificial intelligence (e.g., machine-learning) algorithms are used to learn the complex mapping/correlation/correspondence between the multimodal (e.g., data obtained from different modalities, such as images, logs, sensory data, etc.) input datasets parameters (procedure, clinical, operation, patient related and/or administrative information), to optimize the clinical procedure's outcome or any other desired functionalities. In some embodiments, the systems and methods disclosed herein determine such optimal mapping using various approaches, such as, for example, a statistical approach, and utilizing machine-learning algorithms to learn the mapping/correlation/correspondence from the training datasets.

Reference is now made to FIGS. 9A-9C, which show exemplary medical procedural implications, which may be automatically analyzed/enhanced by a data-analysis algorithm, according to some embodiments. Reference is made to FIG. 9A, which shows a pictogram of a demonstration of an indication/recommendation of "no-fly" zones 90 and 92, which are regions to be avoided during the medical procedure (insertion of a needle in the example shown in FIG. 9A), in order to prevent damage to a vital/sensitive organ (aorta and spine, in the example shown in FIG. 9A) or to the medical instrument. Thus, based on collected primary datasets and training sets, an algorithm generated based on data science and/or machine learning tools (including, for example, image analysis, such as classification, object detection and/or segmentation of scans and correlation of body movement during the procedure) can recommend such "no-fly" zones, to thereby enhance the safety of the medical procedure, as described in further detail hereinbelow.

Reference is made to FIG. 9B, which shows a pictogram of a demonstration of real-time target movement during a needle insertion procedure. During the insertion/steering procedure, the target 94 may move, for example, due to body motion during the breathing cycle, or as a result from the insertion of the needle 96 into the tissue, thus it is of vital importance to determine the real-time location of the target 94 in order to ensure a safe and successful procedure. Accordingly, based on collected primary datasets and training sets, a data-analysis algorithm can predict the real-time movement of the target 94, and the initial planning and/or real-time updating of the trajectory can then be based, inter alia, on the target's predicted movement, thereby enhancing the safety and accuracy of the medical procedure.

Reference is made to FIG. 9C, which shows a pictogram of a demonstration of checkpoints 93 located along a trajectory 95 for inserting a medical instrument (e.g., needle) toward an internal target. Checkpoints may be used to pause the insertion of the medical instrument and initiate imaging of the region of interest, to verify the position of the instrument, target and/or obstacle/s. The trade-off of utilizing many checkpoints is prolonged procedure time, as well as repeated exposure to radiation. On the other hand, too little checkpoints may affect the accuracy and safety of the medical procedure. Accordingly, based on the collected datasets and the training data, a data-analysis algorithm can be trained to recommend optimal checkpoint locations during the planning phase and/or during the procedure, as described in further detail hereinbelow.

In some embodiments, the algorithm may be a generic algorithm, which is agnostic to specific procedure characteristics, such as type of procedure, user, service provider or patient. In some embodiments, the algorithm may be customized to a specific user (for example, preferences of a specific healthcare provider), a specific service provider (for example, preferences of a specific hospital), a specific population (for example, preferences of different age groups), a specific patient (for example, preferences of a specific patient), and the like. In some embodiments, the algorithm may be combined a generic portion and a customized portion.

Figure 10:
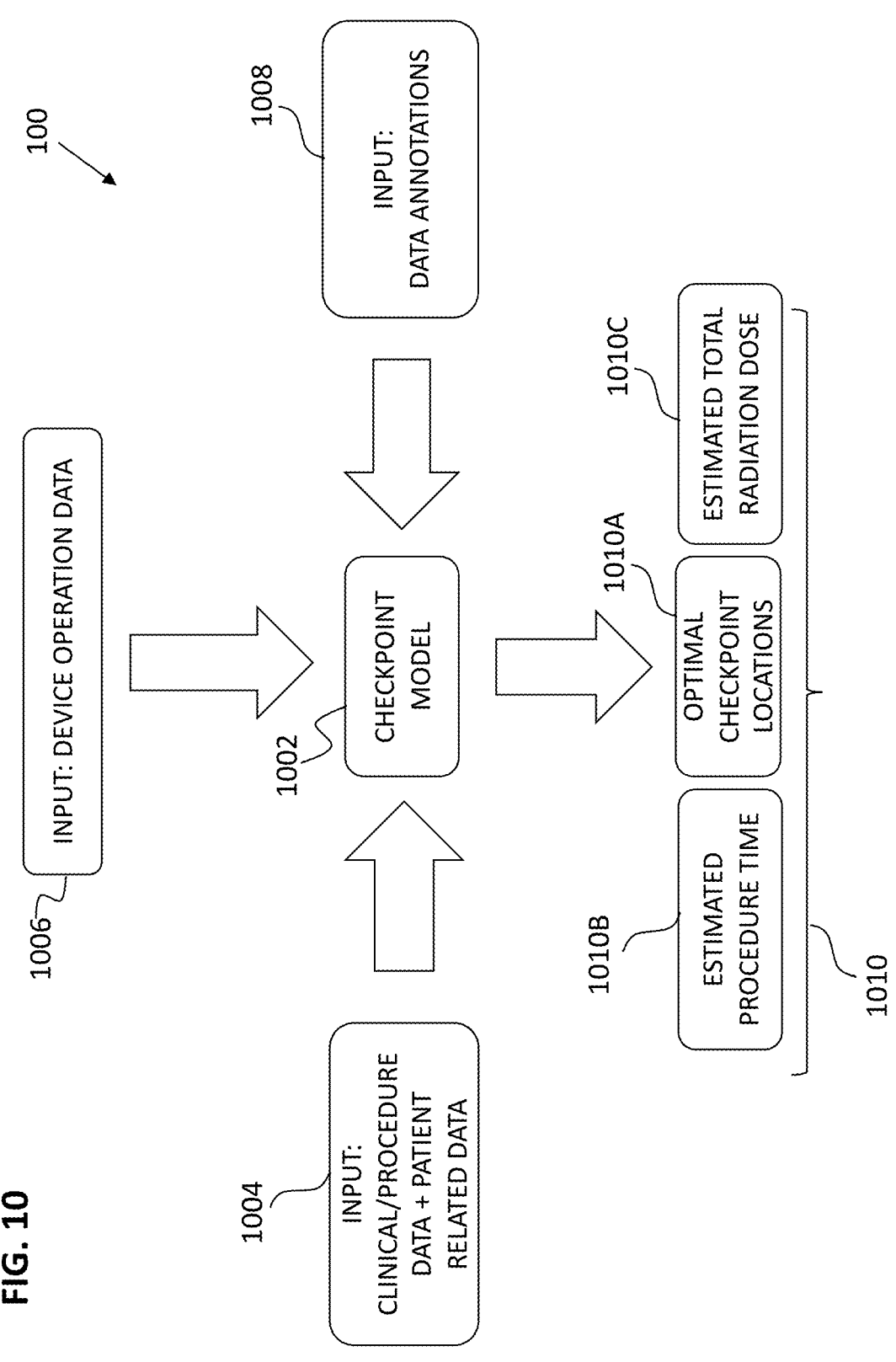
FIG. 10 shows a block diagram of exemplary datasets used for generating an AI model for optimizing checkpoint locations, and exemplary output of the checkpoint model, according to some embodiments.

Reference is now made to FIG. 10, which shows a block diagram 100 of exemplary datasets and parameters used for generating a checkpoint AI model 1002 for optimizing checkpoint locations, and an exemplary output 1010 of the checkpoint model 1002, according to some embodiments. As detailed above, in many cases it is imperative to determine optimal checkpoint (CP) locations (i.e., the number of checkpoints and their positioning along the planned and/or updated trajectory), to allow maximal accuracy and minimal radiation exposure and/or procedure time. To this aim, one or more data-analysis algorithms, for example CP model 1002, may be generated, based on various datasets and parameters. For example, input data may include clinical/procedure and patient-related data 1004, device operation data 1006 and ground truth annotations (also referred to as "target variables") 1008. The clinical/procedure data 1004 may include values and/or parameters, such as, but not limited to: procedure type (e.g., biopsy, ablation, fluid drainage, etc.), target organ, target type, target size, instrument type (e.g., introducer, biopsy needle, ablation probe, etc.), instrument gauge, instrument tip type (e.g., diamond tip, bevel tip), images (e.g., CT scans) and scanning parameters, respiration signal and status, respiration abnormalities, patient specific parameters (age, gender, race, BMI, clinical condition, etc.). The device operation data 1006 may include values and/or parameters such as, but not limited to: entry point, insertion angle (relative to one or more axis), target position, target position updates, instrument trajectory (planned and updated, if updated), trajectory path (i.e., tissue transitions along the trajectory), actual instrument trajectory (i.e., actual instrument position at each CP, optionally including a time stamp), position of the device relative to the patient's body, steering steps timing, procedure accuracy (e.g., instrument (e.g., the tip thereof) distance to target), target error, medical images, medical imaging parameters per scan, sensor(s) measurements, errors indicated during the steering procedure, software logs, motion control traces, automated medical device registration logs, medical instrument detection logs, homing and BIT results, and the like. The data annotations 1008 may include values and/or parameters such as, but not limited to: procedure duration (total and/or by insertion steps), total radiation dose in the procedure, total radiation dose for the instrument steering phase of the procedure, average radiation dose per scan (i.e., per checkpoint), number of checkpoints, checkpoint positions, checkpoint updates, checkpoint errors (e.g., the deviation of the actual CP location (the location the instrument tip actually reached) from the planned CP location, duration of the steering phase of the procedure, procedure accuracy (e.g., instrument tip-to-target distance), complications occurrence (yes/no), complications detection time, organs segmentation masks and/or bounding boxes and/or locations, tissues segmentation mask and/or bounding boxes and/or locations, target contours and/or bounding box and/or locations, "no-fly" zones masks and/or bounding boxes and/or locations, blood vessels mask and/or bounding boxes and/or locations, instrument segmentation mask and/or bounding box and/or locations, and the like. The various input datasets and the parameters derived therefrom (some or all) may be utilized to generate one or more CP models 1002. In some embodiments, each or at least some of the parameters are attributed an appropriate weight which is taken into account in generating the CP model 1002. The generated model can thus provide recommendations and/or assessments regarding the optimal checkpoint locations 1010A. In some embodiments, the model 1002 may provide additional assessments and/or predictions, such as, but not limited to: the estimated duration of the procedure 1010B (for example, the estimated time required for steering an instrument to the target) and the estimated total radiation dose 1010C (associated with CT scans, for example) during the procedure and/or during the steering phase of the procedure. In some embodiments, the recommendations may be implemented automatically or semi-automatically in a corresponding medical procedure. In some embodiments, the recommendations may be provided to the user, e.g., visually on a graphical user interface (GUI) on a display of the medical device/system, a controller system, a mobile device, a Virtual Reality (VR) device and/or an Augmented Reality (AR) device, for his/her approval prior to implementation. In a fully automated process, the additional output may be for information only (if provided at all), whereas in a semi-automatic process (or manually involved process), the additional output is provided to the physician, so that the physician can use this data to decide if to accept the recommendation or change the CP locations (for example, move any of the CPs, add or delete one or more CPs). According to some embodiments, the output 1010 may be provided during the planning stage of the procedure, with the main output being a recommendation of the optimal CP locations (i.e., number of CPs and their positions along the planned trajectory).

Figure 11:
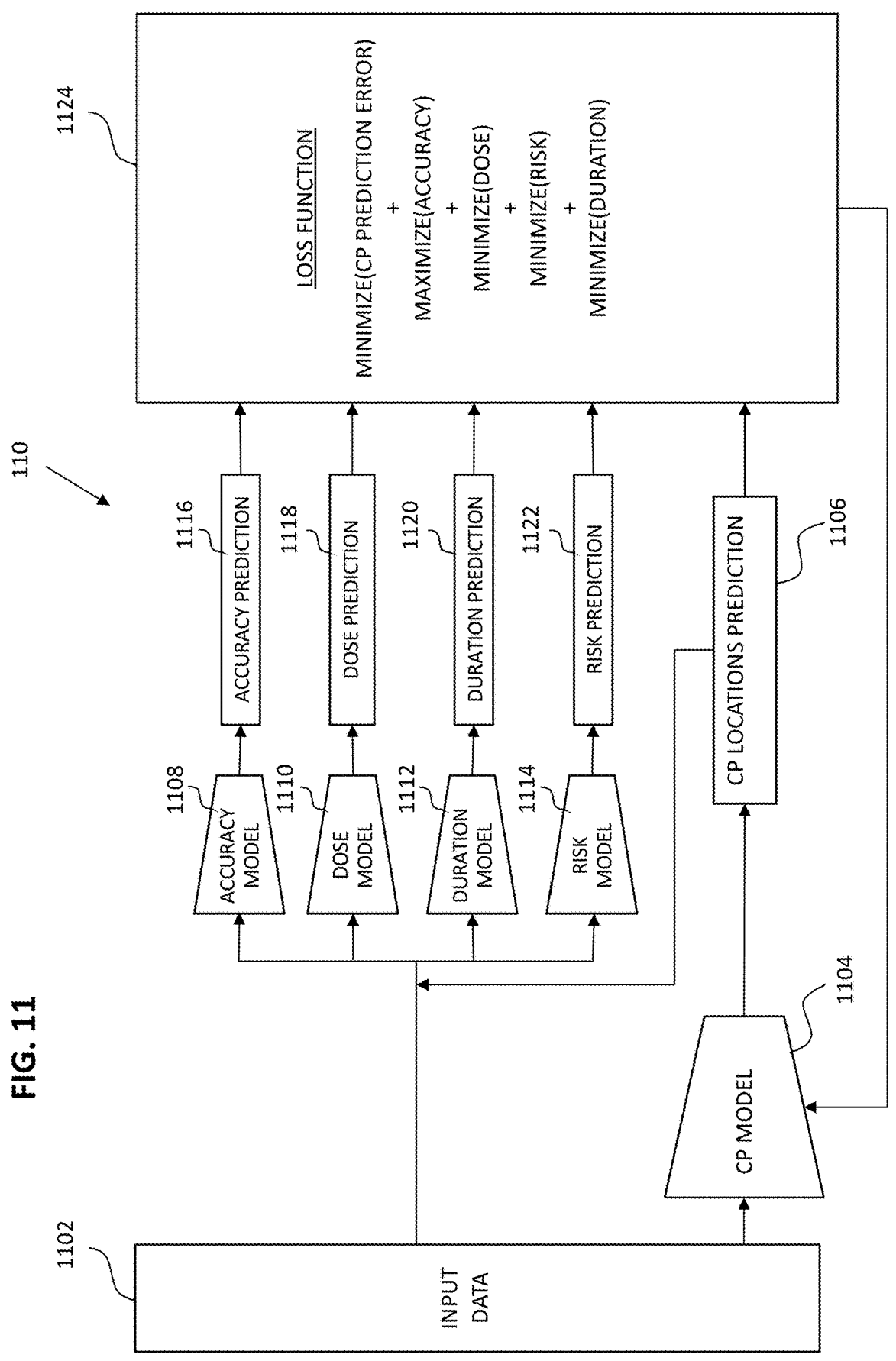
FIG. 11 shows a block diagram illustrating an exemplary method of training an AI model for optimizing checkpoint locations, according to some embodiments.

Reference is now made to FIG. 11, which shows a block diagram 110 illustrating an exemplary method of generating (training) an AI model for optimizing checkpoint locations along an instrument trajectory in an image-guided procedure for inserting a medical instrument to an internal target, according to some embodiments. As described hereinabove, setting many checkpoints along the trajectory can increase the accuracy of the procedure (i.e., distance from the tip of the instrument to the target), since in each checkpoint real-time images (e.g., scans) may be obtained, and should there be a need (e.g., due to target movement), the trajectory can be updated. The trade-off, however, is prolonged procedure time, as well as repeated exposure to radiation. Therefore, in some embodiments, determining the optimal checkpoint locations should take into account the predicted accuracy of the procedure, the predicted radiation dose per initiated imaging (i.e., at each checkpoint) and the predicted duration of the steering phase of the procedure. In addition, to increase the safety of the patient, the predicted risk level of the procedure (e.g., probability of complications) may also be taken into account, according to some embodiments. To this end, in some embodiments, the training process of the checkpoint location model (also referred to as "checkpoint model" or "CP model") may include a preliminary phase of training one or more of the following individual models: an accuracy estimation model, a radiation dose estimation model, a duration estimation model, a risk estimation model, and any combination thereof. The input for training each of these individual models may include any relevant input obtained from previous procedures, such as, but not limited to, the data described in FIG. 10 hereinabove. In some embodiments, the target variable ("ground truth) for training the accuracy model is the procedure accuracy (e.g., instrument tip-to-target accuracy). In some embodiments, the target variable for training the radiation dose model is the average radiation dose per checkpoint. In some embodiments, the target variable for training the duration model is the duration of the steering phase of the procedure. In some embodiments, the target variable for training the risk model is the occurrence of complications during the procedure. It can be appreciated that for each individual model the target variable is not included in the input variables used for the training process of the individual model.

According to some embodiments, in the second phase of the checkpoint model training process the model is trained to predict CP locations as similar as possible to the ground truth CP locations (i.e., with minimal error from the actual CP locations along the trajectory in previous procedures). In some embodiments, the CP model is trained to output an optimized CP locations, i.e., not only to accurately predict the ground truth CP locations, but to provide a CP locations recommendation that will also result in the maximal possible tip-to-target accuracy, minimal total radiation dose during the steering phase, minimal steering phase duration and minimal risk for clinical complications during instrument steering. In some embodiments, such training may be executed using a loss function, e.g., a Multi-Loss scheme. In some embodiments, such training may be executed using Ensemble Learning methods. In some embodiments, such training may be executed using a Multi-Output regression/classification approach. In some embodiments, Multi-Task learning may be used. As shown in FIG. 11, which illustrates training executed using a Multi-Loss scheme, input data 1102, such as the data described above, is used to train the CP model 1104 to predict the CP locations 1106 (ground truth). The predicted CP locations 1106, together with the original input data 1102, is then used as input to the individual models 1108—accuracy model, dose model, duration model and risk model, to generate accuracy, radiation dose, duration and risk predictions 1110, respectively. The individual models' predictions 1110, together with the CP model's prediction, are then used to calculate a loss function 1112, aimed to minimize the CP locations prediction error, maximize the tip-to-target accuracy, minimize the radiation dose, minimize the duration and minimize the risk. The generated weighted loss represents the model's prediction error, which may be used to fine-tune or adjust the CP model's 1104 weights as part of the training process.

In some embodiments, only one or more of the individual models described above are used in the training process of the CP model. For example, in some embodiments only the accuracy and duration models may be used, whereas in other embodiments only the accuracy and dose models may be used. Further, the weights (coefficients) used in the Multi-Loss function 1112 may be adjusted according to certain needs and/or preferences. For example, if minimal radiation dose and/or minimal duration have a higher priority than CP locations prediction accuracy, tip-to-target accuracy and/or risk, the dose and duration may be given higher coefficients during the training process, such that they will have a greater impact on the CP locations recommendations. In some embodiments, different CP models may be trained for different needs and/or preferences. For example, one CP model may be trained to generate a CP locations recommendation that will allow the highest achievable tip-to-target accuracy, another CP model may be trained to generate a CP locations recommendation that will allow the lowest achievable radiation dose, a further CP model may be trained to generate a CP locations recommendation that will result in the shortest achievable duration, etc. In some embodiments, a single CP model may be trained and deployed, and the coefficients used in the Multi-Loss function 1112 may be adjusted during inference, i.e., during use of the CP model to generate a CP locations recommendation for a specific procedure. The need/preference upon which the coefficients may be fine-tuned may be associated with, for example, a specific procedure type (e.g., biopsy, fluid drainage, etc.), a specific target type, a specific user, a specific population, a specific user, etc.

Reference is now made to FIG. 12, which shows a flowchart 120 illustrating the steps of a method of utilizing a checkpoint model (an "inference" process) for optimizing checkpoint locations along a trajectory, according to some embodiments. At step 1202, a planned trajectory from an entry point to a target is obtained. At step 1204, boundaries between tissue layers along the trajectory are detected. In some embodiments, at optional step 1206, sections along the planned trajectory through which the instrument should be steered in "one shot" (for example, crossing the lung's pleura), thus no checkpoints are to be positioned along such sections, are defined. At step 1208, the scan volume and the radiation dose per checkpoint are, optionally, estimated. The scan volume may be estimated based, for example, on the position of the automated device relative to the subject's body (specifically, the position of the device's registration elements relative to the target), the insertion angle, the type and size of the target, etc. The radiation dose per checkpoint may be estimated based, for example, on the estimated scan volume and the planned imaging device configuration (e.g., intensity, slice thickness, resolution, etc.). In some embodiments, the scan volume may be estimated using an algorithm/model that was trained using data from previous procedures. Next, at step 1210, data and parameters obtained and/or calculated in the previous steps are used as input for the deployed CP model and the model's results are obtained. It can be appreciated that additional data may be used as input for the CP model, as described in detail hereinabove. At step 1212, checkpoints are set along the planned trajectory based on the results of the CP model. In some embodiments, the user may be prompted to confirm the set locations of the checkpoints. In some embodiments, the use may be able to adjust the set locations (as recommended by the processor). At step 1214, if the images (e.g., CT scans) obtained upon the instrument reaching a certain checkpoint during the steering procedure show that the target has moved from its initial position (or from its previous position as identified in images obtained at a previous checkpoint) and/or if the trajectory is updated due target movement, due to deviation of the instrument from the planned trajectory above a predetermined threshold and/or due to an obstacle identified along the planned trajectory, an updated recommendation for the locations of the subsequent checkpoints may be obtained from the CP model, and at step 1216, the locations of the subsequent checkpoints may be adjusted according to the updated results, if necessary (e.g., one or more checkpoints may be added or removed, e.g., the distance between two or more checkpoints and/or between the last checkpoint and the target may be adjusted, etc.). In some embodiments, the user may be prompted to confirm the adjusted locations of the subsequent checkpoints. In some embodiments, the use may be able to further adjust the adjusted locations of the subsequent checkpoints (as recommended by the processor).

Figure 13:
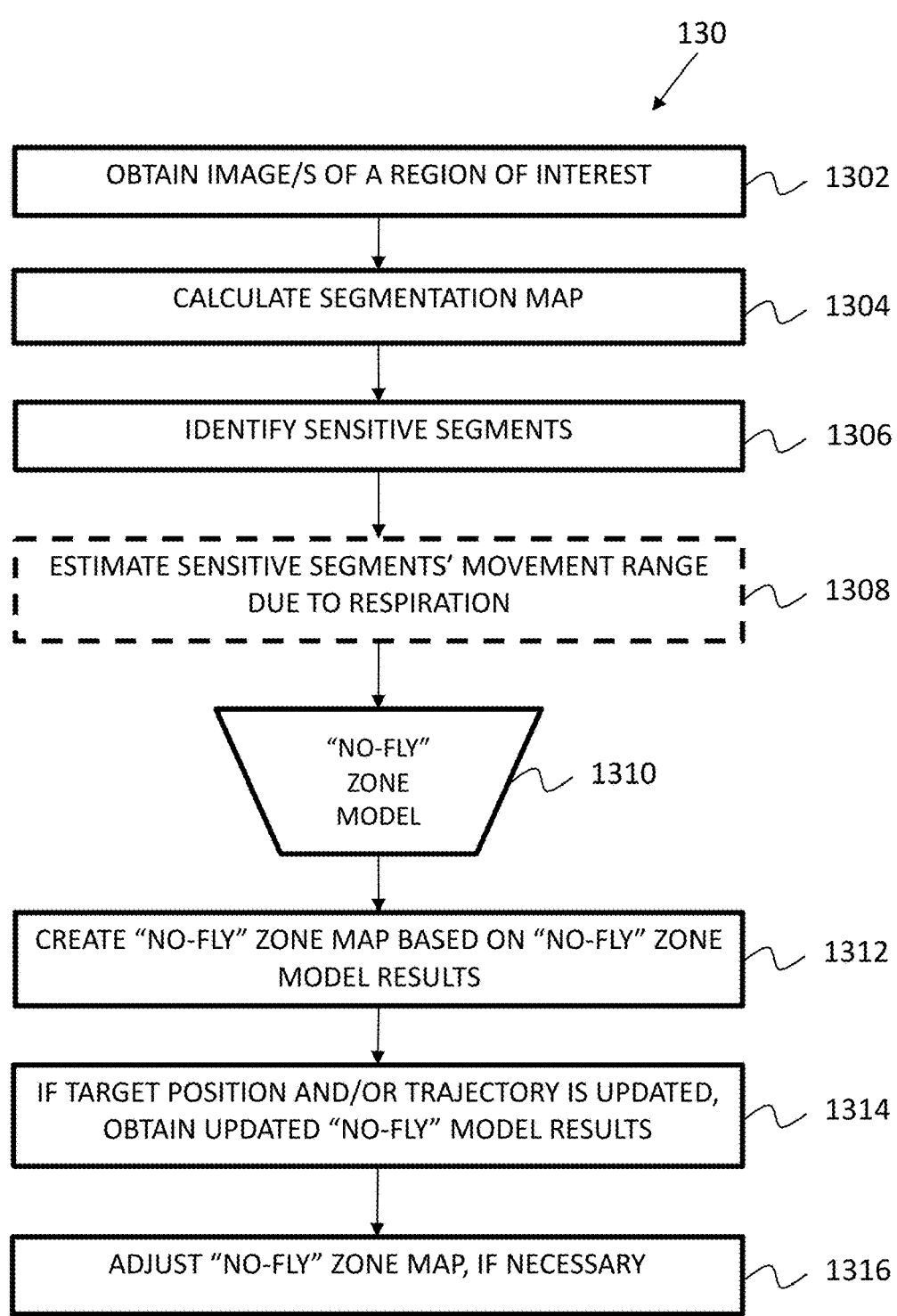
FIG. 13 shows a flowchart illustrating the steps of a method of utilizing an AI model for creating a "no-fly" zone map, according to some embodiments.

Reference is now made to FIG. 13, which shows a flowchart 130 illustrating the steps of a method of utilizing ("inference" process) an AI model for creating a "no-fly" zone map, according to some embodiments. In some embodiments, generating the AI model for creating a "no-fly" zone map (also referred to as "no-fly" zone model") may include training the model to predict "no-fly" zones as similar as possible to the ground truth "no-fly" zones map (i.e., with minimal error from the actual "no-fly" zones annotation map in previous similar procedures or additional relevant collected data available for training). In some embodiments, generating the "no-fly" zone model may include a preliminary phase, in which one or more individual models are trained. Such individual models may include an instrument's tip-to-target accuracy estimation model, a steering duration estimation model and/or a risk estimation model. In some embodiments, the target variable ("ground-truth) for training the tip-to-target accuracy model may be the procedure accuracy (e.g., instrument tip-to-target accuracy). In some embodiments, the target variable for training the risk model may be the occurrence of complications during the procedure. In some embodiments, the target variable for training the steering duration model may be the duration of the steering phase of the procedure. In some embodiments, the target variable for training the steering duration model may be the steering duration given a certain trajectory. In some embodiments, the trajectory may be estimated, at least in part, based on the "no-fly" zones predictions (recommendations). For example, a first "no-fly" zones prediction may enable a linear trajectory, whereas a second "no-fly" zones prediction may require a non-linear trajectory. As a linear trajectory is always the shortest route from the entry point to the target (given the same entry point and target positions), the first "no-fly" zones prediction also results in a shorter steering duration than the steering duration resulting from the second "no-fly" zones prediction. In embodiments in which generating the "no-fly" zone model includes training one or more individual models, the second phase of training the "no-fly" zone model may be executed using a loss function, e.g., Multi-Loss scheme, Ensemble Learning methods, Multi-Output regression/classification approach, Multi-Task Learning and the like. In some embodiments, the "no-fly" zone model may be trained using a Multi-Loss scheme, such that the "no-fly" zone map predicted by the "no-fly" zone model, together with the original input data, may be used as input to the individual models. The individual models' predictions, together with the "no-fly" zone model's prediction, may then be used to calculate a loss function, aimed to minimize the "no-fly" zones prediction error while, for example, minimizing the steering duration, maximizing the expected tip-to-target accuracy and minimizing the risk. The generated weighted loss represents the model's prediction error, which may be used to fine-tune or adjust the "no-fly" zones model's weights as part of the training process.

In some embodiments, only one or more of the individual models described above are used in the training process of the "no-fly" zone model. For example, in some embodiments only the accuracy and duration models may be used, whereas in other embodiments only the accuracy and risk models may be used. Further, the weights (coefficients) used in the loss function may be adjusted according to certain needs and/or preferences. For example, if minimal risk has a higher priority than "no-fly" zones prediction accuracy, tip-to-target accuracy and/or steering duration, risk may be given a higher coefficient during the training process, such that it will have a greater impact on the "no-fly" zones recommendation. In some embodiments, different "no-fly" zones models may be trained for different needs and/or preferences. For example, one "no-fly" zones model may be trained to generate a "no-fly" zones recommendation that will allow the highest achievable tip-to-target accuracy, another "no-fly" zones model may be trained to generate a "no-fly" zones recommendation that will allow the lowest achievable risk to the patient, a further "no-fly" zones model may be trained to generate a "no-fly" zones recommendation that will result in the shortest achievable duration, etc. In some embodiments, a single "no-fly" zones model may be trained and deployed, and the coefficients used in the Multi-Loss function may be adjusted during inference, i.e., during use of the "no-fly" zones model to generate a "no-fly" zones recommendation for a specific procedure. The need/preference upon which the coefficients may be fine-tuned may be associated with, for example, a specific procedure type (e.g., biopsy, fluid drainage, etc.), a specific target type, a specific user, specific patient characteristics, etc.

As shown in FIG. 13, at step 1302, images of a region of interest are obtained from an imaging system, such as a CT scanner, ultrasound, MRI, CBCT, etc. At step 1304, a segmentation map is calculated. The calculation may be done using a ML/DL based segmentation model capable of generating pixel-based 2D or 3D segmentation. In some embodiments, a semantic segmentation model may be used. In some embodiments, instance segmentation may be used. In some embodiments, the different segments and/or objects in the image(s) are classified to classes, such as organs, blood vessels, lesions, etc. In some embodiments, the classification may be pixel/voxel based. At step 1306, "risky" segments (also referred to as "sensitive segments" or "obstacles") are identified. Such segments may include, for example, bones, blood vessels, specific tissues, specific organs, etc. At optional step 1308, the movement range of the "risky" segments due to respiration motion may be estimated. The estimation may be based solely on image processing or it may be calculated using a separate data-analysis model. In some embodiments, the planning stage of the medical procedure (e.g., an image-guided interventional procedure) may include estimating the expected movement of the patient due to breathing based on a sequence of pre-operative images, and planning the trajectory for the instrument accordingly, as disclosed, for example, in co-owned U.S. Pat. No. 10,245,110, which is incorporated herein by reference in its entirety. Next, at step 1310, data and parameters obtained and/or calculated in the previous steps are used as input for the "no-fly" zone model and the model's results are obtained. It can be appreciated that additional data may be used as input for the model, as described in detail hereinabove. At step 1312, a "no-fly" zone map is created based on the results of the "no-fly" zone model. At step 1314, if the images obtained from the imaging system during the steering procedure show that the target has moved from its initial position (or from its previously identified position) and/or if the trajectory is updated due target movement, due to deviation of the instrument from the planned trajectory above a predetermined threshold and/or due to an obstacle identified along the planned trajectory, updated results may be obtained from the "no-fly" zone model, and at step 1316, the "no-fly" zone map may be adjusted according to the updated model results, if necessary. In some embodiments, if checkpoints are set along the trajectory such that upon the instrument reaching a checkpoint, advancement of the instrument is paused and imaging is initiated, steps 1312 and 1314 may be executed at each checkpoint. In some embodiments, if the medical procedure is performed under continuous or substantially continuous imaging (e.g., using a CT fluoroscopy system or an ultrasound system), steps 1312 and 1314 may be executed continuously or at defined temporal or spatial intervals during the procedure.

Figure 14:
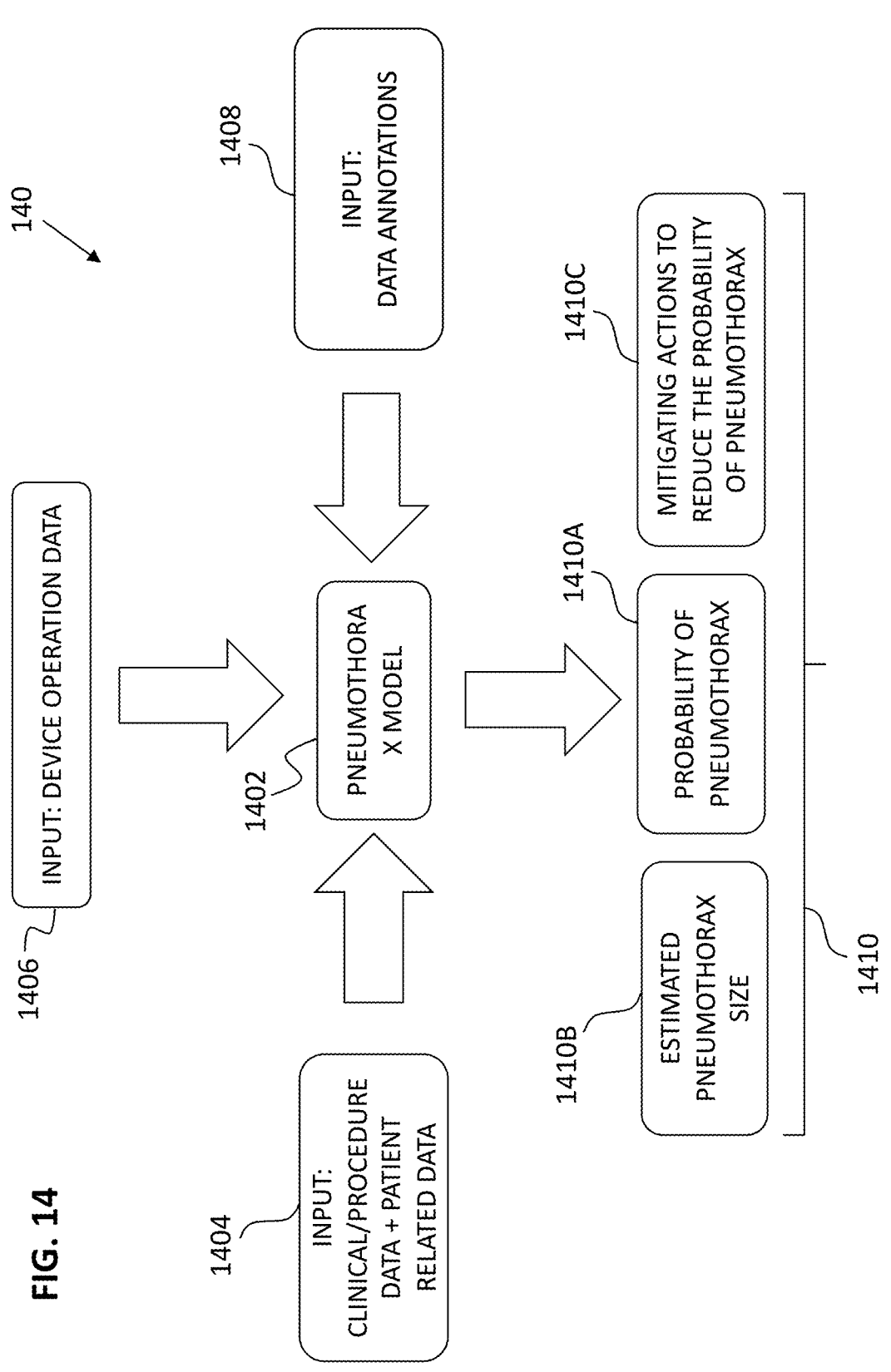
FIG. 14 shows a block diagram of exemplary datasets used for generating an AI model for prediction and/or detection of pneumothorax, and exemplary output of the checkpoint model, according to some embodiments.

Reference is now made to FIG. 14, which shows a block diagram 140 of datasets and parameters used for generating an AI model for prediction and/or detection of pneumothorax (also referred to as "pneumothorax prediction model", "pneumothorax detection model" or "pneumothorax model") 1402, according to some embodiments. A pneumothorax occurs when air enters the pleural sac, i.e., the space between the lung and the chest wall, pushing on the outside of the lung and causing the lung to collapse. Pneumothorax can be a complete lung collapse or a partial lung collapse, and it can inadvertently occur during medical procedures that involve the insertion of a medical instrument (e.g., needle) into the chest, such as lung biopsy. Pneumothorax may be life-threatening, thus it may be advantageous to train AI model(s) to predict and/or detect the occurrence of pneumothorax during a medical procedure and, optionally, recommend actions that may prevent the occurrence of pneumothorax, prevent worsening of a developing pneumothorax and/or enable early treatment to an existing pneumothorax. Such AI model(s) may be employed, for example, when a medical instrument is inserted into the lung for the purpose of performing a lung biopsy or in a medical procedure which is adjacent to the pleura.

In some embodiments, the input datasets may include, for example, but not limited to: data related to clinical procedure and patient related data 1404, such as, target (e.g., lesion) size, target depth, medical instrument (needle) type and gauge, needle tip type (e.g., diamond, bevel), respiration signals, respiration abnormalities, patient characteristics (age, gender, race, lung function, BMI, previous lung procedures, clinical condition, smoking habits, etc.); data related to the medical device and its operation 1406, including, for example, motors' current traces (i.e. logs of motors' performance data), procedure timing, skin to target time, entry and target positions, trajectory length, target movements and paths updates, number and position of checkpoints, errors and correction of checkpoints, images (e.g., CT scans) generated during the procedure (e.g., at checkpoints), magnitude of lateral steering of the medical instrument, medical device position, insertion angles, final tip-to-target accuracy (distance, depth, lateral), fissure crossed, bulla crossed, pleura crossed, distance of target from lung wall, patient's position (e.g., supine, prone, decubitus), location of target (e.g., in the right lung or the left lung), etc. In addition, data annotations 1408 are further utilized for model training and validation, including, for example, whether a pneumothorax has been detected in past (similar) procedures, pneumothorax size, pneumothorax location (e.g., as marked on the scan/s), etc. Once the pneumothorax model is generated and validated, based on the various datasets, output (results/predictions) 1410 may be provided. Such output may be, for example, the probability of pneumothorax 1410A, the estimated pneumothorax size 1410B, potential modifications 1410C which could reduce the probability of pneumothorax, and the like, or any combination thereof.

In some embodiments, the output of the model 1402 may be communicated to a user, for example, visually on a graphical user interface (GUI) on a display of the medical device/system, a controller system, a mobile device, a Virtual Reality (VR) device and/or an Augmented Reality (AR) device, and the like. In some embodiments, the output (for example, a recommendation) of the model 1402 may be communicated to a healthcare provider, which may allow (or not allow) the execution of the recommendation. In some embodiments, the execution of the recommendation issued by the model 1402 may be performed automatically after being communicated to an automated medical device.

Figure 15:
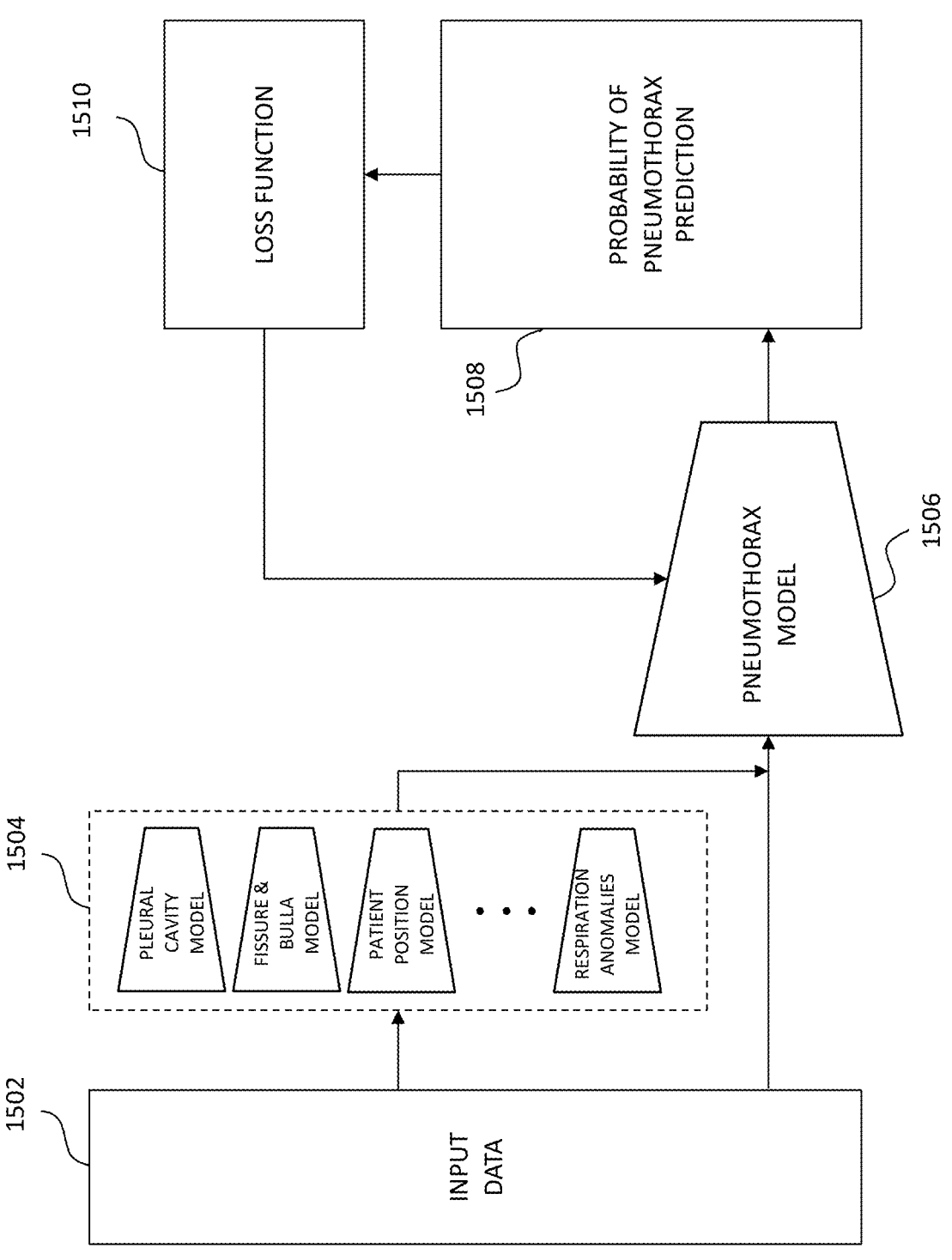
FIG. 15 shows a block diagram illustrating an exemplary method of generating an AI model for prediction and/or detection of pneumothorax, according to some embodiments.

Reference is now made to FIG. 15, which shows a block diagram 150 illustrating an exemplary method of generating (training) an AI model for prediction and/or detection of pneumothorax ("pneumothorax model"). As shown in FIG. 15, input data 1502, such as input described in FIG. 14, is used to train the pneumothorax model 1504 to estimate the probability of pneumothorax occurrence 1506. The input data 1502 may include multi-modal data collected from past procedures and arranged, where possible/applicable, as time-series together with the patient's parameters and medical history. The time-series structure may allow the analysis of time-dependency events in past procedures' data to better predict the probability for pneumothorax occurrence during a procedure and better study the impact of the different risk factors and their correlation to the procedure timeline. In some embodiments, specialized feature extraction models 1504 may be used to generate meaningful domain-knowledge features that may, in turn, be input to the primary pneumothorax model 1506 during the training process. Such specialized features extraction models 1504 may be, for example, a pleural cavity volume (and/or size and/or shape) estimation model, a fissure and bulla crossing model, patient position model, respiration anomalies model, etc. the specialized feature extraction models 1504 may be trained on relevant portions of the input data and their output may be input to the primary pneumothorax model 1506 together with the remaining multi-modal data. In some embodiments, the output of the pneumothorax model 1506 may be prediction 1508 of the probability of pneumothorax occurrence in the current procedure. This prediction, together with ground-truth annotations regarding the occurrence of pneumothorax during a procedure, may be used to calculate a loss function 1510 representing the error between the pneumothorax model's prediction and the ground-truth data. During the training process, optimization of this loss function will allow the adjustment of the model's weights. In some embodiments, the pneumothorax model may be trained in a multi-task and/or multi-output approach. In such embodiments, the model may predict, for example, the point in time representing the beginning of an active pneumothorax condition, in addition to the probability of pneumothorax occurrence. In some embodiments, the pneumothorax model 1506 may be trained to predict the exact risk of pneumothorax at each point in time during the procedures. This may require corresponding time-based annotations of pneumothorax risk level at desired points in time throughout the procedures in the dataset. In some embodiments, the pneumothorax model may be trained to predict the primary identified risk factors and/or their contribution to the overall pneumothorax occurrence probability.

Reference is now made to FIG. 16, which shows a flowchart 160 illustrating the steps of a method of utilizing (an "inference" process) a pneumothorax model for prediction, early detection and/or prevention of pneumothorax. At step 1602, patient data may be, optionally, obtained. Such data may include, for example, but not limited to: age, gender, BMI, smoking habits, etc. Patient data may further include the patient's medical history, such as the patient's lung function, previous medical procedures (specifically, lung procedures), previous occurrences of pneumothorax, medical condition, etc. At step 1604, characteristics of the medical instrument to be used in the procedure are obtained. Such characteristics may include, for example, instrument type (e.g., introducer, biopsy needle, ablation probe, etc.), instrument gauge, instrument tip type (e.g., diamond tip, bevel tip), etc. At step 1606, the patient's position (pose) on the procedure bed is obtained. The patient's pose may be, for example, supine, prone, decubitus, etc. At step 1608, one or more images of a region of interest are obtained from an imaging system (e.g., CT, ultrasound, MRI, X-Ray, CBCT). At step 1610, a segmentation map may be calculated, according to some embodiments. The calculation may be done using a ML/DL based segmentation model capable of generating pixel-based 2D or 3D segmentation. In some embodiments, a semantic segmentation model may be used. In some embodiments, instance segmentation may be used. In some embodiments, the different segments and/or objects in the image(s) are classified to classes, such as organs, blood vessels, lesions, etc. In some embodiments, the classification may be pixel/voxel based. At step 1612, the target, entry point and, optionally, "no-fly" zones are obtained or identified, and a trajectory for the medical instrument from the entry to the target, which avoid entrance into the "no-fly" zones (if marked), is calculated. In some embodiments, at least one of the target, entry point and "no-fly" zones may be marked on the image(s) manually by the user. In some embodiments, at least one of the target, entry point and "no-fly" zones may be identified by a processor using image processing and/or using dedicated data-analysis algorithms. For example, a "no-fly" zone map may be created using the "no-fly" zone model described in FIG. 13 hereinabove. In some embodiments, the trajectory may be calculated based solely on the pre-operative images of the region of interest, for example as disclosed in abovementioned co-owned International Patent Application No. PCT/IL2020/051219.

In some embodiments, the trajectory may be calculated using a dedicated data-analysis algorithm, such as an AI model, using data from previous (similar) procedures. In some embodiments, the planned trajectory is a planner trajectory (2D). In some embodiments, the planned trajectory is three-dimensional. In some embodiments, two or more planner trajectories are first planned on two or more planes disposed at an angle relative to each other, and the two or more planner trajectories are then superpositioned to form a planned 3D trajectory. At step 1614, the locations of critical tissues, such as the lung, pleura, fissures, bulla(e) (if exists(s)), etc. At step 1616, the pleural cavity (sac) is detected and its volume is determined. Once determined, the pleural cavity volume is monitored to detect changes in the volume, specifically—enlargement thereof. The pleural cavity volume may be determined/monitored using image processing, sensor data and/or tissue compliance, for example. At step 1618, the patient's respiration patterns may, optionally, be monitored. Certain changes in the patient's respiration patterns may be indicative of a pneumothorax developing. At step 1620, data and parameters obtained and/or calculated in the previous steps are used as input for the pneumothorax model and the model's output is obtained. It can be appreciated that additional data may be used as input for the model, as described in detail hereinabove. In some embodiments, the model's output may include, for example, the probability of pneumothorax and the pneumothorax size, etc. At step 1622, it is determined if the probability of pneumothorax occurrence is above a defined threshold. In some embodiments, the threshold is determined automatically, e.g., based, at least in part, on past similar cases (e.g., similar procedures and/or similar patient characteristics, etc.). In such embodiments, the determination if the probability of pneumothorax is above a threshold may be included in the results of the pneumothorax model. In some embodiments, the threshold is determined by the healthcare provider (e.g., physician), and the determination if the pneumothorax probability is above a threshold is a clinical decision of the healthcare provider. At step 1624, if it is determined (either by the processor or by the healthcare provider) that the probability of pneumothorax occurrence is above a defined threshold, then if the calculations were executed during the planning stage of the procedure, the processor may alert the user (for example, by displaying a visual alert on the GUI and/or generating an auditory notification) and suggest mitigating actions to reduce the probability of pneumothorax occurring during the procedure, such as repositioning the automated medical device, selecting a different entry point, using a different medical instrument (e.g., an instrument with a higher gauge (thinner tool)), etc. In embodiments in which the probability threshold and the probability of pneumothorax being above a threshold are determined by the processor and are part of the output of the pneumothorax model, the recommendation of mitigating actions to reduce the probability of pneumothorax may also be part of the output of the pneumothorax model. If mitigating actions to reduce the risk of pneumothorax cannot be executed, or if there are no (or insufficient) possible mitigating actions, the processor may recommend to the user not to perform the procedure. If mitigating actions have been implemented then, at step 1626, the probability of pneumothorax is recalculated. If the probability is now below the defined threshold, or if the initial calculated probability was below the defined threshold, then the instrument steering procedure is executed, and recalculation of the probability of pneumothorax is repeated during the procedure. In some embodiments, if checkpoints have been set along the trajectory, the probability of pneumothorax may be recalculated upon the instrument reaching each of checkpoints. In some embodiments, the probability of pneumothorax may be recalculated at a checkpoint only if the target position and/or the trajectory are updated. In some embodiments, the probability of pneumothorax may be recalculated only upon the instrument reaching the checkpoint closest to the lung (specifically, to the pleura). In some embodiments, if the instrument steering procedure is performed under continuous or substantially continuous imaging (e.g., using a CT fluoroscopy system, CBCT system or an ultrasound system), the probability of pneumothorax may be recalculated continuously or at defined temporal or spatial intervals during the procedure until the instrument reaches the target.

In some embodiments, if the pneumothorax probability calculations were executed during the instrument steering procedure and none (or an insufficient number) of the risk factors can be adjusted in order to reduce the probability of pneumothorax, then if it is determined that the probability of pneumothorax is above the threshold, an alert may be generated (for example, a visual alert displayed on the GUI and/or an auditory notification). In some embodiments, the processor may further prompt the user to stop the steering procedure. In some embodiments, the processor may automatically stop the steering procedure.

Reference is now made to FIG. 17, which shows a flowchart 170 illustrating the steps of a method utilizing (an "inference" process) an AI model for prediction and/or detection of internal bleeding (also referred to as "bleeding model", "internal bleeding model" or "bleeding prediction model"), according to some embodiments. Training of the bleeding prediction model may be performed similarly to the training described in FIG. 15 hereinabove, such that multi-modal data, structured as time-series (where applicable), is used as input to the bleeding prediction model. The model's output may be a prediction of the probability of bleeding, and the ground-truth data regarding the occurrence of bleeding during past procedures included in the dataset, may be used to calculate a loss function that will represent the error between the model's prediction of internal bleeding and the ground-truth labels. During the training process, optimization of the loss function will allow the adjustment of the model's weights for optimal prediction. In some embodiments, the bleeding model may be trained in a multi-task and/or multi-output approach, such that it may predict, for example, the point in time representing the beginning of an active bleeding condition, in addition to the probability for bleeding occurrence. In some embodiments, the internal bleeding model may be trained to predict the exact risk of bleeding at each point in time during the procedures. This may require corresponding time-based annotations of bleeding risk level at desired points in time throughout the procedures in the dataset. In some embodiments, the bleeding model may be trained to predict the primary identified risk factors and/or their contribution to the overall bleeding occurrence probability.

As shown in FIG. 17, at step 1702, patient data may optionally be obtained. Such data may include, for example, but not limited to: age, gender, BMI, etc. Patient data may further include the patient's medical history, such as the patient's medical condition, existing vascular disease(s), previous medical procedures, previous occurrence(s) of bleeding during medical procedures, etc. At step 1704, one or more images of a region of interest are obtained from an imaging system (e.g., CT, ultrasound, MRI, X-Ray, CBCT). At step 1706, a segmentation map may be calculated, according to some embodiments. The calculation may be done using a ML/DL based segmentation model capable of generating pixel-based 2D or 3D segmentation. In some embodiments, a semantic segmentation model may be used. In some embodiments, instance segmentation may be used. In some embodiments, the different segments and/or objects in the image(s) are classified to classes, such as organs, blood vessels, lesions, etc. In some embodiments, the classification may be pixel/voxel based. At step 1708, the target, entry point and, optionally, "no-fly" zones are obtained or identified, and a trajectory for the medical instrument from the entry to the target, which avoid entrance into the "no-fly" zones (if marked), is calculated. In some embodiments, at least one of the target, entry point and "no-fly" zones may be marked on the image(s) manually by the user. In some embodiments, at least one of the target, entry point and "no-fly" zones may be identified by a processor using image processing and/or using dedicated data-analysis algorithms. For example, a "no-fly" zone map may be created using the "no-fly" zone model described in FIG. 13 hereinabove. In some embodiments, the trajectory may be calculated based solely on the pre-operative images of the region of interest, for example as disclosed in abovementioned co-owned International Patent Application No. PCT/IL2020/051219. In some embodiments, the trajectory may be calculated using a dedicated data-analysis algorithm, such as an AI model, using data from previous (similar) procedures. In some embodiments, the planned trajectory is a planner trajectory (2D). In some embodiments, the planned trajectory is three-dimensional. In some embodiments, two or more planner trajectories are first planned on two or more planes disposed at an angle relative to each other, and the two or more planner trajectories are then superpositioned to form a planned 3D trajectory. At step 1710, blood vessels along the planned trajectory may be detected. In some embodiments, the identified blood vessels are further classified to blood vessel types, such as artery, vein, etc. In some embodiments, critical organs, i.e., organs which are more susceptible to bleed, if punctured, and/or organs which, if punctured, the resultant bleeding may lead to a life-threating condition, are also detected and/or classified. In some embodiments, if a "no-fly" zone map is created, the step of detecting and/or classifying blood vessels and/or critical organs, may be part of the creation of the "no-fly" zone map (step 1708). At step 1712, data and parameters obtained and/or calculated in the previous steps are used as input for the bleeding model and the model's output is obtained. It can be appreciated that additional data may be used as input for the model, as described in detail hereinabove. In some embodiments, the model's output may include, for example, the probability that internal bleeding will occur during the medical procedure. During the planning phase of the procedure, the calculation of the probability that internal bleeding will occur during the procedure may be based, for example, on the planned trajectory, the location of blood vessels and/or critical organs along the trajectory and/or the patient's characteristics detailed above. At step 1714, it is determined if the probability that internal bleeding will occur during the procedure is above a defined threshold. In some embodiments, the threshold is determined automatically, e.g., based, at least in part, on past similar cases (e.g., similar procedures and/or similar patient characteristics, etc.). In such embodiments, the determination if the probability is above a threshold may be included in the results of the bleeding prediction model. In some embodiments, the threshold is determined by the healthcare provider (e.g., physician), and the determination if the bleeding probability is above a threshold is a clinical decision of the healthcare provider. At step 1716, if it is determined (either by the processor or by the healthcare provider) that the probability of internal bleeding occurrence is above a defined threshold, then the processor may alert the user (for example, by displaying a visual alert on the GUI and/or generating an auditory notification) and suggest mitigating actions to reduce the probability of internal bleeding occurring during the procedure, such as repositioning the medical device, selecting a different entry point, adjusting the "no-fly" zones, adjusting the checkpoint locations along the trajectory and/or recalculating the trajectory, etc. In embodiments in which the probability threshold and the probability of bleeding occurrence being above a threshold are determined by the processor and are part of the output of the bleeding model, the recommendation of mitigating actions to reduce the probability of internal bleeding may also be part of the output of the bleeding model. After mitigating actions have been implemented, the probability of bleeding occurring during the procedure may be recalculated (at step 1712). If the probability is now below the defined threshold (at step 1714), or if the initial calculated probability was below the defined threshold, then the medical procedure is executed and, at step 1718, the probability of bleeding occurrence is repeated during the procedure, using the internal bleeding model. In some embodiments, the output of the model during the insertion procedure may include, instead or in addition to the prediction of bleeding occurring during subsequent steps of the procedure, a prediction/detection that bleeding is occurring (present tense), as well as the suspected location of the bleeding in the patient's body and additional characteristics of the bleeding. Such characteristics may be, for example, estimated bleeding rate, estimated bleeding volume and additional characteristics which may be indicative of the severity of the bleeding. In some embodiments, if checkpoints have been set along the trajectory, the bleeding probability may be recalculated upon the instrument reaching each of checkpoints. In some embodiments, the bleeding probability may be recalculated at a checkpoint only if there are changes in certain parameters, for example, if the target position and/or the trajectory are updated, if the checkpoint location are adjusted, if the scan volume is changed, etc. In some embodiments, if the instrument steering procedure is performed under continuous or substantially continuous imaging (e.g., using a CT fluoroscopy system, CBCT system or an ultrasound system), the probability of internal bleeding may be recalculated continuously or at defined temporal or spatial intervals during the procedure until the instrument reaches the target. At step 1720, it is determined if the probability that there is (present tense) internal bleeding and/or that bleeding will occur during following steps of the procedure is above a defined threshold, similarly to step 1714. At step 1722, if it is determined (either by the processor or by the healthcare provider) that the probability of internal bleeding occurrence is above the defined threshold, then the processor may alert the user and present to the user the suspected location of the bleeding (existing or predicted). In some embodiments, additional characteristics of the bleeding may be presented to the user, such as estimated bleeding rate, etc. At step 1724, if it is decided to continue the steering procedure, either following an assessment by the processor or a clinical decision of the physician, then the probability of bleeding may be recalculated (at step 1718) continuously or at one or more checkpoints, for example, until the instrument reaches the target. If it is decided to terminate the procedure due to the bleeding (existing or predicted), either following an assessment by the processor or a clinical decision of the physician, then the process ends, at step 1726.

Implementations of the systems, devices and methods described above may further include any of the features described in the present disclosure, including any of the features described hereinabove in relation to other system, device and method implementations.

According to some embodiments, there is provided computer-readable storage medium having stored therein data-analysis algorithm(s), executable by one or more processors, for generating one or more models for providing recommendations, operating instructions and/or functional enhancements related to operation of automated medical devices.

The embodiments described in the present disclosure may be implemented in digital electronic circuitry, or in computer software, firmware or hardware, or in combinations thereof. The disclosed embodiments may be implemented as one or more computer programs, i.e., one or more modules of computer program instructions, encoded on computer storage medium for execution by, or to control the operation of, one or more data processing apparatus. Alternatively or in addition, the computer program instructions may be encoded on an artificially generated propagated signal, for example, a machine-generated electrical, optical or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of any one or more of the above. Furthermore, while a computer storage medium is not a propagated signal, a computer storage medium can be a source or destination of computer program instructions encoded in an artificially generated propagated signal. The computer storage medium can also be, or be included in, one or more separate physical components or media (for example, multiple CDs, disks, or other storage devices).

The operations described in the present disclosure can be implemented as operations performed by a data processing apparatus on data stored on one or more computer-readable storage devices or received from other sources.

The term "data processing apparatus" as used herein may encompass all types of apparatus, devices, and machines for processing data, including by way of example a programmable processor, a computer, a system on a chip/s, or combinations thereof. The data processing apparatus can include special purpose logic circuitry, for example, an FPGA (field programmable gate array) or an ASIC (application specific integrated circuit). The apparatus can also include, in addition to hardware, code that creates an execution environment for the computer program in question, for example, code that constitutes processor firmware, a protocol stack, a database management system, an operating system, a cross-platform runtime environment, a virtual machine, or combinations thereof. The apparatus and execution environment can realize various different computing model infrastructures, such as web services, distributed computing and grid computing infrastructures.

A computer program (also referred to as a program, software, software application, script or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A computer program can be stored in a portion of a file that holds other programs or data, in a single file dedicated to the program in question, or in multiple coordinated files (for example, files that store one or more modules, sub programs or portions of code). A computer program can be deployed to be executed on one computer or on multiple computers that are located at one site or distributed across multiple sites and interconnected by a communication network.

The processes and logic flows described herein can be performed by one or more programmable processors, executing one or more computer programs to perform actions by operating on input data and generating output. The processes and logic flows can also be performed by, and an apparatus can also be implemented as, special purpose logic circuitry, for example, an FPGA or an ASIC. Processors suitable for the execution of a computer program include both general and special purpose microprocessors, and any one or more processors of any type of digital computer. Generally, a processor will receive instructions and data from a read-only memory or a random access memory or both. The essential elements of a computer are a processor for performing actions in accordance with instructions and one or more memory devices for storing instructions and data. A computer may, optionally, also include, or be operatively coupled to receive data from or transfer data to, or both, one or more mass storage devices for storing data, for example, magnetic, magneto optical discs, or optical discs. Moreover, a computer can be embedded in another device, for example, a mobile phone, a tablet, a personal digital assistant (PDA, a game console, a Global Positioning System (GPS) receiver, or a portable storage device (for example, a USB flash drive). Devices suitable for storing computer program instructions and data include all forms of non-volatile memory, media and memory devices, including semiconductor memory devices, for example, EPROM, EEPROM, random access memories (RAMs), including SRAM, DRAM, embedded DRAM (eDRAM) and Hybrid Memory Cube (HMC), and flash memory devices; magnetic discs, for example, internal hard discs or removable discs; magneto optical discs; read-only memories (ROMs), including CD-ROM and DVD-ROM discs; solid state drives (SSDs); and cloud-based storage. The processor and the memory can be supplemented by, or incorporated in, special purpose logic circuitry.

The processes and logic flows described herein may be performed in whole or in part in a cloud computing environment. For example, some or all of a given disclosed process may be executed by a secure cloud-based system comprised of co-located and/or geographically distributed server systems. The term "cloud computing" is generally used to describe a computing model which enables on-demand access to a shared pool of computing resources, such as computer networks, servers, software applications, and services, and which allows for rapid provisioning and release of resources with minimal management effort or service provider interaction.

Unless specifically stated otherwise, as apparent from the disclosure, it is appreciated that, according to some embodiments, terms such as "processing", "computing", "calculating", "determining", "estimating", "assessing" or the like, may refer to the action and/or processes of a computer or computing system, or similar electronic computing device, that manipulate and/or transform data, represented as physical (e.g. electronic) quantities within the computing system's registers and/or memories, into other data similarly represented as physical quantities within the computing system's memories, registers or other such information storage, transmission or display devices.

It is to be understood that although some examples used throughout this disclosure relate to procedures for insertion of a needle into a subject's body, this is done for simplicity reasons alone, and the scope of this disclosure is not meant to be limited to insertion of a needle into the subject's body, but is understood to include insertion of any medical tool/ instrument into the subject's body for diagnostic and/or therapeutic purposes, including a port, probe (e.g., an ablation probe), introducer, catheter (e.g., drainage needle catheter), cannula, surgical tool, fluid delivery tool, or any other such insertable tool.

In some embodiments, the term medical instrument and medical tool may be used interchangeably.

In some embodiments, the term "model", "algorithm", "data-analysis algorithm" and "data-based algorithm" may be used interchangeably.

In some embodiments, the terms "user", "doctor", "physician", "clinician", "technician", "medical personnel" and "medical staff" are used interchangeably throughout this disclosure and may refer to any person taking part in the performed medical procedure.

It can be appreciated that the terms "subject" and "patient" may be used interchangeably, and they may refer either to a human subject or to an animal subject.

In the description and claims of the application, the words "include" and "have", and forms thereof, are not limited to members in a list with which the words may be associated.

Unless otherwise defined, all technical and scientific terms used herein have the same meaning as commonly understood by one of ordinary skill in the art to which this disclosure pertains. In case of conflict, the patent specification, including definitions, governs. As used herein, the indefinite articles "a" and "an" mean "at least one" or "one or more" unless the context clearly dictates otherwise.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. No feature described in the context of an embodiment is to be considered an essential feature of that embodiment, unless explicitly specified as such.

Although steps of methods according to some embodiments may be described in a specific sequence, methods of the disclosure may include some or all of the described steps carried out in a different order. The methods of the disclosure may include a few of the steps described or all of the steps described. No particular step in a disclosed method is to be considered an essential step of that method, unless explicitly specified as such.

The phraseology and terminology employed herein are for descriptive purpose and should not be regarded as limiting. Citation or identification of any reference in this application shall not be construed as an admission that such reference is available as prior art to the disclosure. Section headings are used herein to ease understanding of the specification and should not be construed as necessarily limiting.

What is claimed is:

1. A computer-implemented method of generating a checkpoint locations model for optimizing locations of a plurality of checkpoints along a non-linear trajectory in an image-guided procedure for inserting a medical instrument toward a target in a body of a patient, using an automated medical device, the method comprising:

collecting one or more datasets, at least one of the one or more datasets being related to an automated medical device configured to steer a medical instrument toward a target in the body of a patient and/or to operation thereof;

creating a training set comprising at least a portion of the one or more datasets and one or more target parameters relating to checkpoint locations along a non-linear trajectory in one or more previous image-guided procedures for automatically inserting a medical instrument toward a target in a body of a patient;

training the checkpoint locations model to predict checkpoint locations using the training set;

calculating a checkpoint locations prediction error; and optimizing the checkpoint locations model using the calculated checkpoint locations prediction error, wherein the checkpoint locations model dynamically updates predicted checkpoint locations during execution of the image-guided procedure based on real-time feedback received from the automated medical device and procedural imaging data; and adjusting trajectory parameters of the automated medical device in real time according to the dynamically updated checkpoint locations.

2. The computer-implemented method of claim 1, wherein the one or more datasets further comprise one or more of: clinical procedure related dataset, patient related dataset and administrative related dataset.

3. The computer-implemented method of claim 2, wherein the clinical procedure related dataset comprises parameters selected from: medical procedure type, target organ, target size, target type, type of medical instrument, dimensions of the medical instrument, clinical complications before, during and/or after the procedure, complications detection time, adverse events before, during and/or after the procedure, respiration signals of the patient, or any combination thereof;

wherein the patient related dataset comprises parameters selected from: age, gender, race, medical condition, medical history, vital signs before, after and/or during the procedure, body dimensions, pregnancy, smoking habits, demographic data, or any combination thereof;

wherein the administrative related dataset comprises parameters selected from: institution, physician, staff, system serial number, disposable components used in the procedure, software version, operating system version, configuration parameters, or any combination thereof.

4. The computer-implemented method of claim 2, wherein one or more of the parameters of the one or more datasets is configured to be collected automatically.

5. The computer-implemented method of claim 1, wherein the automated medical device related dataset comprises parameters selected from: entry point, insertion angles, target position, target position updates, target contour and/or bounding box and/or location, "no-fly" zones masks and/or bounding boxes and/or locations, organs segmentation masks and/or bounding boxes and/or locations, tissues segmentation mask and/or bounding boxes and/or locations, blood vessels mask and/or bounding boxes and/or locations, planned trajectory, trajectory updates, real-time positions of the medical instrument, number of checkpoints along the planned and/or updated trajectory, checkpoint locations, checkpoint locations updates, checkpoint errors, position of the automated medical device, steering steps timing, procedure duration, steering phase duration, procedure accuracy, target error, medical images, medical imaging parameters per scan, radiation dose per scan, total radiation dose in steering phase, total radiation dose procedure, sensor(s) measurements, errors indicated during the steering procedure, software logs, motion control traces, automated medical device registration logs, medical instrument detection logs, homing and BIT results, or any combination thereof.

6. The computer-implemented method of claim 1, further comprising:

executing one or more individual models using at least a portion of the one or more datasets and a checkpoint locations prediction generated by the checkpoint locations model; and obtaining one or more predictions from the one or more individual models.

7. The computer-implemented method of claim 6, further comprising:

calculating a loss function using a checkpoint locations prediction error and the one or more predictions generated by the one or more individual models;

optimizing the checkpoint locations model using the loss function; and training the one or more individual models.

8. The computer-implemented method of claim 7, wherein calculating the loss function comprises minimizing one or more of the checkpoint locations prediction error, the predicted radiation dose, the predicted duration and the predicted risk, and maximizing the predicted accuracy of the image-guided insertion procedure.

9. The computer-implemented method of claim 7, further comprising adjusting one or more coefficients of one or more terms used in the calculation of the loss function, the one or more terms being associated with at least one of the checkpoint locations prediction error and the one or more predictions generated by the one or more individual models;

wherein the adjusting of the one or more coefficients is executed during training of the checkpoint locations model;

wherein the adjusting of the one or more coefficients is executed during execution of the checkpoint locations model.

10. The computer-implemented method of claim 6, wherein the one or more individual models comprise one or more of: a model for predicting an accuracy of an image-guided insertion procedure, a model for predicting a radiation dose emitted during an image-guided insertion procedure, or part thereof, a model for predicting a duration of an image-guided insertion procedure, or part thereof, and a model for predicting a risk of an image-guided insertion procedure.

11. The computer-implemented method of claim 1, wherein the automated medical device is configured to steer the medical instrument toward the target such that the medical instrument traverses a non-linear trajectory within the body of the patient and/or, wherein the automated medical device is configured to allow real-time updating of a trajectory of the medical instrument.

12. The computer-implemented method of claim 1, further comprising:

collecting one or more new datasets, at least one of the one or more new datasets being related to an automated medical device configured to steer a medical instrument toward a target in a body of a patient and/or to operation thereof and comprising one or more images of a region of interest and a planned trajectory for the medical instrument from an entry point to the target;

detecting one or more tissue boundaries in the one or more images;

executing the checkpoint locations model using at least a portion of the one or more new datasets;

obtaining an output of the checkpoint locations model;

setting one or more checkpoints along the planned trajectory based on the output of the checkpoint locations model, and estimating a scan volume and a radiation dose per checkpoint.

13. The computer-implemented method of claim 12, further comprising the step of obtaining from a user at least one of a confirmation to the set one or more checkpoints and an adjustment thereto.

14. The computer-implemented method of claim 12, further comprising the step of defining one or more sections along the planned trajectory in which no checkpoints are to be positioned, so as to allow the medical instrument to be continuously advanced along the one or more sections.

15. The computer-implemented method of claim 12, wherein if at least one of a position of the target and the planned trajectory are updated upon reaching a checkpoint, the method further comprises the steps of re-executing the checkpoint locations model and obtaining an updated output of the checkpoint locations model; adjusting the locations of one or more subsequent checkpoints based on the updated output of the checkpoint locations model; and; obtaining from a user at least one of a confirmation to the adjusted locations of the one or more subsequent checkpoints and an adjustment thereto.

16. A system for utilizing a checkpoint locations model for optimizing locations of checkpoints along a trajectory in an image-guided procedure for inserting a medical instrument to a target in a body of a patient, the system comprising:

an inference module comprising:

a memory configured to store the one or more datasets; and one or more processors configured to: collect one or more datasets, at least one of the one or more datasets being related to an automated medical device configured to steer a medical instrument toward a target in the body of a patient and/or to operation thereof;

create a training set comprising at least a portion of the one or more datasets and one or more target parameters relating to checkpoint locations along a trajectory in one or more previous image-guided procedures for inserting a medical instrument toward a target in a body of a patient;

train the checkpoint locations model to predict checkpoint locations using the training set;

calculate a checkpoint locations prediction error, and optimize the checkpoint locations model using the calculated checkpoint locations prediction error, wherein the checkpoint locations model is configured to dynamically update predicted checkpoint locations during execution of the image-guided procedure based on real-time feedback received from the automated medical device and procedural imaging data; and adjust trajectory parameters of the automated medical device in real time according to the dynamically updated checkpoint locations.

17. The system of claim 16, wherein one or more processors are further configured to real-time update a trajectory of the medical instrument.

18. The system of claim 17, wherein if at least one of a position of the target and the planned trajectory are updated upon reaching a checkpoint, the one or more processors are further configured to re-execute the checkpoint locations model and obtaining an updated output of the checkpoint locations model;

adjust the locations of one or more subsequent checkpoints based on the updated output of the checkpoint locations model;

obtain from a user at least one of a confirmation to the adjusted locations of the one or more subsequent checkpoints and an adjustment thereto.

19. The system of claim 16, wherein the inference module is located on a remote server, an "on premise" server or a computer associated with the automated medical device.

20. The system of claim 19, wherein the remote server is a cloud server.

* * * * *